US012728281B2

United States Patent
(12) United States Patent
Shah et al.

(10) Patent No.: US 12,728,281 B2
(45) Date of Patent: Sep. 8, 2026

(54) UV RADIATION DEVICES AND METHODS OF USE THEREOF

(71) Applicant: Photon Therapeutics Ltd., Caterham (GB)

(72) Inventors: Sunil Shah, Birmingham (GB); Simon Dean, Auckland (NZ)

(73) Assignee: Photon Therapeutics Ltd., London (GB)

(*) Notice: Subject to any disclaimer, the term of this patent is extended or adjusted under 35 U.S.C. 154(b) by 14 days.

(21) Appl. No.: 17/377,906

(22) Filed: Jul. 16, 2021

(65) Prior Publication Data

US 2022/0016439 A1 Jan. 20, 2022

Related U.S. Application Data

(60) Provisional application No. 63/176,722, filed on Apr. 19, 2021, provisional application No. 63/052,625, filed on Jul. 16, 2020.

(51) Int. Cl.
*A61N 5/06* (2006.01)
*A61B 17/00* (2006.01)
(Continued)

(52) U.S. Cl.
CPC .......... *A61N 5/0624* (2013.01); *A61F 9/0061* (2013.01); *A61F 9/0079* (2013.01); *A61N 5/022* (2013.01); *A61N 7/00* (2013.01); *A61B 2017/00084* (2013.01); *A61B 17/0231* (2013.01); *A61N 2005/0612* (2013.01);
(Continued)

(58) Field of Classification Search
CPC ........ A61N 5/0624; A61N 5/022; A61N 7/00; A61N 2005/0612; A61N 2005/0659; A61N 2005/0661; A61N 2007/0004; A61N 5/067; A61N 5/04; A61N 2005/0654; A61N 2005/0626; A61N 2005/063; A61N 2005/0643; A61N 2005/0644; A61N 2005/0648; A61N 2005/0651; A61N 2005/0652; A61F 9/0061; A61F 9/0079; A61F 2007/0071; A61F 2007/0004; A61F 2007/0088; A61B 17/0231; A61B 2017/00084; A61B 2018/00791; A61B 2090/061; A61B 2090/065; A61L 2/025;
(Continued)

(56) References Cited

U.S. PATENT DOCUMENTS 7,461,658 B2 12/2008 Jones et al.
8,620,451 B2 12/2013 Kennedy
(Continued)

FOREIGN PATENT DOCUMENTS

CN 110420394 A 11/2019
EP 1986742 B1 8/2014
(Continued)

OTHER PUBLICATIONS

International Search Report and Written Opinion for International Application No. PCT/EP2021/070000, mailed Jan. 10, 2022 (30 pages).

*Primary Examiner* — Hien N Nguyen
(74) *Attorney, Agent, or Firm* — Clark+Elbing LLP

(57) ABSTRACT

The present invention features devices, systems, and methods of use thereof for delivering therapeutic or sterilizing ultraviolet (UV) radiation, such as UVC or UVA radiation.

12 Claims, 28 Drawing Sheets

(51) Int. Cl.

| | |
|---|---|
| ***A61B 17/02*** | (2006.01) |
| ***A61F 9/00*** | (2006.01) |
| ***A61F 9/007*** | (2006.01) |
| ***A61N 5/02*** | (2006.01) |
| ***A61N 7/00*** | (2006.01) |

(52) U.S. Cl.
CPC ................. *A61N 2005/0659* (2013.01); *A61N 2005/0661* (2013.01); *A61N 2007/0004* (2013.01)

(58) Field of Classification Search
CPC ........ A61L 2/085; A61L 2/10; A61L 2202/14; A61L 2202/24; G02C 7/04
See application file for complete search history.

(56) References Cited

U.S. PATENT DOCUMENTS

| | | | | |
|---|---|---|---|---|
| 9,024,276 | B2 | 5/2015 | Pugh et al. | |
| 9,474,811 | B2 | 10/2016 | Sharma | |
| 2007/0269008 | A1* | 11/2007 | Pomper ................ | A61N 5/1007 378/65 |
| 2008/0081999 | A1 | 4/2008 | Gravely et al. | |
| 2011/0288617 | A1 | 11/2011 | Sharma | |
| 2012/0041358 | A1* | 2/2012 | Mann .................. | A61F 9/00763 604/22 |
| 2012/0043910 | A1* | 2/2012 | Nagashima ............ | H05B 45/20 315/294 |
| 2013/0162796 | A1* | 6/2013 | Bharara ................. | A61B 5/015 348/77 |
| 2014/0128852 | A1* | 5/2014 | Gooding ................. | A61F 9/009 606/4 |
| 2014/0276248 | A1 | 9/2014 | Hall et al. | |
| 2016/0041406 | A1* | 2/2016 | Ramirez Flores . | G02B 27/0093 700/282 |
| 2017/0304472 | A1 | 10/2017 | Neister et al. | |
| 2018/0146520 | A1 | 5/2018 | Williams | |
| 2018/0353629 | A9 | 12/2018 | Neister et al. | |
| 2019/0030356 | A1 | 1/2019 | Schwarz | |
| 2019/0030359 | A1 | 1/2019 | Dijkstra et al. | |
| 2019/0046812 | A1 | 2/2019 | Harlan et al. | |
| 2019/0091065 | A1 | 3/2019 | Kelleher et al. | |
| 2019/0175401 | A1 | 6/2019 | Van Valen et al. | |
| 2019/0246463 | A1 | 8/2019 | Williams et al. | |
| 2019/0262626 | A1 | 8/2019 | De Taboada et al. | |
| 2019/0299016 | A1 | 10/2019 | Altman | |
| 2019/0314198 | A1* | 10/2019 | Ivri ......................... | A61P 31/00 |
| 2020/0030469 | A1 | 1/2020 | Neister et al. | |
| 2020/0069468 | A1 | 3/2020 | Litherland et al. | |
| 2020/0086137 | A1 | 3/2020 | Yoo et al. | |
| 2020/0179728 | A1 | 6/2020 | Gertner et al. | |
| 2021/0346554 | A1* | 11/2021 | Behzadi .................. | A61L 9/046 |

FOREIGN PATENT DOCUMENTS

| | | | |
|---|---|---|---|
| JP | 2010-501245 | A | 1/2010 |
| KR | 100787874 | B1 | 12/2007 |
| WO | WO-2015/076597 | A1 | 5/2015 |
| WO | WO-2016/070134 | A1 | 5/2016 |
| WO | WO-2022/013435 | A2 | 1/2022 |

* cited by examiner

Internal view

Vitreous probe opening Ø1 mm

Vitreous probe

LED
Distal end
Light guide
40 mm
Proximal end
15 mm

LED

Distal end
LED
Proximal end

Head component
Power button
Base component
LED

UV RADIATION DEVICES AND METHODS OF USE THEREOF

BACKGROUND OF THE INVENTION

Ultraviolet (UV) radiation of suitable intensity, energy, and wavelength can be used to deactivate or kill undesirable cells or microorganisms without significantly causing damage to surrounding healthy cells. However, delivering UV radiation to the appropriate site at the appropriate time has proven a challenging endeavor. Accordingly, new devices and methods are needed for delivering UV radiation for a plurality of indications.

SUMMARY OF THE INVENTION

Described herein are devices, methods, and systems useful for delivering therapeutic and sterilizing ultraviolet (UV) radiation. Additionally, infrared radiation, heat, and ultrasound are optionally delivered using the devices described herein in configurations for treating various diseases. The devices, methods, and systems described are configured to sterilize tissues as well as surfaces such as contact lenses and eyeglasses.

Accordingly, in one aspect, the invention features a therapeutic device including a base component and a head component, the head component having a distal portion and a proximal portion, the distal portion of the head component configured to contact an eyelid of a subject, and the proximal portion of the head component configured to be attached to the base component. The distal portion of the head component can be configured to deliver a therapeutic dose of energy from a plurality of energy sources including a source of ultraviolet C (UVC) radiation, a source of infrared (IR) radiation, and a source of ultrasound. The plurality of energy sources can be configured to deliver the therapeutic dose of energy to the eyelid of the subject at a predetermined power when the distal portion of the head component contacts the eyelid.

In some embodiments, the device further includes a temperature sensor. The device can further include a source of heat. The source of IR radiation can be configured to provide heat. In some embodiments, the source of heat includes a resistance wire element. In some embodiments, the device further includes a source of microwave radiation. In some embodiments, the device further includes a source of intense pulsed light. In some embodiments, the device further includes a contact sensor that senses contact of the device with the eyelid.

In another aspect, the invention features a therapeutic device including a base component and a head component, the head component having a distal portion and a proximal portion, the distal portion of the head component configured to deliver a therapeutic dose of UVC radiation to an eye of a subject from a source of UVC radiation, and the proximal portion of the head component configured to be attached to the base component. The device can further include proximity determining element configured to detect a predetermined distance between the source of UVC radiation and a site of treatment of the eye. The device can also include a signal-generating element configured to generate a signal upon detection of the predetermined distance by the proximity determining element, wherein the signal is configured to activate the source of UVC radiation to deliver the therapeutic dose of UVC radiation to the eye of the subject at a predetermined power. The therapeutic device can further include a light guide having a proximal portion and a distal portion, the proximal portion of the light guide configured to attach to the distal portion of the head component, and the distal portion of the light guide configured to deliver the therapeutic dose of UVC radiation.

In another aspect, the invention features a disinfecting device including a base component and a head component, the head component having a distal portion and a proximal portion, the distal portion of the head component configured to deliver a disinfecting dose of UVC radiation to a subject from a source of UVC radiation, and the proximal portion of the head component configured to be attached to the base component. The device can further include a light guide having a proximal portion and a distal portion, the proximal portion of the light guide configured to attach to the distal portion of the head component, and the distal portion of the light guide configured to deliver the disinfecting dose of UVC radiation. The device can also include proximity determining element configured to detect a predetermined distance between the distal portion of the light guide and a site of treatment of the subject. The device can also include a signal-generating element configured to generate a signal upon detection of the predetermined distance by the proximity determining element, wherein the signal is configured to activate the source of UVC radiation to deliver the disinfecting dose via the light guide at a predetermined power.

In some embodiments, the head component includes an aperture control element configured to modulate the dose of UVC radiation. The aperture control element can include one or more removable cones. The aperture control element can be integral within the head component. An aperture of the source of UVC radiation can be from about 1 mm to about 50 mm (e.g., from about 2 mm to about 40 mm, from about 4 mm to about 40 mm, e.g., about 25 mm, e.g., about 4 mm).

In some embodiments of any of the above aspects, the source of UVC radiation is configured to deliver the therapeutic dose of UVC to an anterior region, a posterior region, a vitreous chamber region, a retinal region, a choroidal region, a macular region, a lens region (e.g., an intraocular lens region), a ciliary muscle region, an optic nerve region, an injury site, or a site affected by a foreign object of the eye. In some embodiments, the therapeutic dose of UVC is configured for delivery to the eye of the subject through a vitrectomy element. In some embodiments, the source of UVC radiation is configured to deliver the therapeutic dose of UVC radiation to an interior region of the eye of the subject through a light guide configured to insert into the vitrectomy element and enter the interior region of the eye of the subject.

In some embodiments of any of the above aspects, the source of UVC radiation is configured to deliver the therapeutic dose of UVC to a wound. In some embodiments, the therapeutic dose of UVC improves wound healing (e.g., speed of healing, degree of healing, and/or reduction of scarring).

In some embodiments of any of the above aspects, the device includes an eye stabilizing element that includes a proximal end configured to attach to the distal portion of the head component and a distal end configured to contact and stabilize the eye. In some embodiments, the eye stabilizing element is shaped as a cone having a first diameter at the proximal end and a second diameter at the distal end. In some embodiments, the first diameter is smaller than the second diameter, or the first diameter is larger to the second diameter. In some embodiments, the distal portion of the eye stabilizing element includes a plurality of teeth configured to secure the eye of the subject. In some embodiments, the eye stabilizing element is composed of a material that is not transparent to UVC light. In some embodiments, the eye stabilizing element is substantially hollow to provide a volume through which a therapeutic dose of UVC radiation from the head component can travel to a treatment site of the eye of the subject. In some embodiments, the eye stabilizing element is configured to block UVC radiation from irradiating a healthy site of the eye of the subject. In some embodiments, the eye stabilizing element is disposable. In some embodiments, the eye stabilizing element is for single-use only and includes a tag (e.g., radio frequency identification (RFID)) to prevent reuse of the eye stabilizing element. In some embodiments, the eye stabilizing element is not sterilizable. In some embodiments, the eye stabilizing element is composed of plastic. In some embodiments, the eye stabilizing element is transparent to visible light.

In another aspect, the invention features a therapeutic device including a base component and a head component, the head component having a distal portion and a proximal portion, the distal portion of the head component configured to deliver a therapeutic dose of ultraviolet A (UVA) radiation to an eye of subject from a source of UVA radiation, and the proximal portion of the head component configured to be attached to the base component. The device can further include a proximity determining element configured to detect a predetermined distance between the source of UVA radiation and a site of treatment of a subject. The device can also include a signal-generating element configured to generate a signal upon detection of the predetermined distance by the proximity determining element, wherein the signal is configured to activate the source of UVA radiation to deliver the therapeutic dose of UVA radiation to the eye of the subject at a predetermined power.

In some embodiments, the device further includes an imaging module configured to display an image of the site of treatment.

In some embodiments, the device is configured to be mounted on a slit lamp.

In some embodiments, the device further includes a power source (e.g., a battery)

In some embodiments, the device further includes a control mechanism, e.g., a control button. In some embodiments the control mechanism is on the base component.

In some embodiments, the proximity determining element includes two or more lasers. The proximity determining element can be configured to activate the signal-generating element upon convergence of the two or more lasers.

In some embodiments, the signal-generating element is configured to provide an auditory, visual, or tactile signal.

In another aspect, the invention features a device that includes a base component and a head component, the head component having a distal portion and a proximal portion, the distal portion of the head component configured to deliver a dose of UVC radiation to a contact lens or eyeglasses from a source of UVC radiation, and the proximal portion of the head component configured to be attached to the base component. In some embodiments, the device further includes a contact lens or eyeglasses case including a source of ultrasound, wherein the contact lens or eyeglasses case is attached to the distal portion of the head component and configured to deliver a dose of ultrasound.

In another aspect, the invention features a system for delivering a plurality of energy sources to a tissue site. The system includes a base component, the base component having a proximal portion and a distal portion, the distal portion configured to mate with one of a plurality of interchangeable heads selected from two or more of a first head including a source of UVC radiation; a second head including a source of IR radiation; a third head including a source of ultrasound; a fourth head including a source of UVA radiation; a fifth head including a source of UVC radiation, a source of IR radiation, and a source of ultrasound; and a sixth head that includes a source of microwave radiation and a source of intense pulsed light. The first head can further include one or more of a proximity determining element configured to detect a predetermined distance between the energy source and a site of administration, a signal generating element configured to generate a signal upon detection of the predetermined distance by the proximity determining element, a module for aperture control to modulate the dose of energy, a light guide, and an imaging module. In some embodiments, wherein the system for delivering a plurality of energy sources to a tissue site includes a source of microwave radiation and a source of intense pulsed light, the UVC radiation, IR radiation, ultrasound, microwave radiation, and intense pulsed light can be administered simultaneously. In some embodiments, wherein the system for delivering a plurality of energy sources to a tissue site includes a source of microwave radiation and a source of intense pulsed light, the UVC radiation, IR radiation, ultrasound, microwave radiation, and intense pulsed light can be administered sequentially.

In some embodiments of any of the above aspects, the source of UVC radiation includes an LED. In some embodiments, the source of UVC radiation include a plurality of LEDs. In some embodiments, the UVC radiation includes a peak wavelength from about 100 nm to about 290 nm (e.g., from about 200 nm to about 290 nm, e.g., from about 220 nm to about 290 nm, e.g., from about 240 nm to about 280 nm, e.g., from about 250 nm to about 280 or from about 260 nm to about 280 nm, e.g., about 254 nm, about 265 nm, or about 275 nm). In some embodiments, the UVC radiation has a radiation intensity of from about 20 mW/cm$^2$ to about 1,000 mW/cm$^2$.

In some embodiments of any of the above aspects, the source of UVA radiation includes an LED. In some embodiments, the source of UVA radiation includes a plurality (e.g., 1, 2, 3, 4, 5, 6, 7, 8, 9, 10, or more) of LEDs. The UVA radiation can have a wavelength of from about 315 nm to about 400 nm, e.g., about 365 nm or about 370 nm. In some embodiments, the UVA radiation has a radiation intensity of from about 0.5 mW/cm$^2$ to about 100 mW/cm$^2$, e.g., from about 1 mW/cm$^2$ to about 90 mW/cm$^2$, from about 2 mW/cm$^2$ to about 80 mW/cm$^2$, from about 5 mW/cm$^2$ to about 70 mW/cm$^2$, from about 10 mW/cm$^2$ to about 60 mW/cm$^2$, from about 15 mW/cm$^2$ to about 50 mW/cm$^2$, from about 20 mW/cm$^2$ to about 45 mW/cm$^2$, from about 25 mW/cm$^2$ to about 35 mW/cm$^2$. In some embodiments, the head component further includes an aperture control element configured to modulate the dose of UVA radiation.

In some embodiments, the source of IR radiation includes an LED. The source of IR radiation can include a plurality of LEDs. The IR radiation includes a peak wavelength from about 750 nm to about 1,000,000 nm. The IR radiation can have a radiation intensity of from about 20 mW/cm$^2$ to about 1,000 mW/cm$^2$.

In some embodiments, the ultrasound has a frequency of from about 1 MHz to about 10 MHz.

In some embodiments of any of the above aspects, the head component and base component are integral.

In some embodiments of any of the above aspects, the head component and the base component are separable.

In another aspect, the invention features a method for treating blepharitis or meibomian gland disease (MGD) by providing a device as described herein, allowing the distal portion of the head component to contact the eyelid, and administering to the eyelid the therapeutic dose of energy from the plurality of energy sources.

In some embodiments, the UVC radiation, IR radiation, ultrasound, microwave radiation, and intense pulsed light can be administered simultaneously. Alternatively, in some embodiments, the UVC radiation, IR radiation, ultrasound, microwave radiation, and intense pulsed light can be administered sequentially.

In some embodiments, the method further includes delivering heat.

In another aspect, the invention features a method for treating an eye infection (e.g., endophthalmitis), a cancer (e.g., an eyelid cancer or an ocular cancer) by providing a device as described herein and positioning the device in proximity to the site of treatment. The method can include detecting the predetermined distance by the proximity determining element, generating the signal by the signal generating element to activate the source of UVC radiation, and administering the therapeutic dose of UVC radiation to the site of treatment of the eyelid or of the eye.

In another aspect, the invention features a method of treating cancer by providing a device as described herein and positioning the device in proximity to the site of treatment, detecting the predetermined distance by the proximity determining element, generating the signal by the signal generating element to activate the source of UVC radiation, and administering the therapeutic dose of UVC radiation to the site of treatment.

In some embodiments, the cancer is an eyelid or ocular cancer. In some embodiments, the cancer is intraocular melanoma, retinoblastoma, uveal melanoma, conjunctival melanoma, orbital cancer, or adnexal cancer.

In some embodiments of any of the aspects described herein, the devices and methods may be used to treat a caner, neoplasia, and/or dysplasia, e.g., including cancerous or precancerous cells.

In another aspect, the invention features a method for disinfecting a tissue of a subject by providing a device as described herein and positioning the light guide in proximity to the site of treatment. The method can include detecting the predetermined distance by the proximity determining element, generating the signal by the signal generating element to activate the source of UVC radiation, and administering the therapeutic dose of UVC radiation to the site of treatment in the tissue of the subject via the light guide.

In some embodiments, the tissue is selected from an eye, nasal cavity, oral cavity, skin tissue, and a lumen. In some embodiment, the subject has, or is suspected of having, a bacterial infection (e.g., *Chlamydia trachomatis, Streptococcus pneumoniae, Haemophilus influenzae*), fungal infection, amoebic infection, parasitic infection (e.g., *toxocara, toxoplasma*, infectious retinitis), or viral infection (e.g., a respiratory infection such as respiratory syncytial virus, influenza virus, or SARS-CoV2. In some embodiments, the subject has acne vulgaris and/or acne rosacea. In some embodiments, the subject has an ulcer, e.g., caused by *H. pylori*. In some embodiments the subject has, or is suspected of having, a herpes virus infection. In some embodiments the subject has, or is suspected of having, a human immunodeficiency virus infection. In some embodiments the herpes virus infection is located on an epithelial tissue e.g., a genital tissue, lips, or other parts of the skin. In some embodiments, the subject has, or is suspected of having, a human papilloma virus infection. In some embodiments, the human papilloma virus infection is located on a tissue of a cervix.

In another aspect, the invention features a method for treating corneal ectasia (e.g., keratoconus) in a subject by providing a device as described herein and positioning the device in proximity to the site of treatment, wherein the subject has been administered a dose of a photoactivator. Suitable photoactivators include, but are not limited to, riboflavin, Rose Bengal, porphyrin-based photosensitizers, psoralens, quinones, anthracyclins, anthracenediones, xanthenes, fluoresceins, rhodamines, phthaleins, cyanines, chalcogenapyrylium dyes, triarylmethane dyes, phenothiazines, phenoxazines, acridines, hypericin, nicotinamide adenine dinucleotide phosphate (NADPH), 5-aminolevulinic acid, ciprofloxacin, and quinine. The photoactivator may be administered at the site of treatment. In some embodiments, the method includes detecting the predetermined distance by the proximity determining element, generating the signal by the signal generating element to activate the source of UVA radiation, and administering the therapeutic dose of UVA radiation to the site of treatment in the eye.

In another aspect, the invention features a method for sterilizing a contact lens or eyeglasses including providing a device as described herein, placing the contact lens or eyeglasses in the case, and administering the source of UVC radiation and ultrasound to the contact lens or eyeglasses. In some embodiments, the UVC radiation and ultrasound are administered simultaneously. In some embodiments, the UVC radiation and ultrasound are administered sequentially.

In another aspect, the invention features a contact lens, having a proximal end and a distal end, configured to direct a therapeutic dose of UVC radiation from a source of UVC radiation towards an eye of a subject. In some embodiments, the contact lens includes the source of UVC radiation. In some embodiments, the source of UVC radiation includes an LED. In some embodiments, the source of UVC radiation includes a plurality (e.g., 1, 2, 3, 4, 5, 6, 7, 8, 9, 10, or more) of LEDs. In some embodiments, the source of UVC radiation includes a plurality of surface mounted device (SMD) LEDs. In some embodiments, the plurality of LEDs is configured to attach to the contact lens, configured to be incorporated within the lens, or configured to be focused through the lens. In some embodiments, the proximal end of the contact lens is configured to contact the eye of the subject and wherein the distal end is configured to mate to an external source of UVC radiation. In some embodiments, the external source of UVC radiation transmits the therapeutic dose of UVC to the distal end of the contact lens through a light guide. In some embodiments, the UVC radiation includes a peak wavelength from about 100 nm to about 290 nm (e.g., from about 200 nm to about 290 nm, e.g., from about 220 nm to about 290 nm, e.g., from about 240 nm to about 280 nm, e.g., from about 250 nm to about 280 or from about 260 nm to about 280 nm, e.g., about 254 nm, about 265 nm, or about 275 nm). In some embodiments, the UVC radiation has a radiation intensity of from about 20 $mW/cm^2$ to about 1,000 $mW/cm^2$. In some embodiments, the contact lens includes a power source that is a battery, an energy transfer antenna, a solar cell, an inertia power harvester, or an electrical plug.

In another aspect, the invention features a method for treating an eye infection including providing the contact lens having a source of UVC radiation as described herein, positioning the contact lens on the site of the eye infection and administering a therapeutic dose of UVC radiation to the site of treatment of the eyelid or the of the eye.

In another aspect, the invention features a method of treating a wound of a subject including providing the therapeutic device herein described and administering a therapeutic dose of UVC radiation to the wound.

Definitions

To facilitate the understanding of this invention, a number of terms are defined below. Terms defined herein have meanings as commonly understood by a person of ordinary skill in the areas relevant to the invention. Terms such as "a", "an," and "the" are not intended to refer to only a singular entity but include the general class of which a specific example can be used for illustration. The terminology herein is used to describe specific embodiments of the invention, but their usage does not limit the invention, except as outlined in the claims.

As used herein, the term "about" refers to a value that is within 10% above or below the value being described.

The term "cancer," as used herein, refers to diseases caused by uncontrolled cell division and the ability of cells to metastasize, or to establish new growth in additional sites. The term cancer includes, for example, leukemias, seminomas, melanomas, teratomas, lymphomas, neuroblastomas, gliomas, rectal cancer, endometrial cancer, kidney cancer, adrenal cancer, thyroid cancer, blood cancer, skin cancer, brain cancer, cervical cancer, intestinal cancer, liver cancer, colon cancer, stomach cancer, intestine cancer, head and neck cancer, gastrointestinal cancer, lymph node cancer, esophageal cancer, colorectal cancer, pancreatic cancer, ear, nose and throat cancer (ENT), breast cancer, prostate cancer, uterine cancer, ovarian cancer, and lung cancer and their metastases. Examples thereof are lung carcinomas, breast carcinomas, prostate carcinomas, colon carcinomas, renal cell carcinomas, cervical carcinomas, or metastases from the types of cancer or tumors described above. The term cancer according to the invention also encompasses cancer metastases and/or cancers of surrounding tissue e.g., orbital or adnexal cancers. As used herein, cancer also includes neoplasia and dysplasia, e.g., including cancerous and precancerous cells or tissues.

The term "disinfecting dose of energy," as used herein, refers to the amount of electromagnetic energy (e.g., UV), mechanical energy (e.g., ultrasonic energy), thermal energy, or any combinations thereof that is suitable to achieve an intended disinfecting effect when used in an appropriate treatment regimen, for example, to reduce the microbial load (e.g., bacterial load, fungal, protozoal, parasitic, or viral load) on a target site.

As used herein, the term "energy guide" refers to any element capable of carrying energy of any kind (e.g., electromagnetic energy, mechanical energy, thermal energy) from one end to another. In one embodiment a light guide can be an optical fiber. Well-known optical fibers include those made of fused silica, pure silica, organosilicons, hollow tubes, clad and unclad fibers where the fibers are either singular or bundled. Optical fibers can also be made of transparent conductive materials, e.g., SrNbO3. Other optical fibers include liquid fibers that are water based or other diluents such as alcohols, ethers, aldehydes, ketones, and other liquids suitable for transmitting effective wavelengths and some can reduce thermal energy including infrared energy.

The term "energy source," as used herein, refers to a source of electromagnetic radiation, mechanical energy (e.g., sound, or ultrasound), thermal energy or any combination thereof. An energy source can include multiple sources and the energy from an energy source can directly be administered to a target site or through an energy guide.

The term "imaging module," as used herein, describes the imaging elements and processing circuitry which is used to produce a video signal.

As used herein, the term "integral" refers to of, relating to, or belonging as a part of the whole device; i.e., necessary to the completeness of the whole; consisting or composed of parts that together constitute a whole.

The term "intense pulse light" or "IPL," as used herein, refers to non-laser light that has various wavelength ranges and is periodically emitted in the form of a strong pulse. IPL, for example, is light in the wavelength range of approximately 300 to 1,200 nm (varies depending on the IPL device) and is periodically emitted in the form of a strong pulse. IPL irradiation equipment uses a lamp flash that emits light at a wavelength of approximately 300-1,200 nm and controls the wavelength of the light emitted by the filter. IPL energy is delivered as a series of single, double, or triple pulse sequences with pulse durations of 2-25 ms and inter-pulse delays of 10-500 ms. IPL radiant energy density can range from 5 $J/cm^2$ to 60 $J/cm^2$.

The term "light guide," as used herein, refers to an article that receives light at an input end and propagates the light to an output end or an extraction mechanism without significant losses. In general, light guides operate on the principle of total internal reflection, whereby light travelling through the light guide is reflected at the surfaces of the light guide based on differences in the indices of refraction of the material of the light guide and the material immediately surrounding the light guide, e.g., air, cladding, etc.

The term "proximity determining element," as used herein, refers to any device capable of measuring distance from a device herein described to the surface of a treatment or administration site.

The term "respiratory infection," as used herein, includes invasion by and/or multiplication and/or colonization of a pathogenic microorganism (e.g., bacteria and viruses) in one or more components of the respiratory tract, such as, for example, lung, epiglottis, trachea, bronchi, bronchioles, or alveoli.

As used herein, the term "separable" refers to a device component, module, element, or any variation thereof that can be easily connected or disconnected by engaging or disengaging the connection at a working interface.

As used herein, the term "signal generating element" refers to a component of a device as described herein hat can provide a detectable signal (e.g., auditory signal, visual cue, haptic feedback) in response to a measured distance value, e.g., as measured by a proximity determining element of a device described herein.

The terms "sterilization" and "disinfection," or variants thereof, as used herein, refer to the reduction of the load of microorganisms (e.g., pathogenic and/or nonpathogenic) on or within a living tissue or part of the body of a subject, or on or within an inanimate object. These terms, as used herein, can be used interchangeably.

As used herein, the term "subject" refers to a mammal, including a human in need of therapy for, or susceptible to, a condition or sequelae. Subjects can include dogs, cats, pigs, cows, sheep, goats, horses, rats, and mice and humans. The term "subject" does not exclude individuals who are normal in all respects.

As used herein, the term "sufficient distance and time" refers to the time period and distance from a target site (e.g., a body part, a surface, or an object) that light or other energy forms (e.g., mechanical, or thermal) produced by the device is exposed to in order to deliver a therapeutic dose of energy. In one embodiment, it is from about 0.01 seconds to about 30 minutes. In one embodiment, a shutter is utilized to open, close, and modulate the passage of energy from the energy source to the target site. The exposure can be directly from the end of an energy source or extended via an energy guide (e.g., light guide) at the end of an energy guide, especially for administering the therapeutic dose of energy into a lumen of a body either directly or through the skin of a subject.

The term "therapeutic dose of energy," as used herein, refers to the amount of electromagnetic energy, mechanical energy (e.g., ultrasonic energy), thermal energy, or a combination thereof that is suitable to achieve an intended therapeutic effect when used in an appropriate treatment regimen, for example, to reduce the severity of symptoms or conditions of a disease. The dose can be considered a therapeutic dose for the treatment of cancer or metastases, if the amount of energy applied is sufficient to lead to the following effects: the growth of the tumor or metastases slows down or stops, or a decrease in the size of the tumor or metastases is found, and/or the patient has a longer life. The dose can be considered a therapeutic dose for the treatment of a bacterial infection, a fungal infection, a protozoal infection, or a viral infection, if the amount of energy applied is sufficient to lead to the following effects: the infection slows down or stops, and/or the patient has a longer life. Appropriate therapeutic doses will generally strike a balance between therapeutic effect and tolerated toxicity, for example, when a side effect and toxicity are tolerated, provided that the therapy is beneficial.

As used herein, the term "treatment" (also "treat" or "treating"), in its broadest sense, refers to any administration of a therapeutic agent (e.g., ultraviolet light) that partially or completely alleviates, ameliorates, relives, inhibits, delays onset of, reduces severity of, or reduces incidence of one or more symptoms, features, or causes of a particular disease, disorder, or condition. In some embodiments, such treatment can be administered to a subject who does not exhibit signs of the relevant disease, disorder or condition or of a subject who exhibits only early signs of the disease, disorder, or condition. Alternatively, or additionally, in some embodiments, treatment can be administered to a subject who exhibits one or more established signs of the relevant disease, disorder or condition. In some embodiments, treatment can be of a subject who has been diagnosed as suffering from the relevant disease, disorder, or condition. In some embodiments, treatment can be of a subject known to have one or more susceptibility factors that are statistically correlated with increased risk of development of the relevant disease, disorder, or condition.

BRIEF DESCRIPTION OF THE DRAWINGS

FIG. 7A shows the ultrasound transducer, FIG. 7B shows the heating element, and FIGS. 7C and 7D show UVC LEDs.

FIG. 26A is a side view and FIG. 26B is a perspective view. The distal end is shown having a diameter of 6 mm and the proximal end is shown to have a diameter of 10 mm.

DETAILED DESCRIPTION OF THE INVENTION

Figure 1:
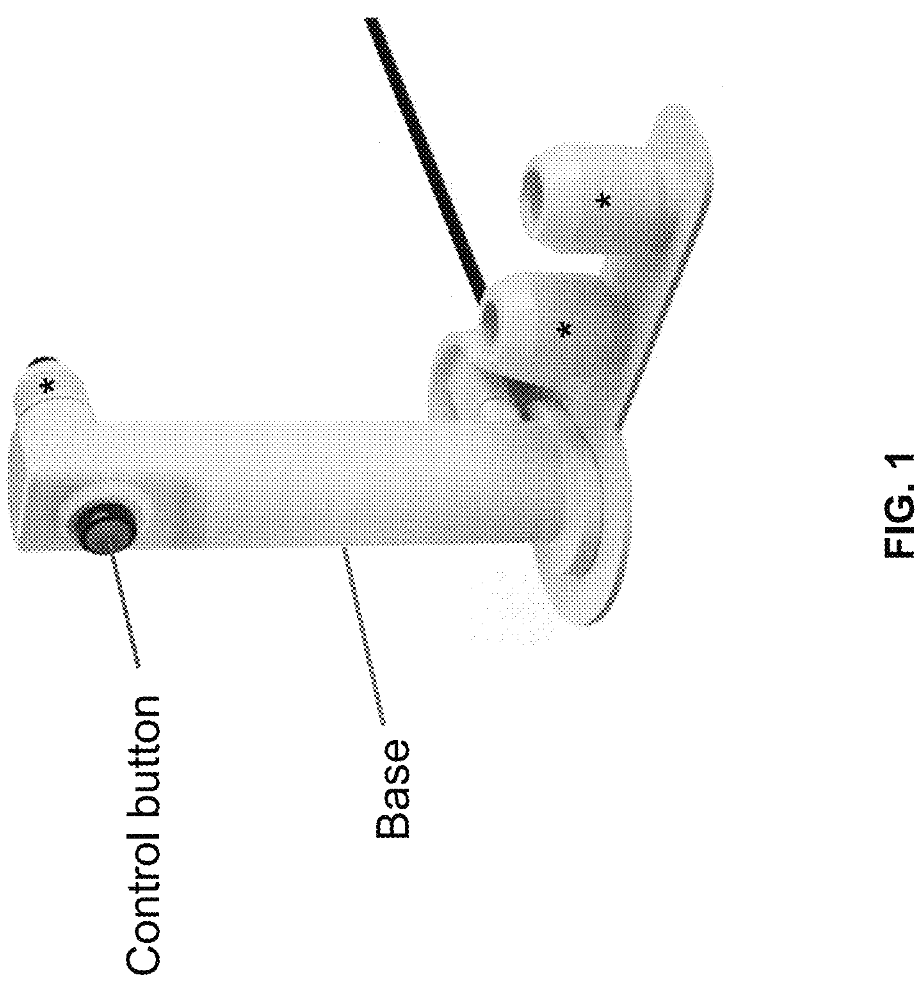
FIG. 1 is a schematic drawing showing the control side of the therapeutic device. The base component, the control button, and the interchangeable head components (indicated by an asterisk) are shown.
Figure 2:
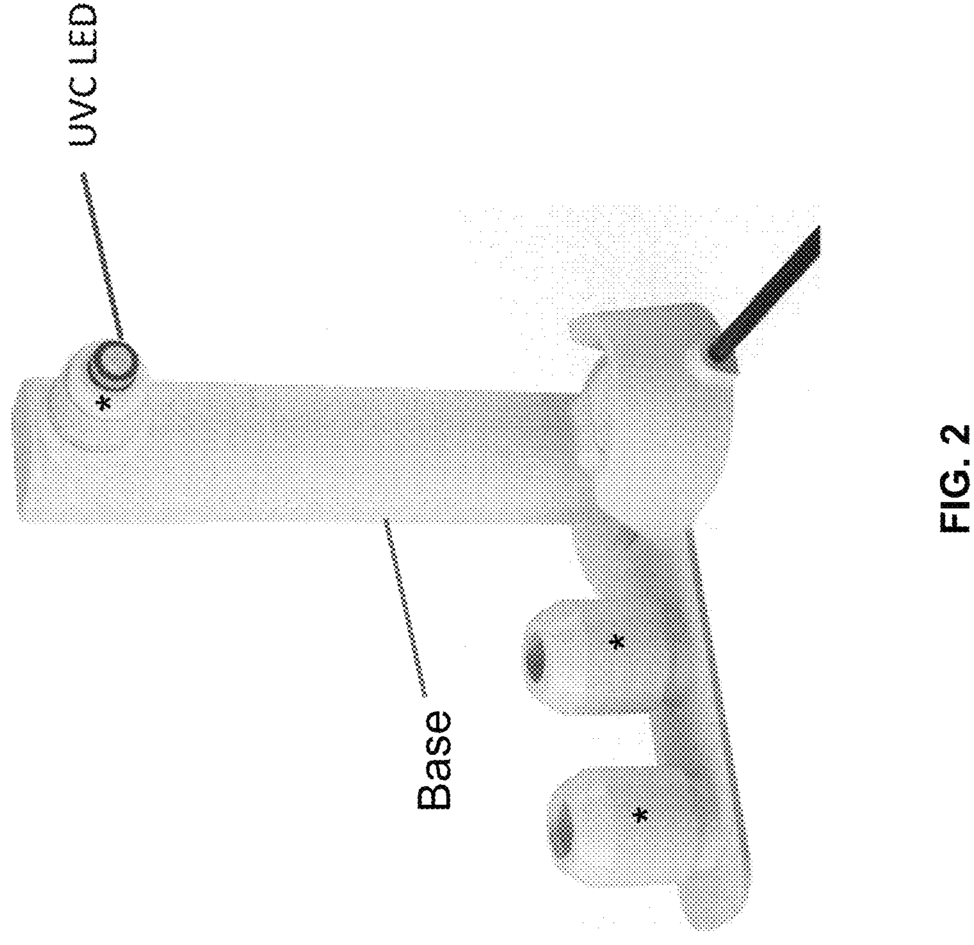
FIG. 2 is a schematic drawing showing the therapeutic side of the therapeutic device. The base component, the UVC LED source, and the interchangeable head components (indicated by an asterisk) are shown.
Figure 3:
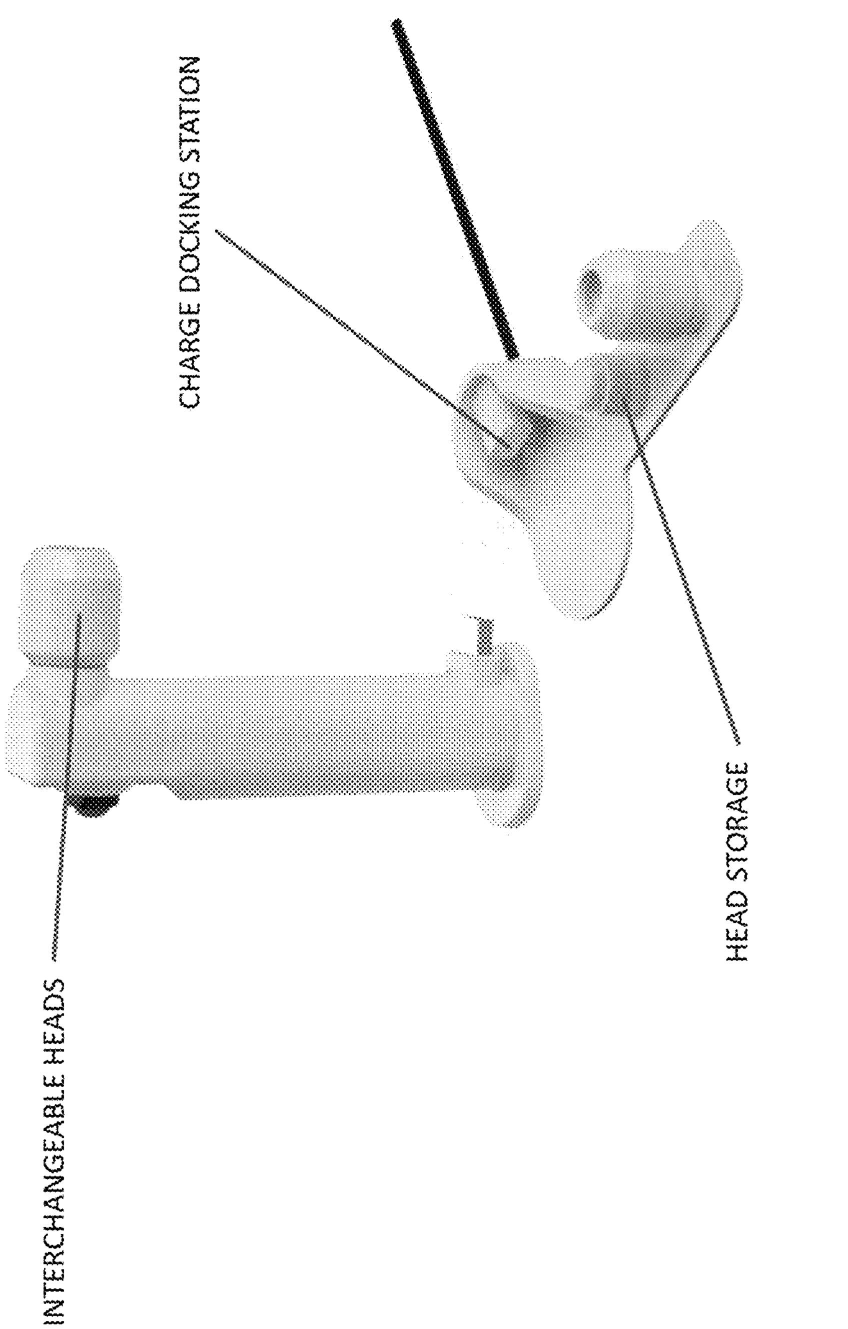
FIG. 3 is a schematic drawing showing a side view of the therapeutic device and charge docking station.
Figure 4:
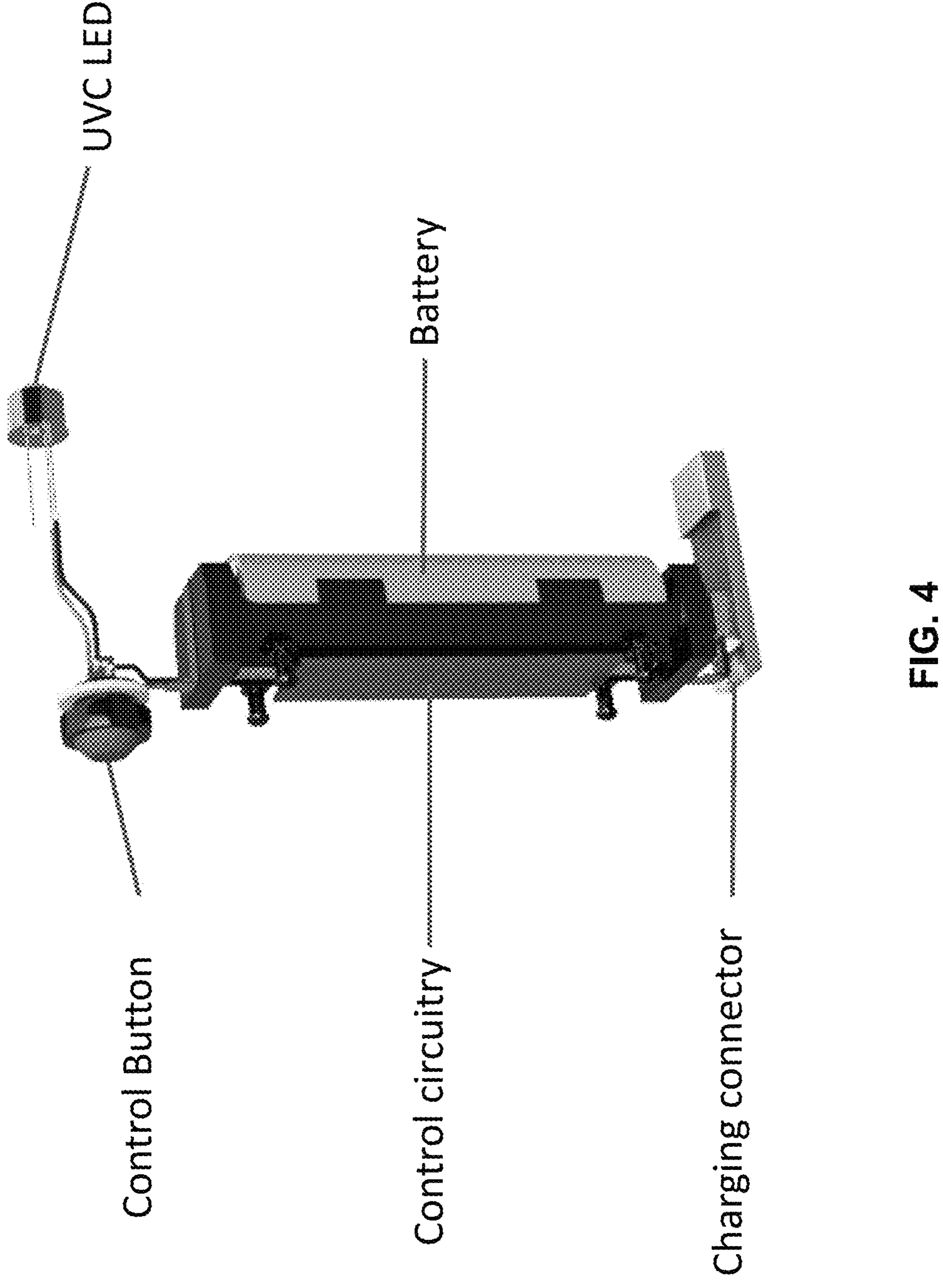
FIG. 4 is a schematic drawing showing the interior components of the therapeutic delivery device. The control button, control circuitry, charging connector, battery, and the UVC LED components are shown.
Figure 5:
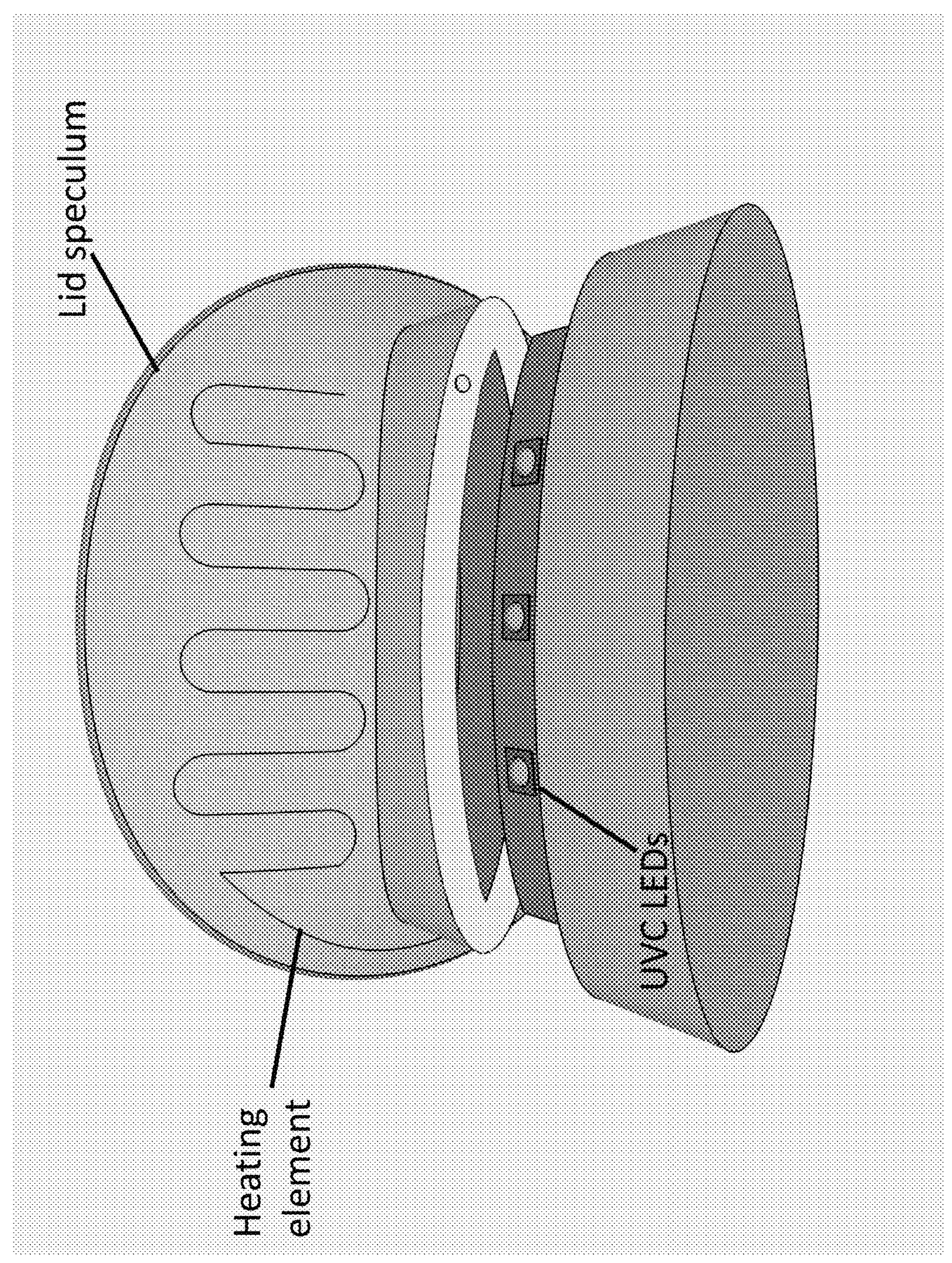
FIG. 5 is a schematic drawing showing an energy delivery head component. Multiple UVC LEDs are depicted and can connect with a module that includes a heating element and a lid speculum.
Figure 6:
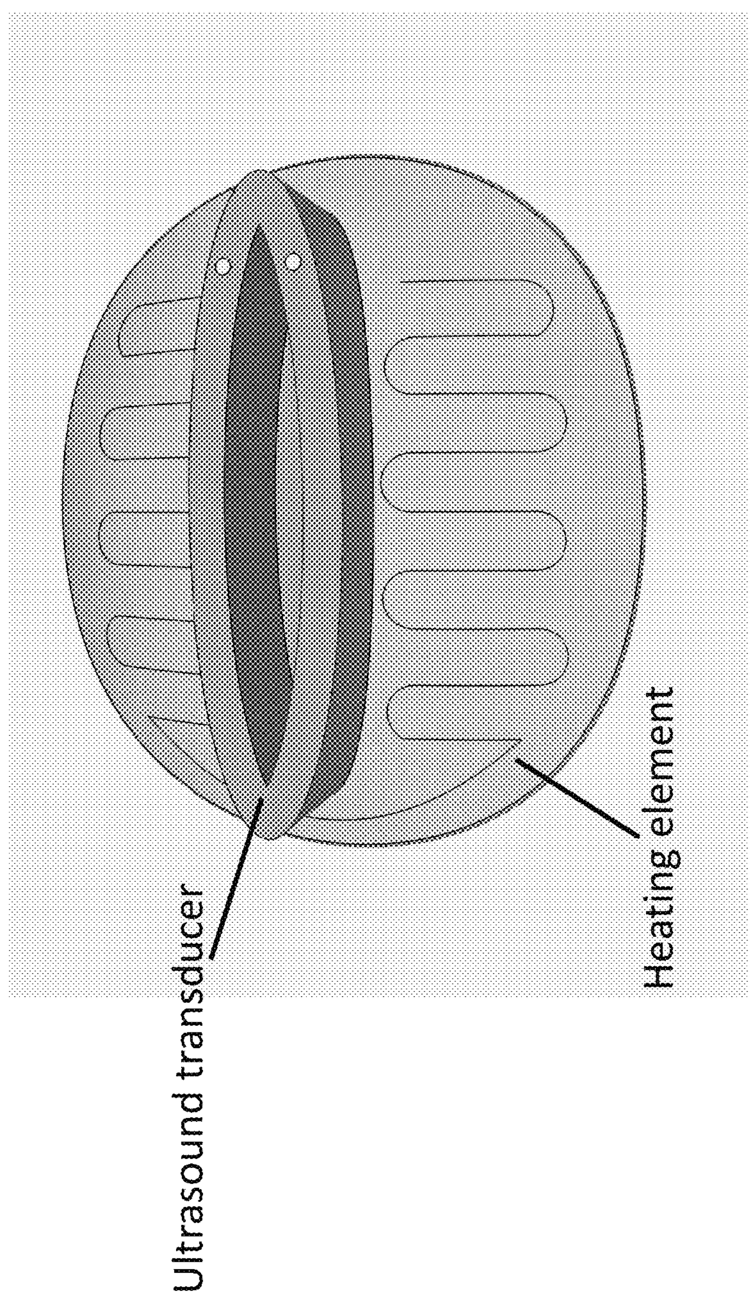
FIG. 6 is a schematic drawing showing an energy delivery head component that is configured with an ultrasound transducer and a heating element.
Figure 7A:
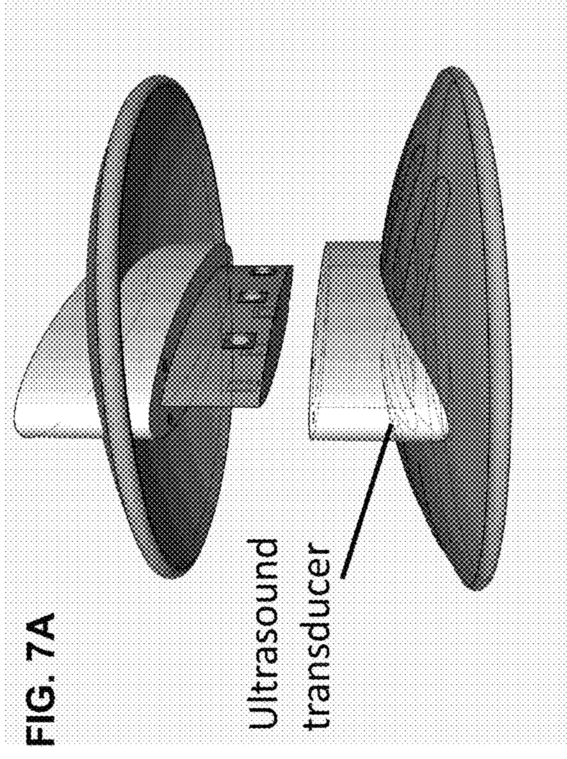
FIGS. 7A-7D are schematic drawings showing multiple views of an energy delivery head module configured to deliver UVC light, ultrasound, and heat.
Figure 7B:
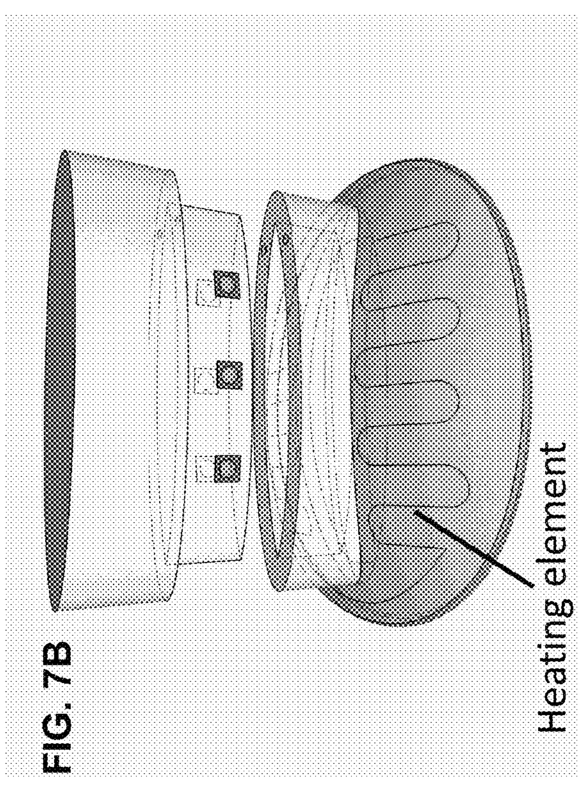
Figure 7C:
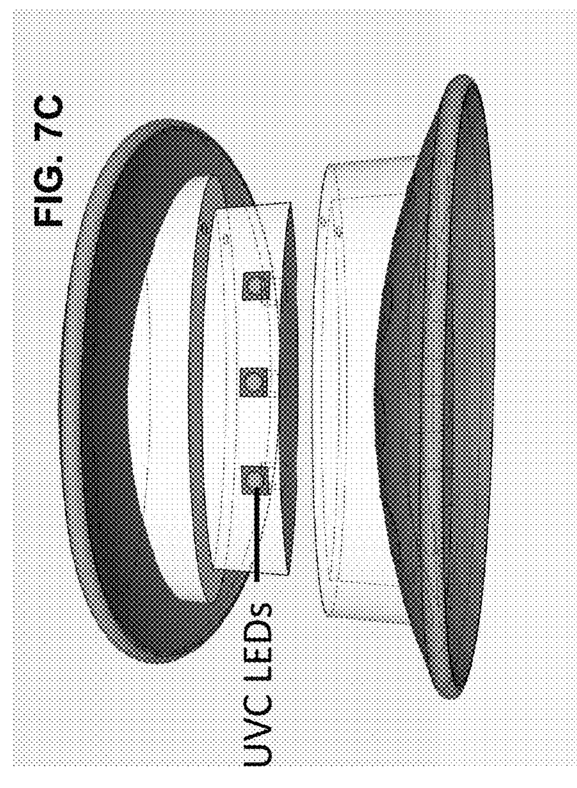
Figure 7D:
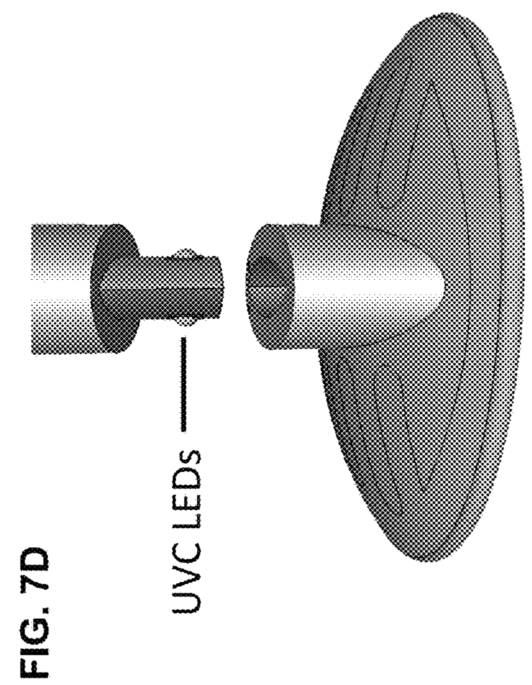
Figure 8:
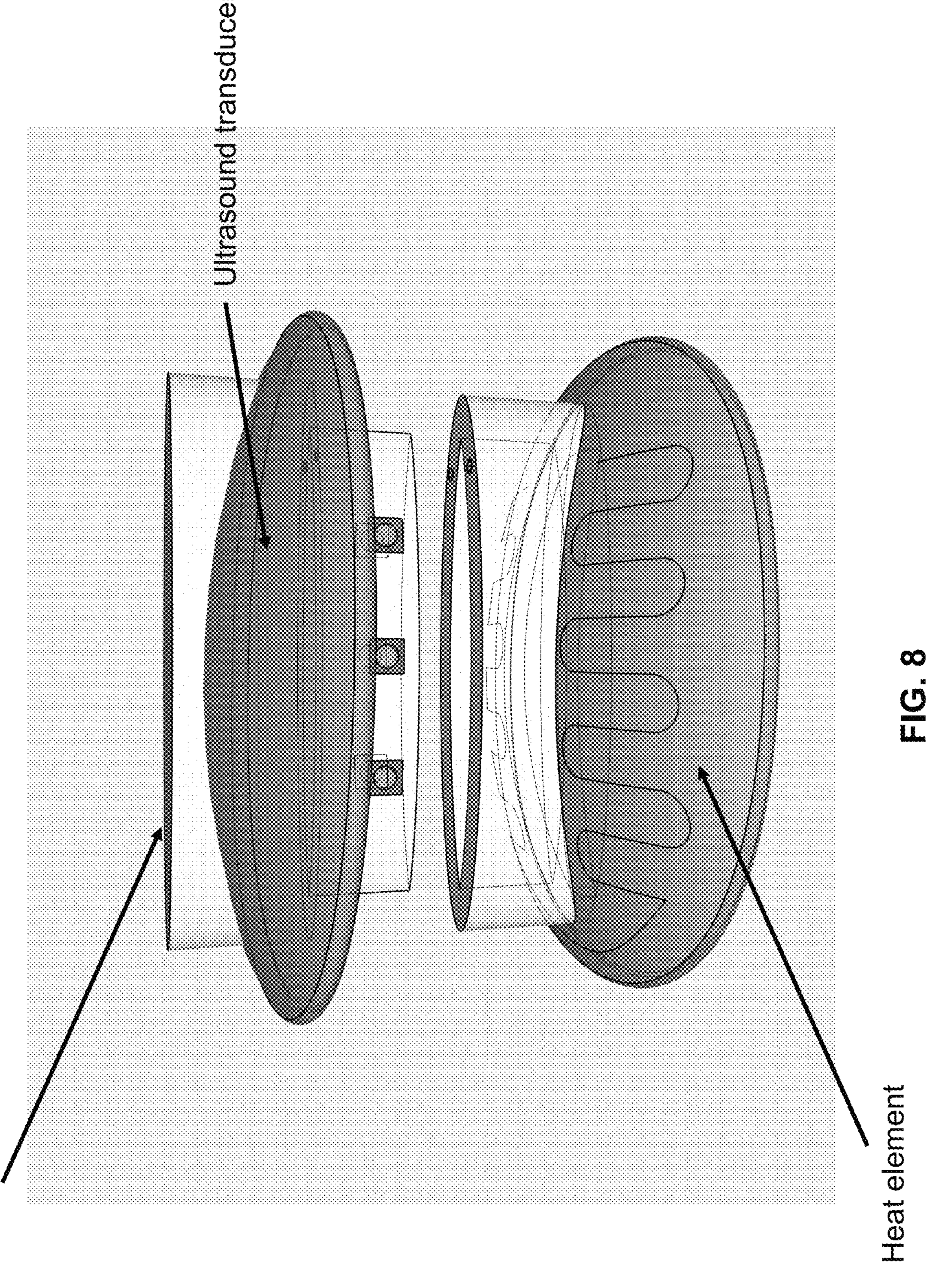
FIG. 8 is a schematic drawing showing an energy delivery head module configured to deliver UVC light, ultrasound, and heat.
Figure 9:
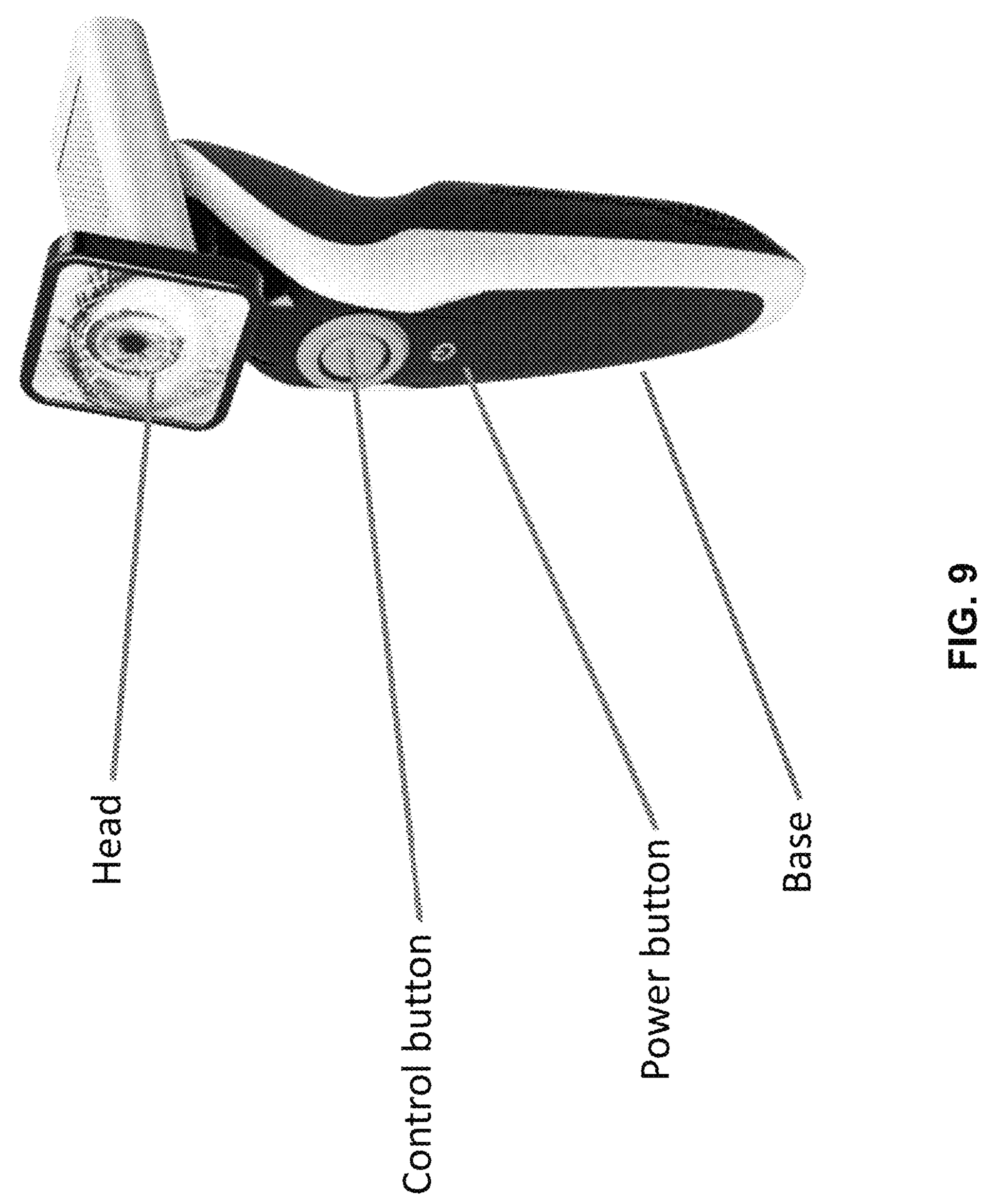
FIG. 9 is a schematic drawing showing the control side of the therapeutic device. The head component, control button, power button, and the base component are shown.
Figure 10:
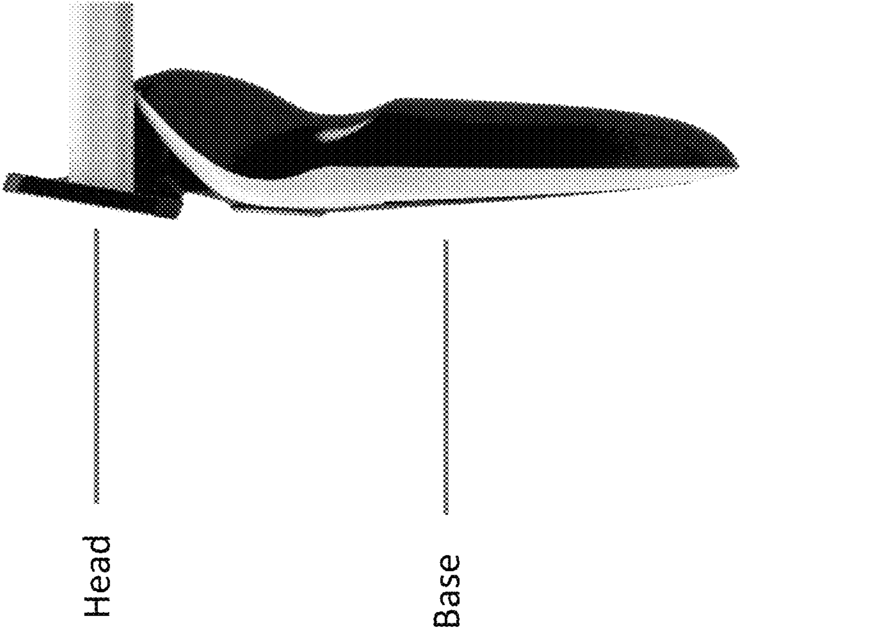
FIG. 10 is a schematic drawing showing a side view of the therapeutic device including a base component and a head component.
Figure 11:
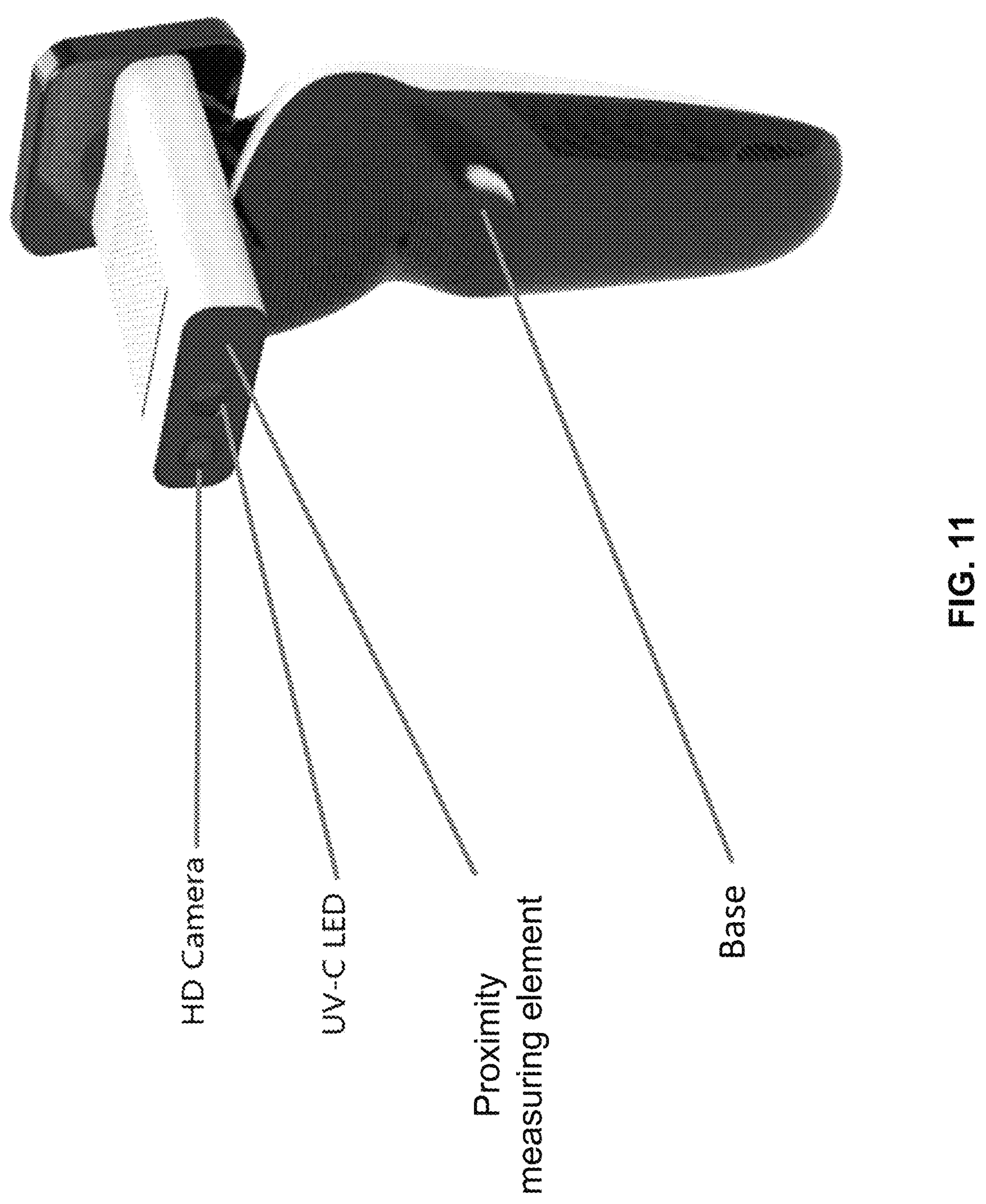
FIG. 11 is a schematic drawing of the therapeutic side of the therapeutic device. The imaging module (HD camera), UVC LED source, proximity measuring element and the base component are shown.
Figure 12:
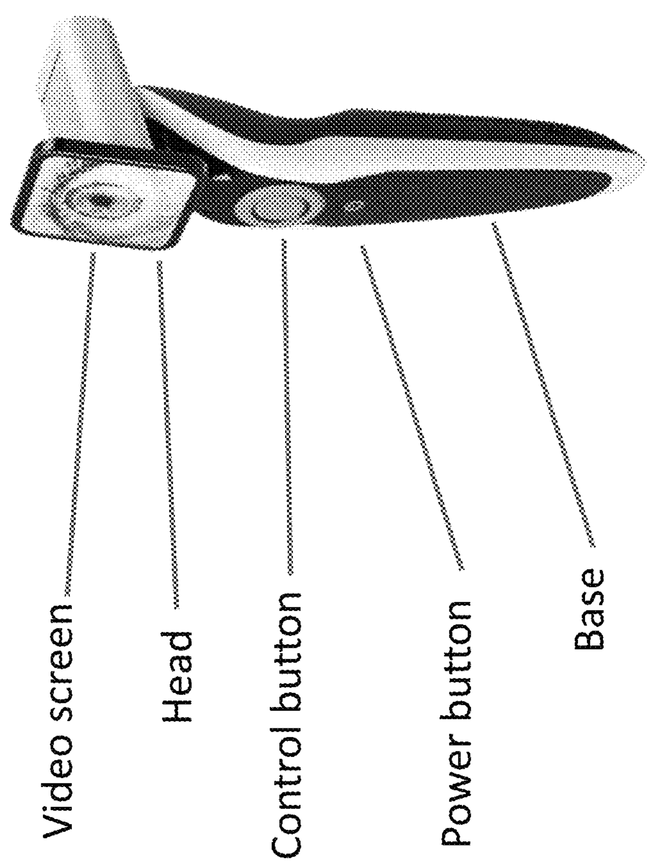
FIG. 12 is a schematic drawing of the control side of the therapeutic device. The video screen, the head module, the control button, the power button, and the base component are shown.
Figure 13:
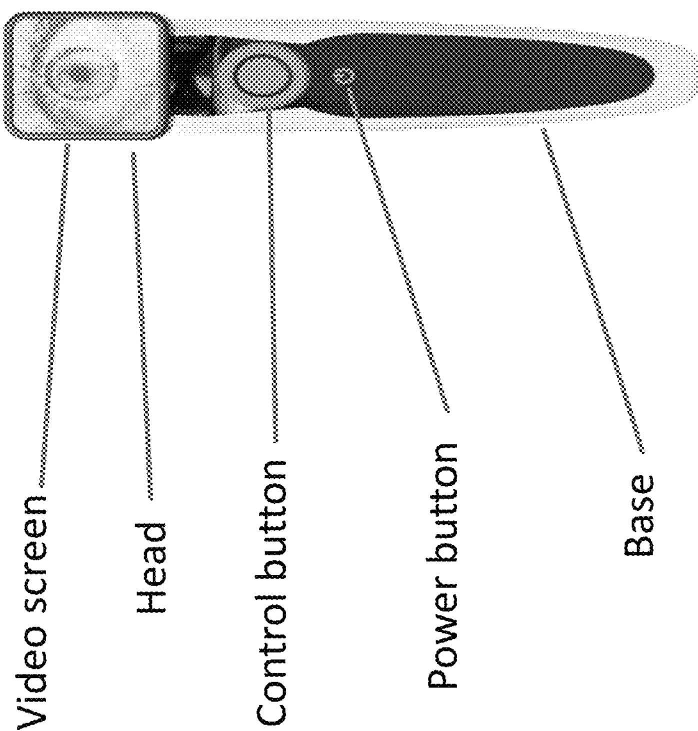
FIG. 13 is a schematic drawing of the control side of the therapeutic device. The video screen, the head module, the control button, the power button, and the base component are shown.
Figure 14:
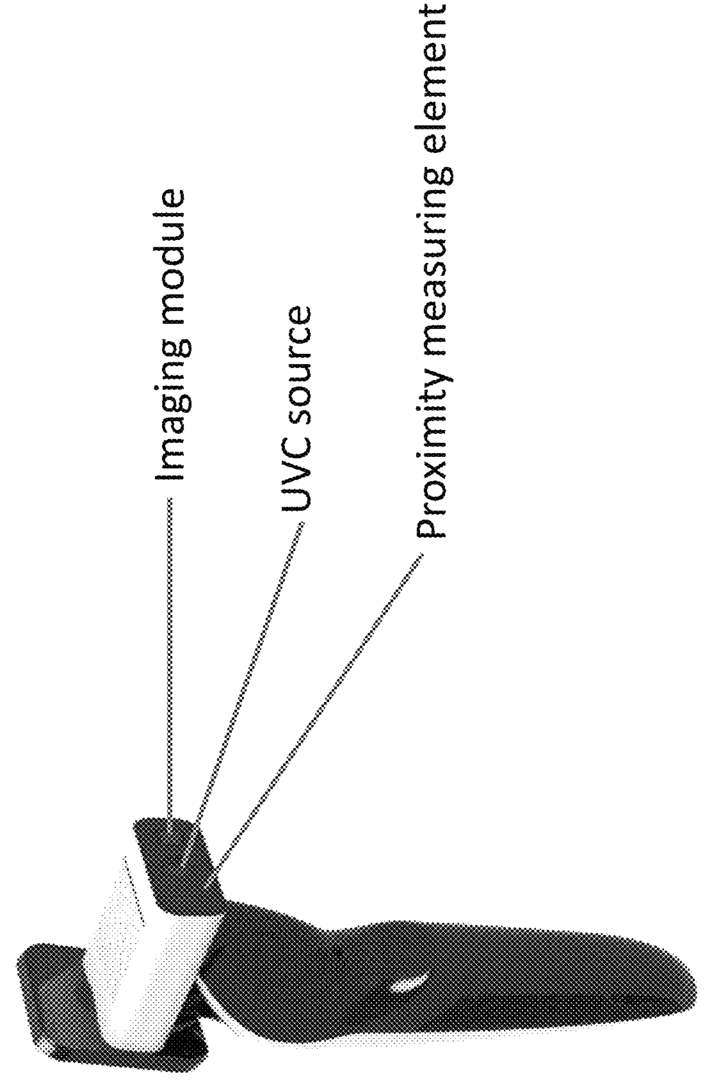
FIG. 14 is a schematic drawing of the therapeutic side of the therapeutic device. The imaging module (HD camera), UVC LED source, proximity measuring element and the base component are shown.
Figure 15:
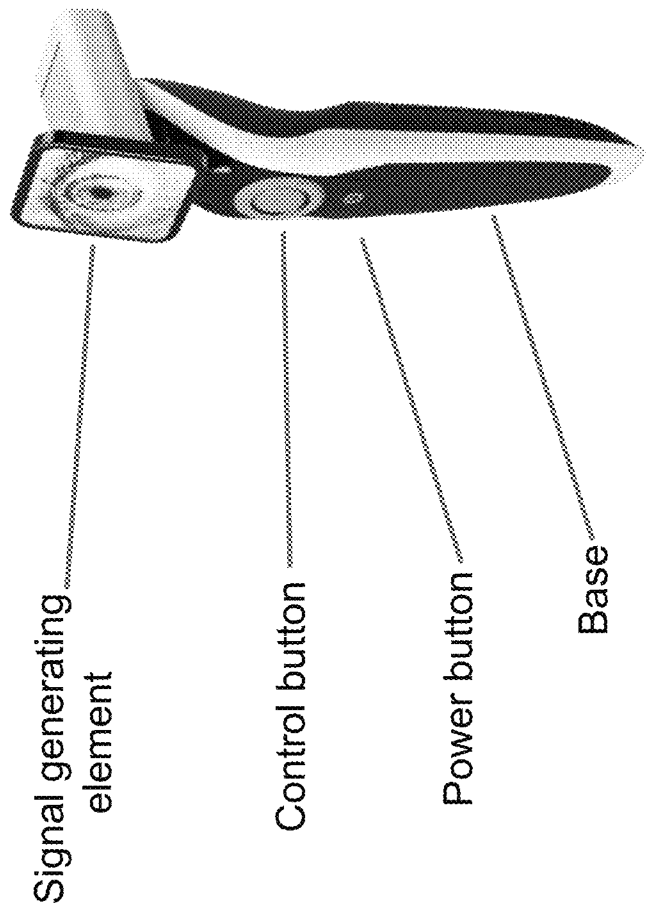
FIG. 15 is a schematic drawing of the control side of the therapeutic device. The signal generating element (video screen), the control button, the power button and the base component are shown.

The present invention features devices, systems, and methods of use thereof for delivering therapeutic or sterilizing ultraviolet (UV) radiation. The devices and systems described herein can be used for a variety of purposes, including treatment of eye conditions, such as blepharitis, meibomian gland disease (MGD), ocular cancer, eye infections, and keratoconus. The devices described herein can be used to provide sterilizing or therapeutic radiation to various tissues, such as the eye, nasal cavity, oral cavity, skin tissue, or lumen of a subject. The devices can also be used for treating cancer (e.g., an eye or eyelid cancer), a neoplasia, and/or dysplasia. In general, the devices include a base component and a head component attached thereon, the head component configured to deliver the therapeutic or sterilizing UV radiation (e.g., UVA or UVC) to a site of treatment in a subject or to a device. The devices also can be designed in a multi-functional manner, such that a single device can be used with a plurality of interchangeable heads, each of which can be used depending on the desired purpose or function. The components of the devices and systems are described in more detail below.

Base Component

The base component of a device as described herein includes a distal portion and a proximal portion, the proximal portion configured to connect a head component. The base component can have any suitable size and shape such that it is suitably configured to house the head component thereon. The base component can have an ergonomic design, for facile control a handheld-device. For example, the base component can include a handle such that the device can be easily manipulated by a user, e.g., a healthcare provider. The base component can be configured to be mounted on another device or instrument, such a microscope, a slit lamp, power source, or source of energy (e.g., UV (e.g., UVA or UVC) IR, heat, and ultrasound). The base component can include a housing, e.g., on the distal portions thereof, for attachment of a head component or other accessory component. The base component can include a housing for mounting the base component on another instrument, e.g., an slit a lamp. The base component can be designed to be removably attached (e.g., separable) to a head component, and the base component and head component form a system. Alternatively, the base component can be designed to be integral with the head component.

Head Component

The head component of a device as described herein includes a distal portion and a proximal portion, the distal portion configured to deliver a source of therapeutic energy (e.g., UV, IR, heat, microwave, intense pulsed light, and/or ultrasound) to a site of treatment or sterilization. The proximal portion of the head component is configured to be attached or mounted on the base component. The head component can have any suitable geometry to match its function, e.g., for delivering therapeutic energy to the appropriate site (e.g., eye, eyelid, nasal cavity, oral cavity, a tooth cavity, periodontal tissue, skin tissue, or a lumen (e.g., a gastrointestinal lumen, an oropharyngeal lumen, a genital lumen, or a urinary lumen). For example, a device that is configured to deliver therapeutic energy to an eyelid can include a head component with a size and shape (e.g., curvature) configured to conform to an eyelid or set of eyelids of a subject. In some embodiments, the head component can include an attachment that is configured to contact a site of treatment. In some embodiments, the head component includes a light guide configured to deliver therapeutic UV radiation to a tooth, a portion of a tooth, a tooth caries, or a tooth cavity (e.g., during a root canal or extraction procedure). In some embodiments, the light guide is configured to deliver UV radiation to an area from where a tooth or portion thereof was previously removed.

The head component can house the source of therapeutic energy, e.g., the source of therapeutic energy (e.g., UV) is integral within or on the head. Alternatively, the head component can act as a transmitter that directs the source of therapeutic energy via the source to the site of application. In some embodiments, the device further includes a light guide for delivering the UV radiation. The light guide can be attached to the head component, which transmits the therapeutic energy from the source to the site of application via the light guide.

UV Radiation

The devices described herein include a source of UV radiation. The UV radiation can be, e.g., UVC radiation, UVA radiation, or a combination thereof. The UVC radiation can have a wavelength of from about 100 nm to about 280 nm (e.g., from about 200 nm to about 280 nm, e.g., from about 220 nm to about 280 nm, e.g., from about 240 nm to about 270 nm, e.g., from about 250 nm to about 270 or from about 260 nm to about 270 nm, e.g., about 254 nm, 255 nm, or about 265 nm). The UVA radiation can have a wavelength of from about 315 nm to about 400 nm. The source of UV radiation can be configured to emit radiation at a plurality of wavelengths. The source can be tunable to emit radiation at a selected wavelength. The source of UV radiation can include at least one light-emitting diode (LED) or a plurality of LEDs that emit the UV radiation. For example, the source can include 1, 2, 3, 4, 5, 6, 7, 8, 9, 10, or more LEDs that emit UV radiation. In one embodiment, the source of UV radiation includes eight LEDs.

In some embodiments, the source of UV radiation has a power output of from about 0.005 mW to about 50 mW (e.g., from about 0.005 mW to about 5 mW, e.g., from about 0.01 mW to about 1 mW). For example, the source of UV radiation can have a power out of from about 0.005 mW to about 0.01 mW, e.g., about 0.006 mW, 0.007 mW, 0.008 mW, 0.009 mW, or 0.01 mW, e.g., from about 0.01 mW to about 0.1 mW, e.g., about 0.02 mW, 0.03 mW, 0.04 mW, 0.05 mW, 0.06 mW, 0.07 mW, 0.08 mW, 0.09 mW, or 0.1 mW, e.g., from about 0.1 mW to about 1 mW, e.g., about 0.2 mW, 0.3 mW, 0.4 mW, 0.5 mW, 0.6 mW, 0.7 mW, 0.8 mW, 0.9 mW, or 1 mW, e.g., from about 1 mW to about 10 mW, e.g., about 2 mW, 3 W, 4 mW, 5 mW, 6 mW, 7 mW, 8 mW, 9 mW, or 10 mW, e.g., about 10 mW to about 50 mW, e.g., about 15 mW, 20 mW, 25 mW, 30 mW, 35 mW, 40 mW, 45 mW, or 50 mW). The power of the source can be adjustable to emit a desired power output.

The source of UV radiation can be configured to irradiate an entire surface of an eye. The source of UV radiation can be configured to irradiate a zone of tissue that has a maximum dimension of less than about 10 cm, e.g., less than about 9 cm, 8 cm, 7 cm, 6 cm, 5 cm, 4 cm, 3 cm, 2 cm, 1 cm, 0.9 cm, 0.8 cm, 0.7 cm, 0.6 cm, 0.5 cm, 0.4 cm, 0.3 cm, 0.2 cm, or 0.1 cm. The source of radiation can be configured to irradiate a substantially circular zone of tissue, an elongate zone of tissue, or annular zone of body tissue. In some embodiments, the source of radiation is configured to be adjustable to adjust a size and/or shape of a zone that is irradiated. The device can be configured to scan the UV radiation across a zone of body tissue. This can be achieved, e.g., by moving the base component or a handle thereon, or by a rotating or moving component, e.g., in the head component.

In some embodiments, the source of UV radiation produces a radiation intensity of from about 0.01 mW/cm$^2$ to about 500 mW/cm$^2$, e.g., from about 0.01 mW/cm$^2$ to about 50 mW/cm$^2$, e.g., from about 0.01 mW/cm$^2$ to about 5 mW/cm$^2$. For example the source of UV radiation can produce a radiation intensity of from about 0.01 mW/cm$^2$ to about 0.1 mW/cm$^2$, e.g., about 0.02 mW/cm$^2$, 0.03 mW/cm$^2$, 0.04 mW/cm$^2$, 0.05 mW/cm$^2$, 0.06 mW/cm$^2$, 0.07 mW/cm$^2$, 0.08 mW/cm$^2$, 0.09 mW/cm$^2$, 0.1 mW/cm$^2$, e.g., from about 0.1 mW/cm$^2$ to about 1 mW/cm$^2$, e.g., about 0.2 mW/cm$^2$, 0.3 mW/cm$^2$, 0.4 mW/cm$^2$, 0.5 mW/cm$^2$, 0.6 mW/cm$^2$, 0.7 mW/cm$^2$, 0.8 mW/cm$^2$, 0.9 mW/cm$^2$, or 1 mW/cm$^2$, e.g., from about 1 mW/cm$^2$ to about 10 mW/cm$^2$, e.g., about 2 mW/cm$^2$, 3 mW/cm$^2$, 4 mW/cm$^2$, 5 mW/cm$^2$, 6 mW/cm$^2$, 7 mW/cm$^2$, 8 mW/cm$^2$, 9 mW/cm$^2$, 10 mW/cm$^2$, e.g., about 10 mW/cm$^2$ to about 100 mW/cm$^2$, e.g., about 20 mW/cm$^2$, 30 mW/cm$^2$, 40 mW/cm$^2$, 50 mW/cm$^2$, 60 mW/cm$^2$, 70 mW/cm$^2$, 80 mW/cm$^2$, 90 mW/cm$^2$, or 100 mW/cm$^2$, e.g., from about 100 mW/cm$^2$ to about 500 mW/cm$^2$, e.g., about 150 mW/cm$^2$, 200 mW/cm$^2$, 250 mW/cm$^2$, 300 mW/cm$^2$, 350 mW/cm$^2$, 400 mW/cm$^2$, 450 mW/cm$^2$, or 500 mW/cm$^2$.

The source of UV radiation can be administered over a time period. The dose can be administered as a continuous dose or pulsed. The dose can be administered, e.g., for about 0.01 seconds to about 600 seconds, e.g., from about 0.01 second to about 0.1 second, e.g., about 0.02 second, 0.03 second, 0.04 second, 0.05 second, 0.06 second, 0.07 second, 0.08 second, 0.09 second, or 0.1 second, e.g., from about 0.1 second to about 1 second, e.g., about 0.2 second, 0.3 second, 0.4 second, 0.5 second, 0.6 second, 0.7 second, 0.8 second, 0.9 second, or 1 second, e.g., from about 1 second to about 10 seconds, e.g., about 2 seconds, 3 seconds, 4 seconds, 5 seconds, 6 seconds, 7 seconds, 8 seconds, 9 seconds, or 10 seconds, e.g., from about 10 seconds to about 100 seconds, e.g., about 20 seconds, 30 seconds, 40 seconds, 50 seconds, 60 seconds, 70 second, 80 seconds, 90 seconds, or 100 seconds, e.g., from about 100 seconds to about 600 seconds, e.g., about 110 seconds, 120 seconds, 150 seconds, 180 seconds, 240 seconds, 270 seconds, 300 seconds, 330 seconds, 360 seconds, 390 seconds, 420 seconds, 450 seconds, 480 seconds, 510 seconds, 540 seconds, 570 seconds, or 600 seconds. A pulsed dose of radiation can include a ratio of time on to time off of, e.g., from about 0.01 to about 100, e.g., from about 0.01 to about 0.1, e.g., about 0.02, 0.03, 0.04, 0.05, 0.06, 0.07, 0.08, 0.09, or 0.1, e.g., from about 0.1 to about 1, e.g., about 0.2, 0.3, 0.4, 0.5, 0.6, 0.7, 0.8, 0.9, or 1, e.g., from about 1 to about 10, e.g., about 2, 3, 4, 5, 6, 7, 8, 9, or 10, e.g., from about 10 to about 100, e.g., about 20, 30, 40, 50, 60, 70, 80, 90, or 100. A pulsed dose of radiation can include a pulse shape or waveform selected from a group consisting of square, triangular, sine, sawtooth, and any superposition or combinations thereof.

The source of UV radiation can be administering in a dose of from about 0.01 mJ/cm$^2$ to about 500 mJ/cm$^2$, e.g., from about 0.01 mJ/cm$^2$ to about 250 mJ/cm$^2$, e.g., from about 0.01 mJ/cm$^2$ to about 15 mJ/cm$^2$, e.g., from about 1 mJ/cm$^2$ to about 15 mJ/cm$^2$. For example, the source of radiation can be administered in a dose of from about 0.01 mJ/cm$^2$ to about 0.1 mJ/cm$^2$, e.g., about 0.02 mJ/cm$^2$, 0.03 mJ/cm$^2$, 0.04 mJ/cm$^2$, 0.05 mJ/cm$^2$, 0.06 mJ/cm$^2$, 0.07 mJ/cm$^2$, 0.08 mJ/cm$^2$, 0.09 mJ/cm$^2$, or 0.1 mJ/cm$^2$, e.g., from about 0.1 mJ/cm$^2$ to about 1 mJ/cm$^2$, e.g., about 0.2 mJ/cm$^2$, 0.3 mJ/cm$^2$, 0.4 mJ/cm$^2$, 0.5 mJ/cm$^2$, 0.6 mJ/cm$^2$, 0.7 mJ/cm$^2$, 0.8 mJ/cm$^2$, 0.9 mJ/cm$^2$, or 1 mJ/cm$^2$, e.g., from about 1 mJ/cm$^2$ to about 10 mJ/cm$^2$, e.g., about 2 mJ/cm$^2$, 3 mJ/cm$^2$, 4 mJ/cm$^2$, 5 mJ/cm$^2$, 6 mJ/cm$^2$, 7 mJ/cm$^2$, 8 mJ/cm$^2$, 9 mJ/cm$^2$, or 10 mJ/cm$^2$, e.g., from about 10 mJ/cm$^2$ to about 100 mJ/cm$^2$, e.g., about 20 mJ/cm$^2$, 30 mJ/cm$^2$, 40 mJ/cm$^2$, 50 mJ/cm$^2$, 60 mJ/cm$^2$, 70 mJ/cm$^2$, 80 mJ/cm$^2$, 90 mJ/cm$^2$, or 100 mJ/cm$^2$, e.g., from about 100 mJ/cm$^2$, to about 250 mJ/cm$^2$, e.g., about 125 mJ/cm$^2$, 150 mJ/cm$^2$, 175 mJ/cm$^2$, 200 mJ/cm$^2$, 225 mJ/cm$^2$, or 250 mJ/cm$^2$. In some embodiments, the source of UV radiation includes adaptive optics components that are configured to adjust the focal point of the UV radiation.

IR Radiation

The devices described herein can include a source of IR radiation. The IR radiation can have a wavelength of from about 750 nm to about 1,000,000 nm (e.g., from about 800 nm to about 900,000 nm, from about 810 nm to about 500,000 nm, from about 820 nm to about 250,000 nm, from about 830 nm to about 100,000 nm, from about 850 nm to about 50,000 nm, from about 860 nm to about 25,000 nm, from about 870 nm to about 10,000 nm, from about 880 nm to about 9,000 nm, from about 890 nm to about 8,000 nm, from about 900 nm to about 7,000 nm, from about 910 nm to about 6,000 nm, from about 920 nm to about 5,000 nm, from about 930 nm to about 4,000 nm, from about 940 nm to about 3,000 nm, from about 950 nm to about 2,500 nm, from about 960 nm to about 2,400 nm, from about 970 nm to about 2,300 nm, from about 980 nm to about 2,200 nm, from about 990 nm to about 2,100 nm, or from about 1,000 nm to about 2,000 nm). The source of IR radiation can be configured to emit radiation at a plurality of wavelengths. The source can be tunable to emit radiation at a selected wavelength. The source of IR radiation can include at least one light-emitting diode (LED) or a plurality of LEDs that emit the IR radiation. For example, the source can include 1, 2, 3, 4, 5, 6, 7, 8, 9, 10, or more LEDs that emit IR radiation.

In some embodiments, the source of IR radiation has a power output of from about 0.005 mW to about 50 mW (e.g., from about 0.005 mW to about 5 mW, e.g., from about 0.01 mW to about 1 mW). For example, the source of IR radiation can have a power out of from about 0.005 mW to about 0.01 mW, e.g., about 0.006 mW, 0.007 mW, 0.008 mW, 0.009 mW, or 0.01 mW, e.g., from about 0.01 mW to about 0.1 mW, e.g., about 0.02 mW, 0.03 mW, 0.04 mW, 0.05 mW, 0.06 mW, 0.07 mW, 0.08 mW, 0.09 mW, or 0.1 mW, e.g., from about 0.1 mW to about 1 mW, e.g., about 0.2 mW, 0.3 mW, 0.4 mW, 0.5 mW, 0.6 mW, 0.7 mW, 0.8 mW, 0.9 mW, or 1 mW, e.g., from about 1 mW to about 10 mW, e.g., about 2 mW, 3 W, 4 mW, 5 mW, 6 mW, 7 mW, 8 mW, 9 mW, or 10 mW, e.g., about 10 mW to about 50 mW, e.g., about 15 mW, 20 mW, 25 mW, 30 mW, 35 mW, 40 mW, 45 mW, or 50 mW). The power of the source can be adjustable to emit a desired power output.

The source of IR radiation can be configured to irradiate a zone of tissue that has a maximum dimension of less than about 10 cm, e.g., less than about 90 mm, 80 mm, 70 mm, 60 mm, 50 mm, 40 mm, 30 mm, 20 mm, or 10 mm, e.g., less than about 9 mm, 8 mm, 7 mm, 6 mm, 5 m, 4 mm, 3 mm, 2 mm, or 1 mm). The source of radiation can be configured to irradiate a substantially circular zone of tissue, an elongate zone of tissue, or annular zone of body tissue. In some embodiments, the source of radiation is configured to be adjustable to adjust a size and/or shape of a zone that is irradiated. The device can be configured to scan the IR radiation across a zone of body tissue. This can be achieved, e.g., by moving the base component or a handle thereon, or by a rotating or moving component, e.g., in the head component.

In some embodiments, the source of IR radiation produces a radiation intensity of from about 0.01 mW/cm$^2$ to about 500 mW/cm$^2$, e.g., from about 0.01 mW/cm$^2$ to about 50 mW/cm$^2$, e.g., from about 0.01 mW/cm$^2$ to about 5 mW/cm$^2$. For example the source of IR radiation can produce a radiation intensity of from about 0.01 mW/cm$^2$ to about 0.1 mW/cm$^2$, e.g., about 0.02 mW/cm$^2$, 0.03 mW/cm$^2$, 0.04 mW/cm$^2$, 0.05 mW/cm$^2$, 0.06 mW/cm$^2$, 0.07 mW/cm$^2$, 0.08 mW/cm$^2$, 0.09 mW/cm$^2$, 0.1 mW/cm$^2$, e.g., from about 0.1 mW/cm$^2$ to about 1 mW/cm$^2$, e.g., about 0.2 mW/cm$^2$, 0.3 mW/cm$^2$, 0.4 mW/cm$^2$, 0.5 mW/cm$^2$, 0.6 mW/cm$^2$, 0.7 mW/cm$^2$, 0.8 mW/cm$^2$, 0.9 mW/cm$^2$, or 1 mW/cm$^2$, e.g., from about 1 mW/cm$^2$ to about 10 mW/cm$^2$, e.g., about 2 mW/cm$^2$, 3 mW/cm$^2$, 4 mW/cm$^2$, 5 mW/cm$^2$, 6 mW/cm$^2$, 7 mW/cm$^2$, 8 mW/cm$^2$, 9 mW/cm$^2$, 10 mW/cm$^2$, e.g., about 10 mW/cm$^2$ to about 100 mW/cm$^2$, e.g., about 20 mW/cm$^2$, 30 mW/cm$^2$, 40 mW/cm$^2$, 50 mW/cm$^2$, 60 mW/cm$^2$, 70 mW/cm$^2$, 80 mW/cm$^2$, 90 mW/cm$^2$, or 100 mW/cm$^2$, e.g., from about 100 mW/cm$^2$ to about 500 mW/cm$^2$, e.g., about 150 mW/cm$^2$, 200 mW/cm$^2$, 250 mW/cm$^2$, 300 mW/cm$^2$, 350 mW/cm$^2$, 400 mW/cm$^2$, 450 mW/cm$^2$, or 500 mW/cm$^2$.

The source of IR radiation can be administered over a time period. The dose can be administered as a continuous dose or pulsed. The dose can be administered, e.g., for about 0.01 seconds to about 600 seconds, e.g., from about 0.01 second to about 0.1 second, e.g., about 0.02 second, 0.03 second, 0.04 second, 0.05 second, 0.06 second, 0.07 second, 0.08 second, 0.09 second, or 0.1 second, e.g., from about 0.1 second to about 1 second, e.g., about 0.2 second, 0.3 second, 0.4 second, 0.5 second, 0.6 second, 0.7 second, 0.8 second, 0.9 second, or 1 second, e.g., from about 1 second to about 10 seconds, e.g., about 2 seconds, 3 seconds, 4 seconds, 5 seconds, 6 seconds, 7 seconds, 8 seconds, 9 seconds, or 10 seconds, e.g., from about 10 seconds to about 100 seconds, e.g., about 20 seconds, 30 seconds, 40 seconds, 50 seconds, 60 seconds, 70 second, 80 seconds, 90 seconds, or 100 seconds, e.g., from about 100 seconds to about 600 seconds, e.g., about 110 seconds, 120 seconds, 150 seconds, 180 seconds, 240 seconds, 270 seconds, 300 seconds, 330 seconds, 360 seconds, 390 seconds, 420 seconds, 450 seconds, 480 seconds, 510 seconds, 540 seconds, 570 seconds, or 600 seconds. A pulsed dose of radiation can include a ratio of time on to time off of, e.g., from about 0.01 to about 100, e.g., from about 0.01 to about 0.1, e.g., about 0.02, 0.03, 0.04, 0.05, 0.06, 0.07, 0.08, 0.09, or 0.1, e.g., from about 0.1 to about 1, e.g., about 0.2, 0.3, 0.4, 0.5, 0.6, 0.7, 0.8, 0.9, or 1, e.g., from about 1 to about 10, e.g., about 2, 3, 4, 5, 6, 7, 8, 9, or 10, e.g., from about 10 to about 100, e.g., about 20, 30, 40, 50, 60, 70, 80, 90, or 100.

The source of IR radiation can be administered in a dose of from about 0.01 mJ/cm$^2$ to about 500 mJ/cm$^2$, e.g., from about 0.01 mJ/cm$^2$ to about 250 mJ/cm$^2$, e.g., from about 0.01 mJ/cm$^2$ to about 15 mJ/cm$^2$, e.g., from about 1 mJ/cm$^2$ to about 15 mJ/cm$^2$. For example, the source of radiation can be administered in a dose of from about 0.01 mJ/cm$^2$ to about 0.1 mJ/cm$^2$, e.g., about 0.02 mJ/cm$^2$, 0.03 mJ/cm$^2$, 0.04 mJ/cm$^2$, 0.05 mJ/cm$^2$, 0.06 mJ/cm$^2$, 0.07 mJ/cm$^2$, 0.08 mJ/cm$^2$, 0.09 mJ/cm$^2$, or 0.1 mJ/cm$^2$, e.g., from about 0.1 mJ/cm$^2$ to about 1 mJ/cm$^2$, e.g., about 0.2 mJ/cm$^2$, 0.3 mJ/cm$^2$, 0.4 mJ/cm$^2$, 0.5 mJ/cm$^2$, 0.6 mJ/cm$^2$, 0.7 mJ/cm$^2$, 0.8 mJ/cm$^2$, 0.9 mJ/cm$^2$, or 1 mJ/cm$^2$, e.g., from about 1

$mJ/cm^2$ to about 10 $mJ/cm^2$, e.g., about 2 $mJ/cm^2$, 3 $mJ/cm^2$, 4 $mJ/cm^2$, 5 $mJ/cm^2$, 6 $mJ/cm^2$, 7 $mJ/cm^2$, 8 $mJ/cm^2$, 9 $mJ/cm^2$, or 10 $mJ/cm^2$, e.g., from about 10 $mJ/cm^2$ to about 100 $mJ/cm^2$, e.g., about 20 $mJ/cm^2$, 30 $mJ/cm^2$, 40 $mJ/cm^2$, 50 $mJ/cm^2$, 60 $mJ/cm^2$, 70 $mJ/cm^2$, 80 $mJ/cm^2$, 90 $mJ/cm^2$, or 100 $mJ/cm^2$, e.g., from about 100 $mJ/cm^2$, to about 250 $mJ/cm^2$, e.g., about 125 $mJ/cm^2$, 150 $mJ/cm^2$, 175 $mJ/cm^2$, 200 $mJ/cm^2$, 225 $mJ/cm^2$, or 250 $mJ/cm^2$.

Intense Pulsed Light

The devices described can include a source of intense pulsed light (IPL). The IPL source includes a non-laser light source that radiates light of various wavelengths and generates bursts of light in the form of strong pulses. The IPL source can generate light of wavelengths of from about 300 nm to about 1,200 nm (e.g., from about 400 nm to about 1100 nm, from about 500 nm to about 1000 nm, from about 600 nm to about 900 nm, or from about 700 nm to about 800 nm). The wavelength emitted by IPL varies depending on the IPL device. In some embodiments, the IPL source generates a burst of light of a broad band of wavelengths and the light is filtered to control the range of wavelengths allowed to exit the IPL source. In some examples the filter is an optical filter that is configured as a lowpass filter, a high pass filter, or a bandpass filter. In some embodiments, the filter can be configured to have a notch that allows light transmission through the filter of a small bandwidth of light (e.g., light of wavelengths that differ by less than 500 nm, 400 nm, 300 nm, 200 nm, 100 nm, 50 nm, 25 nm, 20 nm, 10 nm, 5 nm, or 2 nm). IPL energy can be delivered as a series of single, double, triple pulse sequences with pulse durations of from about 2 ms to about 25 ms (e.g., about 2 ms, about 3 ms, about 4 ms, about 5 ms, about 6 ms, about 7 ms, about 8 ms, about 9 ms, about 10 ms, about 11 ms, about 12 ms, about 13 ms, about 14 ms, about 15 ms, about 16 ms, about 17 ms, about 18 ms, about 19 ms, about 20 ms, about 21 ms, about 22 ms, about 23 ms, about 24 ms, or about 25 ms), and inter-pulse delays of from about 10 ms to about 500 ms (e.g., about 10 ms, about 20 ms, about 30 ms, about 40 ms, about 50 ms, about 60 ms, about 70 ms, about 80 ms, about 90 ms, about 100 ms, about 110 ms, about 120 ms, about 130 ms, about 140 ms, about 150 ms, about 160 ms, about 170 ms, about 180 ms, about 190 ms, about 200 ms, about 210 ms, about 220 ms, about 230 ms, about 240 ms, about 250 ms, about 260 ms, about 270 ms, about 280 ms, about 290 ms, about 300 ms, about 310 ms, about 320 ms, about 330 ms, about 340 ms, about 350 ms, about 360 ms, about 370 ms, about 380 ms, about 390 ms, about 400 ms, about 410 ms, about 420 ms, about 430 ms, about 440 ms, about 450 ms, about 460 ms, about 470 ms, about 480 ms, about 490 ms, or about 500 ms). IPL radiant energy density can have a range of from about 5 $J/cm^2$ to 60 $J/cm^2$ (e.g., about 5 $J/cm^2$, about 6 $J/cm^2$, about 7 $J/cm^2$, about 8 $J/cm^2$, about 9 $J/cm^2$, about 10 $J/cm^2$, about 11 $J/cm^2$, about 12 $J/cm^2$, about 13 $J/cm^2$, about 14 $J/cm^2$, about 15 $J/cm^2$, about 16 $J/cm^2$, about 17 $J/cm^2$, about 18 $J/cm^2$, about 19 $J/cm^2$, about 20 $J/cm^2$, about 21 $J/cm^2$, about 22 $J/cm^2$, about 23 $J/cm^2$, about 24 $J/cm^2$, about 25 $J/cm^2$, about 26 $J/cm^2$, about 27 $J/cm^2$, about 28 $J/cm^2$, about 29 $J/cm^2$, about 30 $J/cm^2$, about 31 $J/cm^2$, about 32 $J/cm^2$, about 33 $J/cm^2$, about 34 $J/cm^2$, about 35 $J/cm^2$, about 36 $J/cm^2$, about 37 $J/cm^2$, about 38 $J/cm^2$, about 39 $J/cm^2$, about 40 $J/cm^2$, about 41 $J/cm^2$, about 42 $J/cm^2$, about 43 $J/cm^2$, about 44 $J/cm^2$, about 45 $J/cm^2$, about 46 $J/cm^2$, about 47 $J/cm^2$, about 48 $J/cm^2$, about 49 $J/cm^2$, about 50 $J/cm^2$, about 51 $J/cm^2$, about 52 $J/cm^2$, about 53 $J/cm^2$, about 54 $J/cm^2$, about 55 $J/cm^2$, about 56 $J/cm^2$, about 57 $J/cm^2$, about 58 $J/cm^2$, about 59 $J/cm^2$, or about 60 $J/cm^2$).

Ultrasound

The devices described herein can include a source of ultrasound, such as an ultrasound transducer. The ultrasound can have a frequency of from about 20 Hz to about 20 MHz. The ultrasound transducer can be configured to emit ultrasound at a plurality of frequencies. The source can be tunable to emit ultrasound at a selected frequency. The source of ultrasound can include at least one transducer or a plurality of transducers that emit the ultrasound. For example, the source can include 1, 2, 3, 4, 5, 6, 7, 8, 9, 10, or more transducers that emit ultrasound.

In some embodiments, the source of ultrasound has a frequency of from about 20 Hz to about 20 MHz, e.g., from about 20 Hz to about 100 kHz, e.g., from about 20 kHz to about 100 kHz, from about 20 kHz to about 80 kHz, or from about 40 kHz to about 80 kHz, e.g., about 20 kHz or about 40 kHz. For example, the source of ultrasound can have a frequency of from about 20 Hz to about 100 Hz, e.g., 30 Hz, 30 Hz, 40 Hz, 50 Hz, 60 Hz, 70 Hz, 80 Hz, 90 Hz, or 100 Hz, e.g., from about 100 Hz to about 1 kHz, e.g., about 200 Hz, 300 Hz, 400 Hz, 500 Hz, 600 Hz, 700 Hz, 800 Hz, 900 Hz, or 1 kHz, e.g., from about 1 kHz to about 10 kHz, e.g., about 2 kHz, 3 kHz, 4 kHz, 5 kHz, 6 kHz, 7 kHz, 8 kHz, 9 kHz, or 10 kHz, e.g., from about 10 kHz to about 100 kHz, e.g., about 20 kHz, 30 kHz, 40 kHz, 50 kHz, 60 kHz, 70 kHz, 80 kHz, 90 kHz, or 100 kHz, e.g., from about 100 kHz to about 1 MHz, e.g., about 200 kHz, 300 kHz, 400 kHz, 500 kHz, 600 kHz, 700 kHz, 800 kHz, 900 kHz, or 1 MHz, e.g., from about 1 MHz to about 20 MHz, e.g., about 2 MHz, 3 MHz, 4 MHz, 5 MHz, 6 MHz, 7 MHz, 8 MHz, 9 MHz, 10 MHz, 11 MHz, 12 MHz, 13 MHz, 14 MHz, 15 MHz, 16 MHz, 17 MHz, 18 MHz, 19 MHz, or 20 MHz.

In some embodiments, a low-frequency range of ultrasound, e.g., from 20 kHz to about 100 kHz is provided. In some embodiments, the frequency range of the ultrasound wave being supplied is about 40 kHz. In other configurations, the frequency range of the ultrasound wave being supplied is about 20 kHz. Low-frequency ultrasound wave ranges as described herein (below 100 kHz) are unique and differ to ultrasound at other ranges due to its effect on stimulating cells and increasing cell membrane permeability (e.g., cavitation). In particular, it is understood that ultrasound waves below the frequency of 100 kHz, advantageously, can exhibit unique properties independent to thermal effects such as cavitation, micro-cavitation, formation of microjets and acoustic streaming effects on treated cells. These effects help break up clogged or solidified lipid obstructions within portions of the eye, e.g., the Meibomian gland.

In some embodiments, the ultrasound transducer is attached to a stainless-steel plate, e.g., bent at 90° at the terminal end to fashion a contact footplate. The contact footplate can be configured to contact, e.g., an eyelid of a subject. The footplate can have a length and width, independently, of from about 10 mm to about 100 mm, e.g., about 15 mm, 20 mm, 25 mm, 30 mm, 35 mm, 40 mm, 45 mm, 50 mm, 55 mm, 60 mm, 65 mm, 70 mm, 75 mm, 80 mm, 85 mm, or 100 mm. In some embodiments, the contact footplate is about 45 mm wide and about 20 mm high.

Heat

The devices described herein can include a source of heat, e.g., IR, or resistance wire. The heating element can have a heat output from about 10 J to about 10,000 J. The source of heat can be configured to emit heat from a plurality of individual elements. For example, the source can include 1, 2, 3, 4, 5, 6, 7, 8, 9, 10, or more heat elements that emit heat.

In some embodiments the heating elements can be composed of light emitting diodes (LEDs).

In some embodiments heating can occur using radiation wavelengths from about 1500 nm to about 2,000,000 nm, e.g., about 2000 nm to about 1,000,000 nm, about 10,000 nm to about 500,000 nm, about 20,000 nm to about 100,000 nm, about 50,000 nm to about 100,000 nm, about 1,000,000 nm to about 2,000,000 nm, 1,100,000 nm to about 1,900,000 nm, 1,200,000 nm to about 1,800,000 nm, 1,300,000 nm to about 1,800,000 nm, 1,400,000 nm to about 1,700,000 nm, 1,500,000 nm to about 1,600,000 nm, about 1,100,000 nm, about 1,200,000 nm, about 1,300,000 nm, about 1,400,000 nm, about 1,500,000 nm, about 1,600,000 nm, about 1,700,000 nm, about 1,800,000 nm, about 1,900,000 nm, or about 2,000,000 nm.

The source of heat can be administered over a time period. The dose can be administered as a continuous dose or pulsed. The dose can be administered, e.g., for about 0.01 seconds to about 600 seconds, e.g., from about 0.01 second to about 0.1 second, e.g., about 0.02 second, 0.03 second, 0.04 second, 0.05 second, 0.06 second, 0.07 second, 0.08 second, 0.09 second, or 0.1 second, e.g., from about 0.1 second to about 1 second, e.g., about 0.2 second, 0.3 second, 0.4 second, 0.5 second, 0.6 second, 0.7 second, 0.8 second, 0.9 second, or 1 second, e.g., from about 1 second to about 10 seconds, e.g., about 2 seconds, 3 seconds, 4 seconds, 5 seconds, 6 seconds, 7 seconds, 8 seconds, 9 seconds, or 10 seconds, e.g., from about 10 seconds to about 100 seconds, e.g., about 20 seconds, 30 seconds, 40 seconds, 50 seconds, 60 seconds, 70 second, 80 seconds, 90 seconds, or 100 seconds, e.g., from about 100 seconds to about 600 seconds, e.g., about 110 seconds, 120 seconds, 150 seconds, 180 seconds, 240 seconds, 270 seconds, 300 seconds, 330 seconds, 360 seconds, 390 seconds, 420 seconds, 450 seconds, 480 seconds, 510 seconds, 540 seconds, 570 seconds, or 600 seconds. A pulsed dose of radiation can include a ratio of time on to time off of, e.g., from about 0.01 to about 100, e.g., from about 0.01 to about 0.1, e.g., about 0.02, 0.03, 0.04, 0.05, 0.06, 0.07, 0.08, 0.09, or 0.1, e.g., from about 0.1 to about 1, e.g., about 0.2, 0.3, 0.4, 0.5, 0.6, 0.7, 0.8, 0.9, or 1, e.g., from about 1 to about 10, e.g., about 2, 3, 4, 5, 6, 7, 8, 9, or 10, e.g., from about 10 to about 100, e.g., about 20, 30, 40, 50, 60, 70, 80, 90, or 100.

In some embodiments the heat source can be configured to be electrically connected to a thermistor sensor for feedback control of the heating element. In some embodiments, a control loop feedback mechanism, e.g., a proportional-integral-derivative (PID) controller, can be connected to the thermistor sensor for continuous monitoring of the heating element output for the safety of user and/or the recipient of the heat. The heat source can be configured to provide a constant temperature (e.g., from about 30° C. to about 50° C., e.g., about 31° C. 32° C. 33° C., 34° C., 35° C., 36° C., 37° C., 38° C., 39° C., 40° C., 41° C., 42° C., 43° C., 44° C., 45° C., 46° C., 47° C., 48° C., 49° C., or 50° C.). Other heat sources are known in the art. The heat source can be positioned on the head component, e.g., configured to contact the eyelid or tissue site of the subject.

Microwave Radiation

The devices described herein can include a source of microwave, such as a microwave transducer. The microwave can have a frequency of from about 300 MHz to about 300 GHz (e.g., about 400 MHz, about 500 MHz, about 600 MHz, about 700 MHz, about 800 MHz, about 900 MHz, about 1 GHz, about 2 GHz, about 3 GHz, about 4 GHz, about 5 GHz, about 6 GHz, about 7 GHz, about 8 GHz, about 9 GHz, about 10 GHz, about 20 GHz, about 50 GHz, about 100 GHz, about 200 GHz, about 300 GHz). The microwave transducer can be configured to emit microwave radiation at a plurality of frequencies. The source can be tunable to emit microwave at a selected frequency. The source of microwave can include at least one transducer or a plurality of transducers that emit the microwave radiation. For example, the source can include 1, 2, 3, 4, 5, 6, 7, 8, 9, 10, or more transducers that emit microwave radiation.

In some embodiments a microwave source can be configured to emit microwave radiation of wavelength from about 1 mm to about 1,000 mm, e.g., about 2 mm to about 900 mm, about 5 mm to about 800 mm, about 10 mm to about 700 mm, about 20 mm to about 600 mm, about 50 mm to about 500 mm, about 100 mm to about 400 mm, about 200 mm to about 300 mm, about 10 mm, about 20 mm, about 30 mm, about 40 mm, about 50 mm, about 60 mm, about 70 mm, about 80 mm, about 90 mm, about 100 mm, about 110 mm, about 120 mm, about 130 mm, about 140 mm, about 150 mm, about 160 mm, about 170 mm, about 180 mm, about 190 mm, about 200 mm, about 200 mm, about 210 mm, about 220 mm, about 230 mm, about 240 mm, about 250 mm, about 260 mm, about 270 mm, about 280 mm, about 290 mm, about 300 mm, about 310 mm, about 320 mm, about 330 mm, about 340 mm, about 350 mm, about 360 mm, about 370 mm, about 380 mm, about 390 mm, about 400 mm, about 410 mm, about 420 mm, about 430 mm, about 440 mm, about 450 mm, about 460 mm, about 470 mm, about 480 mm, about 490 mm, about 500 mm, about 510 mm, about 520 mm, about 530 mm, about 540 mm, about 550 mm, about 560 mm, about 570 mm, about 580 mm, about 590 mm, about 600 mm, about 610 mm, about 620 mm, about 630 mm, about 640 mm, about 650 mm, about 660 mm, about 670 mm, about 680 mm, about 690 mm, about 700 mm, about 710 mm, about 720 mm, about 730 mm, about 740 mm, about 750 mm, about 760 mm, about 770 mm, about 780 mm, about 790 mm, about 800 mm, about 810 mm, about 820 mm, about 830 mm, about 840 mm, about 850 mm, about 860 mm, about 870 mm, about 880 mm, about 890 mm, about 900 mm, about 910 mm, about 920 mm, about 930 mm, about 940 mm, about 950 mm, about 960 mm, about 970 mm, about 980 mm, about 990 mm, or about 1,000 mm.

Light Guide

In some embodiments, the devices described herein include a light guide for delivering therapeutic (e.g., UVC) radiation. A light guide is a device used to distribute light (e.g., UV) from a source to a particular area. A light guide can be made of a transparent material (e.g., glass or plastic) including a material that transmits UVC radiation. The light guide can contain thin filaments therein capable of transmitting light signals through internal reflections. The light guide can be attached to the head component, and the UV energy is transmitted from the UV source to the site of application via the light guide. A light guide can be, for example, a waveguide, an optical fiber, a liquid light guide, a hollow tube (FIGS. 28A-28D). The light guide can be configured to mate with the light source. The light guide has a receiving end, e.g., connected to the source of UV, and a transmitting end (FIGS. 28A-28D) configured to deliver the light to a desired area, such as to various tissues, such as the eye, nasal cavity, oral cavity, skin tissue, or lumen of a subject.

The light guide can have any suitable width and or length provided it can effectively deliver the UV light to a site of administration. For example, the light guide can have a length of, e.g., from about 1 mm to about 1 m, e.g., from about 1 mm to about 10 mm, e.g., about 2 mm, 3 mm, 4 mm, 5 mm, 6 mm, 7 mm, 8 mm, 9 mm, or 10 mm, e.g., from about 10 mm to about 100 mm, e.g., about 20 mm, 30 mm, 40 mm, 50 mm, 60 mm, 70 mm, 80 mm, 90 mm, or 100 mm, e.g., from about 100 mm to about 1 m, e.g., about 200 mm, 300 mm, 400 mm, 500 mm, 600 mm, 700 mm, 800 mm, 900 mm, or 1 m.

The thickness of the light guide (e.g., diameter) or the filaments located within can be, e.g., from about 1 mm to about 50 mm, e.g., about 2 mm to about 25 mm, e.g., about 4 mm to about 15 mm, e.g., about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm 25 mm, 30 mm, 35 mm, 40 mm, 45 mm, or 50 mm.

The light guide can be or can include a fiber light guide, which refers to any fiber capable of carrying UV light of any kind from one end to the other. In one embodiment, the fiber light guide carries light of from about 180 nm to 465 nm. Well known light fibers include those made of fused silica, pure silica, organosilicons, hollow tubes, clad and unclad fibers where the fibers are either singular or bundled. Other optical fibers include liquid fibers that are water based or other diluents such as alcohols, ethers, aldehydes, ketones, and other liquids suitable for transmitting effective wavelengths and some can reduce thermal energy including infrared energy.

Vitrectomy Element

Figure 25:
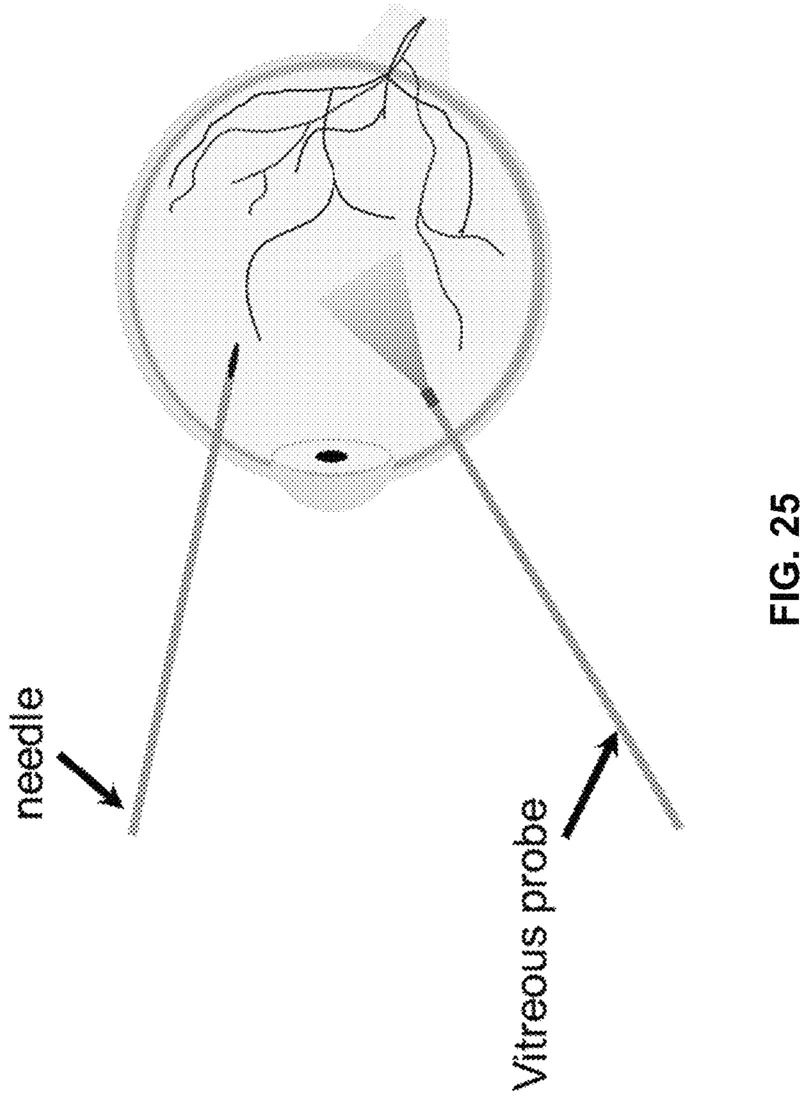
FIG. 25 is a schematic drawing showing an embodiment of the light guide delivering UVC light into the vitreous body of an eye. A needle may be used in combination to extract a portion of the vitreous body.
Figures 26A, 26B:
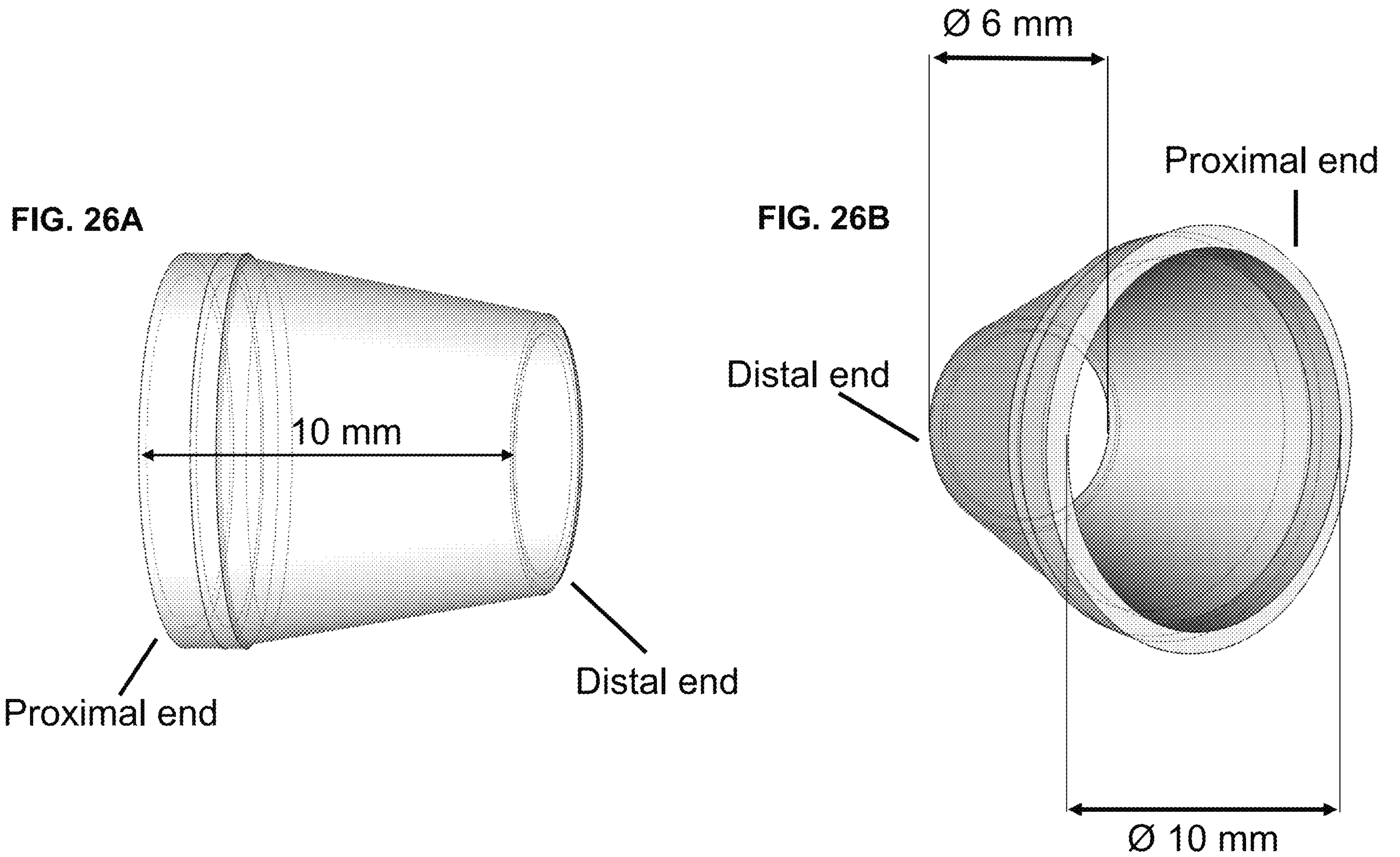
FIGS. 26A and 26B are schematic drawings of an embodiment of the eye stabilizing element having a length from the proximal end to the distal end of 10 mm. The distal end is shown as a smooth edge. The eye stabilizing element is shown in the shape of a cone having a larger diameter at the proximal end than at the distal end. The distal end contacts the eye of a subject to stabilize the eye and minimize eye movement. The proximal end is configured to attach to the distal end of the head component of the device.

The devices and methods of the invention may include a vitrectomy element (e.g., a vitrectomy port, a vitreous probe, or a trocar) (FIG. 23, FIG. 24A, FIG. 24B, and FIG. 25). The vitrectomy element can be or can include a hollow tube having one or more sharp edges at the distal end to puncture and penetrate through the sclera of an eye and configured to deliver a therapeutic dose of radiation to an interior region of the eye (e.g., an anterior region, a posterior region, a vitreous chamber region, a retinal region, a choroidal region, a macular region, an intraocular lens region, a ciliary muscle region, or an optic nerve region). In some embodiments, the vitrectomy element is configured as a high frequency cutting device (e.g., a vitrectomy machine) configured to cut vitreous. In some embodiments, a needle may be inserted into the vitreous region of the eye through the opening generated by the vitrectomy element (FIG. 25). In some embodiments, the vitrectomy element is configured to allow a light guide to be threaded within the vitrectomy element into an interior region of the eye. In some embodiments the vitrectomy element is configured to attach to the eye stabilizing element. In some embodiments, the proximal end of the vitrectomy element is configured to attach to the head component and the distal end is configured to attach to the eye stabilizing element. In some embodiments, the vitrectomy element is configured to accept a therapeutic dose of radiation (e.g., UVC) from a source of radiation located in the head component and the therapeutic dose exits the vitrectomy element at the distal end of the stabilizing element. In some embodiments, the vitrectomy element is configured with a vitreous probe configured connect to a source of radiation of the head component. In some embodiments, the vitrectomy element can have a base with a diameter of from about 1 mm to about 10 mm (e.g., about 1 mm, about 2 mm, about 3 mm, about 4 mm, about 5 mm, about 6 mm, about 7 mm, about 8 mm, about 9 mm, or about 10 mm). In some embodiments, the vitrectomy element is configured to include a vitreous probe configured to attach to the base of the vitrectomy element. In some embodiments, the vitreous probe is configured to have a length of from about 1 mm to about 20 mm (e.g., from about 2 mm to about 19 mm, from about 3 mm to about 18 mm, from about 4 mm to about 17 mm, from about 5 mm to about 16 mm, from about 6 mm to about 15 mm, from about 7 mm to about 14 mm, from about 8 mm to about 13 mm, from about 9 mm to about 12 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, or about 20 mm). In some embodiments, the vitreous probe is configured to have a diameter of from about 0.05 mm to about 10 mm (e.g., about 0.05 mm, about 0.06 mm, about 0.07 mm, about 0.08 mm, about 0.09 mm, about 0.1 mm, about 0.2 mm, about 0.3 mm, about 0.4 mm, about 0.5 mm, about 0.6 mm, about 0.7 mm, about 0.8 mm, about 0.9 mm, about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, about 2.0 mm, about 2.1 mm, about 2.2 mm, about 2.3 mm, about 2.4 mm, about 2.5 mm, about 2.6 mm, about 2.7 mm, about 2.8 mm, about 2.9 mm, about 3.0 mm, about 3.1 mm, about 3.2 mm, about 3.3 mm, about 3.4 mm, about 3.5 mm, about 3.6 mm, about 3.7 mm, about 3.8 mm, about 3.9 mm, about 4.0 mm, about 4.1 mm, about 4.2 mm, about 4.3 mm, about 4.4 mm, about 4.5 mm, about 4.6 mm, about 4.7 mm, about 4.8 mm, about 4.9 mm, about 5.0 mm, about 5.1 mm, about 5.2 mm, about 5.3 mm, about 5.4 mm, about 5.5 mm, about 5.6 mm, about 5.7 mm, about 5.8 mm, about 5.9 mm, about 6.0 mm, about 6.1 mm, about 6.2 mm, about 6.3 mm, about 6.4 mm, about 6.5 mm, about 6.6 mm, about 6.7 mm, about 6.8 mm, about 6.9 mm, about 7.0 mm, about 7.1 mm, about 7.2 mm, about 7.3 mm, about 7.4 mm, about 7.5 mm, about 7.6 mm, about 7.7 mm, about 7.7 mm, about 7.9 mm, about 8.0 mm, about 8.1 mm, about 8.2 mm, about 8.3 mm, about 8.4 mm, about 8.5 mm, about 8.6 mm, about 8.7 mm, about 8.8 mm, about 8.9 mm, about 9.0 mm, about 9.1 mm, about 9.2 mm, about 9.3 mm, about 9.4 mm, about 9.5 mm, about 9.6 mm, about 9.7 mm, about 9.8 mm, about 9.9 mm, or about 10.0 mm). In some embodiments, the vitrectomy element is configured as a vitreous probe having a base with a diameter of about 6 mm, a length of about 12 mm, and a probe diameter of about 1 mm.

Proximity Determining Element

A device as described herein can include a proximity determining element. A proximity determining element is a component that is configured to detect a distance between the source of energy (e.g., UV radiation, e.g., UVC radiation) and a site of administration, e.g., treatment. As the devices described herein provide therapeutic radiation, it is desirable for the device to be positioned at an appropriate distance to provide safe and efficacious administration of energy. In some embodiments, the device does not directly contact the site of administration. Thus, the device can include a proximity determining element that detects a predetermined distance from the site of administration upon which the source of energy should be activated. The proximity determining element can be located on the head component or on the base component.

Any suitable mechanism can be used as a proximity determining element. For example, an optical sensor can be used to detect a distance between the source of energy and the site of administration. In one embodiment, the proximity determining element includes two or more light beams (e.g., lasers) that convergently align when reaching a predetermined distance. For example, if the device is preferentially located at the predetermined distance from the site of administration, the two light beams can converge and illuminate the zone of body tissue to be irradiated when the device is suitably positioned. The predetermined distance can be, e.g., from about 1 mm to about 100 cm from the site of administration, e.g., about 1 mm to about 100 mm, about 1 mm to about 50 mm, about 1 mm to about 25 mm, about 2 mm to about 20 mm, or about 5 mm to about 10 mm, e.g., about 8 mm.

Eye Stabilizing Element

The devices described herein can include an eye stabilizing element. The eye stabilizing element can have a proximal end that is configured to attach to the distal end of the head component and a distal end that is configured to contact the eye of the subject. In some embodiments, the eye stabilizing element has the shape of a cone or a cylinder having a first diameter and a second diameter at the proximal end and distal end respectively (FIGS. 25A and 25B). In some embodiments, the first diameter is smaller than the second diameter. In some embodiments, the first diameter is larger than the second diameter. In some embodiments the first diameter is equal to the second diameter. In some embodiments, the first and second diameter have a diameter large enough to accommodate a beam of UVC radiation having a beam diameter of from about 1 mm to about 15 mm (e.g., about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, or about 15 mm, e.g., about 4.5 mm). In some embodiments, the first and second diameters are from about 1 mm to about 20 mm (e.g., from about 2 mm to about 19 mm, from about 3 mm to about 18 mm, from about 4 mm to about 17 mm, from about 5 mm to about 16 mm, from about 6 mm to about 15 mm, from about 7 mm to about 14 mm, from about 8 mm to about 13 mm, from about 9 mm to about 12 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, or about 20 mm).

In some embodiments, the eye stabilizing element is configured in the shape of a cone having a first diameter of from about 1 mm to about 20 mm (e.g., from about 2 mm to about 19 mm, from about 3 mm to about 18 mm, from about 4 mm to about 17 mm, from about 5 mm to about 16 mm, from about 6 mm to about 15 mm, from about 7 mm to about 14 mm, from about 8 mm to about 13 mm, from about 9 mm to about 12 mm, or from about 10 mm to about 11 mm), a second diameter of from about 1 mm to about 10 mm (e.g., about 1 mm, about 2 mm, about 3 mm, about 4 mm, about 5 mm, about 6 mm, about 7 mm, about 8 mm, about 9 mm, or about 10 mm), a length of from about 1 mm to about 20 mm (e.g., from about 2 mm to about 19 mm, from about 3 mm to about 18 mm, from about 4 mm to about 17 mm, from about 5 mm to about 16 mm, from about 6 mm to about 15 mm, from about 7 mm to about 14 mm, from about 8 mm to about 13 mm, from about 9 mm to about 12 mm, or from about 10 mm to about 11 mm), a treatment distance of from about 5 mm to about 11 mm (e.g., from about 6 mm to about 10 mm, from about 7 mm to about 9 mm, or about 8 mm), a base with a length of from about 1 mm to about 3 mm (e.g., about 2 mm) to accommodate a beam diameter of from about 1 mm to about 5 mm (e.g., about 1 mm, about 2 mm, about 3 mm, about 4 mm, or about 5 mm). In some embodiments the eye stabilizing element is configured in the shape of a cone having a first diameter of about 10 mm, a second diameter of about 6 mm, a length of about 10 mm, a treatment distance of about 8 mm, a base for attachment to the distal end of the source of UV radiation of about 2 mm in order to accommodate a beam diameter of about 4.5 mm.

Figures 27A, 27B:
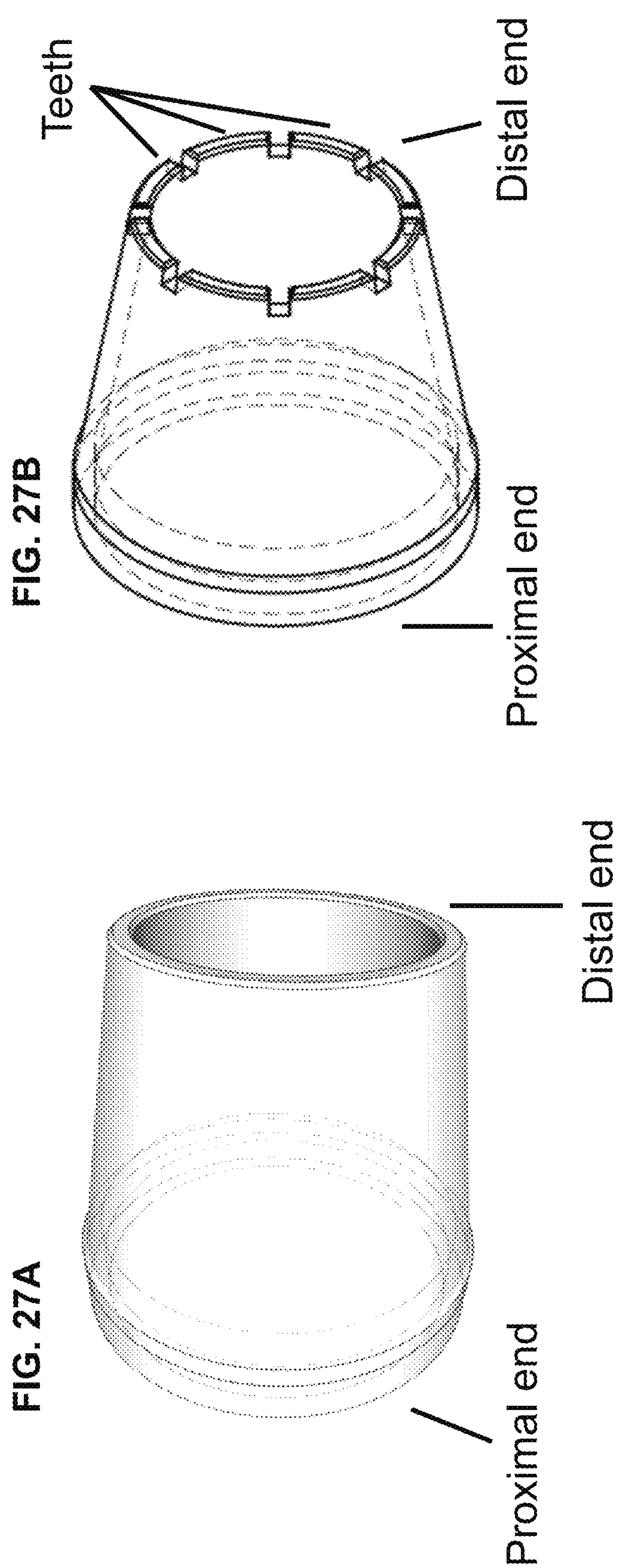
FIG. 27A is a schematic drawing of an embodiment of the eye stabilizing element. The distal end is shown as having a smooth edge. The eye stabilizing element is shown in the shape of a cone having a larger diameter at the proximal end than at the distal end. The distal end contacts the eye of a subject to stabilize the eye and minimize eye movement. The proximal end is configured to attach to the distal end of the head component of the device.
FIG. 27B is a schematic drawing of an embodiment of the eye stabilizing element. The distal end is shown as having a castellated edge with teeth. The eye stabilizing element is shown in the shape of a cone having a larger diameter at the proximal end than at the distal end. The distal end contacts the eye of a subject to stabilize the eye and minimize eye movement. The proximal end is configured to attach to the distal end of the head component of the device.
Figures 28A, 28B, 28C, 28D:
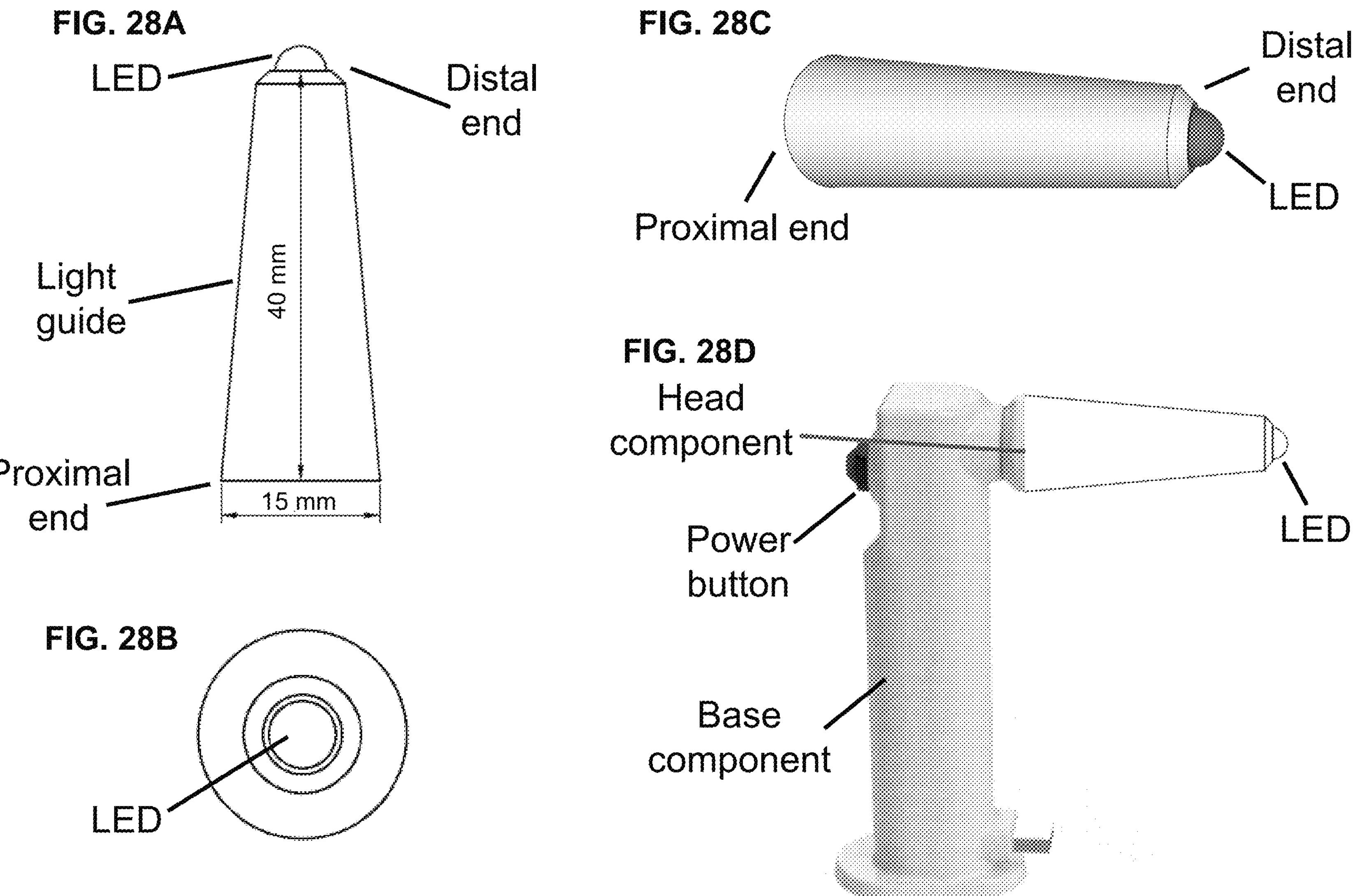
FIG. 28A is a schematic drawing of an embodiment of the light guide used to deliver a therapeutic dose of UVC to a mouth of a subject (e.g., to treat gingivitis). This exemplary embodiment is shown having a length of 40 mm from the proximal end to the distal end and a 15 mm diameter at the proximal end. The light guide is configured to be attached to the head component of the device at the proximal end. The light guide is configured with a UVC LED at the distal end.
FIG. 28B is a schematic drawing of a top view of an embodiment of the light guide used to deliver a therapeutic dose of UVC to a mouth of a subject (e.g., to treat gingivitis). The UVC LED is shown.
FIG. 28C is a schematic drawing of a side view of an embodiment of the light guide used to deliver a therapeutic dose of UVC to a mouth of a subject (e.g., to treat gingivitis). The proximal and distal ends are shown as well as the UVC LED at the distal end.
FIG. 28D is side view of an embodiment of the light guide used to deliver a therapeutic dose of UVC to a mouth of a subject (e.g., to treat gingivitis). The light guide is shown attached to the head component as well as the base component and the UVC LED.

In some embodiments, the distal end of the eye stabilizing element has a smooth edge (FIG. 27A and FIG. 27B). In some embodiments, the distal end of the eye stabilizing element has a shaped edge (e.g., castellated edge) and includes a plurality (e.g., about 2, about 3, about 4, about 5, about 6, about 7, about 8, about 9, or about 10) protrusions and/or grooves, such as teeth, that contact and stabilize the eye (FIG. 28B). In some embodiments, the teeth are evenly distributed along the circumference of the distal end of the eye stabilizing element. In some embodiments, the teeth have a triangular shape that end in a point and the point of the teeth has an angle from about 1° to about 179° (e.g., 1°, 2°, 3°, 4°, 5°, 6°, 7°, 8°, 9°, 10°, 11°, 12°, 13°, 14°, 15°, 16°, 17°, 18°, 19°, 20°, 21°, 22°, 23°, 24°, 25°, 26°, 27°, 28°, 29°, 30°, 31°, 32°, 33°, 34°, 35°, 36°, 37°, 38°, 39°, 40°, 41°, 42°, 43°, 44°, 45°, 46°, 47°, 48°, 49°, 50°, 51°, 52°, 53°, 54°, 55°, 56°, 57°, 58°, 59°, 60°, 61°, 62°, 63°, 64°, 65°, 66°, 67°, 68°, 69°, 70°771°, 72°, 73°, 74°, 75°, 76°, 77°, 78°, 79°, 80°791°, 92°, 93°, 94°, 95°, 96°, 97°, 98°, 99°, 100°, 101°, 102°, 103°, 104°, 105°, 106°, 107°, 108°, 109°, 110°, 111°, 112°, 113°, 114°, 115°, 116°, 117°, 118°, 119°, 120°, 121°, 122°, 123°, 124°, 125°, 126°, 127°, 128°, 129°, 130°, 131°, 132°, 133°, 134°, 135°, 136°, 137°, 138°, 139°, 140°, 141°, 142°, 143°, 144°, 145°, 146°, 147°, 148°, 149°, 150°, 151°, 152°, 153°, 154°, 155°, 156°, 157°, 158°, 159°, 160°, 161°, 162°, 163°, 164°, 165°, 166°, 167°, 168°, 169°, 170°, 171°, 172°, 173°, 174°, 175°, 176°, 177°, 178°, or 179°). In some embodiments, the eye stabilizing element also establishes an optimal distance from the head component and the eye of the subject. In some embodiments, the optimal distance is from about 1 mm to about 20 mm (e.g., from about 2 mm to about 19 mm, from about 3 mm to about 18 mm, from about 4 mm to about 17 mm, from about 5 mm to about 16 mm, from about 6 mm to about 15 mm, from about 7 mm to about 14 mm, from about 8 mm to about 13 mm, from about 9 mm to about 12 mm, or about 10 mm, e.g., about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, or about 20 mm). In some embodiments, the eye stabilizing element is composed of a material that is not transparent to UVC light. In some embodiments, the stabilizing element is hollow form the proximal end to the distal end. In some embodiments, the eye stabilizing element is disposable, for single use only, and contains a tag (e.g., a radio frequency identification (RFID) tag) to prevent from the eye stabilizing to be reused. In some embodiments, the distal end of the eye stabilizing element is shaped with features (e.g., protrusions, grooves, or teeth) of a substantially small size that renders the eye stabilizing element impossible to clean. In some embodiments the eye stabilizing element is not sterilizable. In some embodiments the eye stabilizing element is made of a material that is transparent to visible light. In some embodiments, the eye stabilizing element is made of a plastic material (e.g., a thermoplastic (e.g., polyvinyl chloride, polystyrene, polyamides, polyesters, and polyurethanes), polyethylene terephthalate, polyethylene, polyvinyl chloride, polypropylene, polylactic acid, polycarbonate, acrylic plastics, polyoxymethylene, nylon, or acrylonitrile butadiene styrene). In some embodiments, the eye stabilizing element includes a component used to maintain the eyelid of the subject open (e.g., a speculum). In some embodiments, the eye stabilizing element includes features that provide grip and/or improved handling stability (e.g., ridges, grooves, lines, indentations, or curves).

Signal Generating Element

The devices described herein can include a signal generating element. The signal generating element provides a signal, such as an alert or stimulus, upon detection of the predetermined distance. The signal generating element can be operatively connected to the proximity determining element to generate the signal when the proximity determining element detects the predetermined distance. The signal can be an auditory, visual, or tactile signal. For example, the signal generating element can generate a vibration upon reaching the predetermined distance to alert the user, e.g., holding the device, to administer the source of UV radiation upon reaching the predetermined distance. In another embodiment, the signal generating element automatically triggers activation of the source of UV, e.g., by opening an aperture or providing power to the source. In this embodiment, the signal generating element can also generate an auditory, visual, or tactile signal. Alternatively, it can generate an electrical signal.

Aperture Control Element

The devices described herein can include an aperture control element configured to modulate the aperture size of the source of UV radiation (e.g., UVC radiation). The aperture control element can be present on the head component. For example, the aperture control element can be an accessory feature that mates with the head, e.g., near the source of UV radiation. Alternatively, the aperture control element can be integral within the head. In one embodiment, the aperture control element is a cone or plurality of cones that are mounted on the head component. Different cones can have different sizes to control the aperture size. The aperture diameter can be, e.g., from about 1 mm to about 50 mm, e.g., from about 2 mm to about 40 mm, e.g., about 4 mm, about 8 mm, or about 25 mm. In some embodiments, the aperture control element is configured to allow for 360° irradiation, e.g., when used with a laryngoscope. In some embodiments, the invention features a system that includes a plurality of aperture control elements, and each aperture control element (e.g., cone) is configured for a different use or method of treatment, depending on the intensity, power, and distance required for administration.

Imaging Module

The devices described herein can include an imaging module configured to display an image of the site of treatment or administration. The imaging module allows the user to receive visual feedback during UV administration. The imaging module can include, e.g., a detector (e.g., a camera, e.g., a CCD camera) and a display. Suitable detectors and displays are known in the art. The imaging module can be positioned on the head component or on the base component. In some embodiments, a detector can be positioned on the head component, and a display can be positioned on the base component. In embodiments with a light guide, the imaging module, or a portion thereof (e.g., detector or camera) can be positioned on the distal end of the light guide, e.g., to visualize the area closest to the distal end of the light guide. For example, a device with a light guide configured to deliver energy to a lumen of a subject can have a camera disposed on the distal end to visualize the lumen before and during administration in the body cavity. In this embodiment, the device can further include, e.g., an endoscope that contains the light guide therein and the imaging module thereon.

The display can include various features to guide a user (e.g., a clinician) during administration of therapeutic energy. For example, a distance between the UV source and the site of administration can be displayed in real time. The display can be coupled to the proximity determining element and/or the signal generating element to display a visual signal upon detection of the predetermined distance between the source and the site of administration. The visual signal can direct the user to administer the therapeutic energy upon detection of the predetermined distance.

Light-Emitting Contact Lens

The devices herein described can include a contact lens configured to direct UVC radiation to an eye of a subject. In some embodiments, the contact lens includes a source of UVC radiation (e.g., incorporated within the lens or attached to the lens). In some embodiments, the contact lens is configured to transmit UVC radiation to an eye of a subject from an external source of UVC radiation. In some embodiments, the source of UVC radiation is oriented towards the eye of a subject. In some embodiments, the source can be tunable to emit radiation at a selected wavelength. In some embodiments, the contact lens is configured to diffuse UVC radiation to illuminate the eye with a UVC beam having a substantially smooth and evenly distributed profile. The source of UVC radiation can include at least one light-emitting diode (LED) or a plurality of LEDs that emit the UV radiation (e.g., surface mounted device LEDs (SMDs)). For example, the source can include 1, 2, 3, 4, 5, 6, 7, 8, 9, 10, or more LEDs that emit UV radiation. In some embodiments, the UVC radiation can have a wavelength of from about 100 nm to about 280 nm (e.g., from about 200 nm to about 280 nm, e.g., from about 220 nm to about 280 nm, e.g., from about 240 nm to about 270 nm, e.g., from about 250 nm to about 270 or from about 260 nm to about 270 nm, e.g., about 254 nm, 255 nm, or about 265 nm). In some embodiments, the source of UV radiation produces a radiation intensity of from about 0.01 $mW/cm^2$ to about 500 $mW/cm^2$, e.g., from about 0.01 $mW/cm^2$ to about 50 $mW/cm^2$, e.g., from about 0.01 $mW/cm^2$ to about 5 $mW/cm^2$. For example the source of UV radiation can produce a radiation intensity of from about 0.01 $mW/cm^2$ to about 0.1 $mW/cm^2$, e.g., about 0.02 $mW/cm^2$, 0.03 $mW/cm^2$, 0.04 $mW/cm^2$, 0.05 $mW/cm^2$, 0.06 $mW/cm^2$, 0.07 $mW/cm^2$, 0.08 $mW/cm^2$, 0.09 $mW/cm^2$, 0.1 $mW/cm^2$, e.g., from about 0.1 $mW/cm^2$ to about 1 $mW/cm^2$, e.g., about 0.2 $mW/cm^2$, 0.3 $mW/cm^2$, 0.4 $mW/cm^2$, 0.5 $mW/cm^2$, 0.6 $mW/cm^2$, 0.7 $mW/cm^2$, 0.8 $mW/cm^2$, 0.9 $mW/cm^2$, or 1 $mW/cm^2$, e.g., from about 1 $mW/cm^2$ to about 10 $mW/cm^2$, e.g., about 2 $mW/cm^2$, 3 $mW/cm^2$, 4 $mW/cm^2$, 5 $mW/cm^2$, 6 $mW/cm^2$, 7 $mW/cm^2$, 8 $mW/cm^2$, 9 $mW/cm^2$, 10 $mW/cm^2$, e.g., about 10 $mW/cm^2$ to about 100 $mW/cm^2$, e.g., about 20 $mW/cm^2$, 30 $mW/cm^2$, 40 $mW/cm^2$, 50 $mW/cm^2$, 60 $mW/cm^2$, 70 $mW/cm^2$, 80 $mW/cm^2$, 90 $mW/cm^2$, or 100 $mW/cm^2$, e.g., from about 100 $mW/cm^2$ to about 500 $mW/cm^2$, e.g., about 150 $mW/cm^2$, 200 $mW/cm^2$, 250 $mW/cm^2$, 300 $mW/cm^2$, 350 $mW/cm^2$, 400 $mW/cm^2$, 450 $mW/cm^2$, or 500 $mW/cm^2$. The contact lens can include a separable or integral power source (e.g., a battery, an energy transfer antenna, a solar cell, an inertia power harvester, or an electrical plug). In some embodiments, the contact lens is composed of a plastic material (e.g., rigid gas permeable lens or hybrid lens). In some embodiments, the contact lens is composed of a soft material (e.g., soft lens). In some embodiments, the contact lens is composed of quartz (e.g., fused silica). In some embodiments, the contact lens is composed of a material that directs UVC radiation to a treatment site and blocks the UVC radiation from irradiating surrounding healthy tissue sites.

Additional Components

The devices described herein can further include additional elements that can be part of the device or separate from the device and provided as a kit or system. For example, a sterilization device can include a contact lens, a contact lens case or eyeglass case, e.g., configured to provide ultrasound and/or UV. The devices described herein can further include a temperature sensor. The heat source can be configured to provide a constant temperature (e.g., from about 30° C. to about 50° C., e.g., about 31° C. 32° C. 33° C., 34° C., 35° C., 36° C., 37° C., 38° C., 39° C., 40° C., 41° C., 42° C., 43° C., 44° C., 45° C., 46° C., 47° C., 48° C., 49° C., or 50° C., e.g., from about 38° C. to about 40° C., e.g., about 38.1° C. 38.2° C. 38.3° C., 38.4° C., 38.5° C., 38.6° C., 38.7° C., 38.8° C., 38.9° C., 39° C., 39.1° C., 39.2° C., 39.3° C., 39.4° C., 39.5° C., 39.6° C., 39.7° C., 39.8° C., 39.9° C., or 40° C. In some embodiments, the heat source provides a temperature of about 40° C. A device can optionally include a contact sensor that senses contact of the device with a site of treatment (e.g., an eyelid). A device can include a microprocessor. The contact sensor can include an IR contact sensing feedback emitter or sensor combination that signals to a microprocessor upon contact. This can be used to avoid UV transmission when not obscured by target tissue.

The device can include one or more power sources (e.g., battery), control button, handle or grip, or another ergonomic feature. In some embodiments, the devices are part of a system that includes a slit lamp. For example, the device can be configured to be reversibly mounted on a slit lamp, which can provide the source of energy (e.g., UV energy, e.g., UVC energy).

In one embodiment, a system is provided for delivering a plurality of energy sources to a tissue site. The system includes a base component, the base component having a proximal portion and a distal portion, the distal portion configured to mate with one of a plurality of interchangeable heads selected from two or more of a first head including a source of UVC radiation; a second head including a source of IR radiation; a third head including a source of ultrasound; a fourth head including a source of UVA radiation; a fifth head including a source of UVC radiation, a source of IR radiation, and a source of ultrasound; and a sixth head that includes a source of microwave radiation and a source of intense pulsed light. The first head can further include one or more of a proximity determining element configured to detect a predetermined distance between the energy source and a site of administration, a signal generating element configured to generate a signal upon detection of the predetermined distance by the proximity determining element, a module for aperture control to modulate the dose of energy, a light guide, and an imaging module. This system can be suitable for selecting a head component based on the desired use (e.g., method of treatment or sterilization technique).

Methods of Use

The device described herein can be used to treat a plurality of medical indications and/or can be used as a device for sterilization. The device, in some embodiments, can include one or more head components configured to deliver a combination of energy in the form of light, heat, and/or ultrasound.

Blepharitis and Meibomian Gland Disease

In some embodiments, the device herein described can be used as a therapeutic device to treat conditions related to the disfunction of meibomian glands such as blepharitis and meibomian gland disease (MGD). In some embodiments, the therapeutic device is configured to treat blepharitis and/or MGD, and the configuration includes the base component of the device and a head component that can include UVC light source, an IR light source, and a source of ultrasound. The device can provide heat, e.g., via the IR source of another source. In some embodiments, a therapy session using the therapeutic device can include irradiation of an affected eye with UVC light of a wavelength of from about 100 nm to about 280 nm (e.g., 105 nm to 275 nm, 110 nm to 270 nm, 115 nm to 265 nm, 120 nm to 260 nm, 125 nm to 255 nm, 130 nm to 250 nm, 135 nm to 245 nm, 140 nm to 240 nm, 145 nm to 235 nm, 150 nm to 230 nm, 155 nm to 225 nm, 160 nm to 220 nm, 165 nm to 215 nm, 170 nm to 210 nm, 175 nm to 205 nm, 180 nm to 200 nm, 185 nm to 195 nm, 101 nm, 102 nm, 103 nm, 104 nm, 105 nm, 106 nm, 107 nm, 108 nm, 109, 110 nm, 111 nm, 112 nm, 113 nm, 114 nm, 115 nm, 116 nm, 117 nm, 118 nm, 119, 120 nm, 121 nm, 122 nm, 123 nm, 124 nm, 125 nm, 126 nm, 127 nm, 128 nm, 129, 130 nm, 131 nm, 132 nm, 133 nm, 134 nm, 135 nm, 136 nm, 137 nm, 138 nm, 139, 140 nm, 141 nm, 142 nm, 143 nm, 144 nm, 145 nm, 146 nm, 147 nm, 148 nm, 149, 150 nm, 151 nm, 152 nm, 153 nm, 154 nm, 155 nm, 156 nm, 157 nm, 158 nm, 159, 160 nm, 161 nm, 162 nm, 163 nm, 164 nm, 165 nm, 166 nm, 167 nm, 168 nm, 169, 170 nm, 171 nm, 172 nm, 173 nm, 174 nm, 175 nm, 176 nm, 177 nm, 178 nm, 179, 180 nm, 181 nm, 182 nm, 183 nm, 184 nm, 185 nm, 186 nm, 187 nm, 188 nm, 189, 190 nm, 191 nm, 192 nm, 193 nm, 194 nm, 195 nm, 196 nm, 197 nm, 198 nm, 199, 200 nm, 201 nm, 202 nm, 203 nm, 204 nm, 205 nm, 206 nm, 207 nm, 208 nm, 209, 210 nm, 211 nm, 212 nm, 213 nm, 214 nm, 215 nm, 216 nm, 217 nm, 218 nm, 219, 220 nm, 221 nm, 222 nm, 223 nm, 224 nm, 225 nm, 226 nm, 227 nm, 228 nm, 229, 230 nm, 231 nm, 232 nm, 233 nm, 234 nm, 235 nm, 236 nm, 237 nm, 238 nm, 239, 240 nm, 241 nm, 242 nm, 243 nm, 244 nm, 245 nm, 246 nm, 247 nm, 248 nm, 249, 250 nm, 251 nm, 252 nm, 253 nm, 254 nm, 255 nm, 256 nm, 257 nm, 258 nm, 259, 260 nm, 261 nm, 262 nm, 263 nm, 264 nm, 265 nm, 266 nm, 267 nm, 268 nm, 269, 270 nm, 271 nm, 272 nm, 273 nm, 274 nm, 275 nm, 276 nm, 277 nm, 278 nm, 279, or 280 nm). In some embodiments, the UVC light has a power density of about 20 mW/cm$^2$ to about 1,000 mW/cm$^2$, e.g., about 30 mW/cm$^2$ to about 900 mW/cm$^2$, about 50 mW/cm$^2$ to about 850 mW/cm$^2$, about 100 mW/cm$^2$ to about 800 mW/cm$^2$, about 150 mW/cm$^2$ to about 750 mW/cm$^2$, about 200 mW/cm$^2$ to about 700 mW/cm$^2$, about 250 mW/cm$^2$ to about 650 mW/cm$^2$, about 300 mW/cm$^2$ to about 600 mW/cm$^2$, about 350 mW/cm$^2$ to about 550 mW/cm$^2$, about 400 mW/cm$^2$ to about 500 mW/cm$^2$, about 50 mW/cm$^2$, about 100 mW/cm$^2$, about 150 mW/cm$^2$, about 200 mW/cm$^2$, about 250 mW/cm$^2$, about 300 mW/cm$^2$, about 350 mW/cm$^2$, about 400 mW/cm$^2$, about 450 mW/cm$^2$, about 500 mW/cm$^2$, about 550 mW/cm$^2$, about 600 mW/cm$^2$, about 650 mW/cm$^2$, about 700 mW/cm$^2$, about 750 mW/cm$^2$, about 800 mW/cm$^2$, about 850 mW/cm$^2$, about 900 mW/cm$^2$, about 950 mW/cm$^2$, or about 1,000 mW/cm$^2$, and can be a continuous illumination or a pulsed illumination. In some embodiments, a therapy session can include irradiation of an affected eye with IR light of a wavelength of from about 750 nm and 1,000,000 nm (e.g., 760 nm to 900,000 nm, 770 nm to 800,000 nm, 780 nm to 700,000 nm, 790 nm to 600,000 nm, 800 to 500,000 nm, 810 nm to 400,000 nm, 820 nm to 300,000 nm, 830 nm to 200,000 nm, 840 nm to 100,000 nm, 850 nm to 90,000 nm, 860 nm to 80,000 nm, 870 nm to 70,000 nm, 880 nm to 60,000 nm, 890 nm to 50,000 nm, 900 nm to 40,000 nm, 1,000 nm to 30,000 nm, 1,100 nm to 20,000, 1,200 nm to 10,000, 1,300 nm to 5,000 nm, 1,400 nm to 4,000 nm, 1,500 nm to 3,000 nm, 1,600 nm to 2,500 nm, 1,700 nm to 2,400 nm, 1,800 nm to 2,300 nm, 1,900 nm to 2,200 nm, or 2,000 nm to 2,100 nm. In some embodiments, a treatment for blepharitis and/or MGD can require ultrasound of a frequency between about 1 MHz and about 10 MHz, e.g., 1 MHz, 2 MHz, 3 MHz, 4 MHz, 5 MHz, 6 MHz, 7 MHz, 8 MHz, 9 MHz, or 10 MHz, with an intensity of about 0.1 W/cm$^2$ to about 1.0 W/cm$^2$, e.g., 0.1 W/cm$^2$, 0.2 W/cm$^2$, 0.3 W/cm$^2$, 0.4 W/cm$^2$, 0.5 W/cm$^2$, 0.6 W/cm$^2$, 0.7 W/cm$^2$, 0.8 W/cm$^2$, 0.9 W/cm$^2$, or 1.0 W/cm$^2$. In some embodiments, the IR light has a power density of about 20 mW/cm$^2$ to about 1,000 mW/cm$^2$, e.g., about 30 mW/cm$^2$ to about 900 mW/cm$^2$, about 50 mW/cm$^2$ to about 850 mW/cm$^2$, about 100 mW/cm$^2$ to about 800 mW/cm$^2$, about 150 mW/cm$^2$ to about 750 mW/cm$^2$, about 200 mW/cm$^2$ to about 700 mW/cm$^2$, about 250 mW/cm$^2$ to about 650 mW/cm$^2$, about 300 mW/cm$^2$ to about 600 mW/cm$^2$, about 350 mW/cm$^2$ to about 550 mW/cm$^2$, about 400 mW/cm$^2$ to about 500 mW/cm$^2$, about 50 mW/cm$^2$, about 100 mW/cm$^2$, about 150 mW/cm$^2$, about 200 mW/cm$^2$, about 250 mW/cm$^2$, about 300 mW/cm$^2$, about 350 mW/cm$^2$, about 400 mW/cm$^2$, about 450 mW/cm$^2$, about 500 mW/cm$^2$, about 550 mW/cm$^2$, about 600 mW/cm$^2$, about 650 mW/cm$^2$, about 700 mW/cm$^2$, about 750 mW/cm$^2$, about 800 mW/cm$^2$, about 850 mW/cm$^2$, about 900 mW/cm$^2$, about 950 mW/cm$^2$, or about 1,000 mW/cm$^2$ and can be a continuous illumination or a pulsed illumination. In some embodiments, the treatment of blepharitis and/or MGD using the therapeutic device includes a plurality of treatment sessions (e.g., weekly, monthly, quarterly, semi-annually, or annually) and can include any combination of the previously described therapeutic procedures. In some embodiments, the therapeutic device is configured to deliver ultrasound with a transducer attached to a stainless-steel plate. In some embodiments, a physician delivering the treatment can use a contact footplate that controls the activation of the ultrasound, heating pad and UVC lights. In some embodiments, the distal end of the head component can include a contact sensing element that communicates with a microprocessor that controls the UVC lights. In further embodiments, the contact sensing element signals to the microprocessor whether there is contact with the treatment site in order to avoid any irradiation of surrounding healthy tissue with UVC light. When the contact sensor is activated it initiates, in some embodiments, the UVC irradiation and the ultrasound. In some embodiments, the device remains in contact after the irradiation with UVC to continue to deliver heat and ultrasound. In some embodiments, when the cycle of treatment is complete the ultrasound and heat deactivate, and the signal generator notifies the operator to remove the device. In further embodiments, whenever the device is prematurely removed from an eyelid all emission of light and ultrasound are paused until contact is resumed.

Cancer

In some embodiments, the device herein described can be used as a therapeutic device to treat cancer (e.g., leukemias, seminomas, melanomas, teratomas, lymphomas, neuroblastomas, gliomas, rectal cancer, endometrial cancer, kidney cancer, adrenal cancer, thyroid cancer, blood cancer, skin cancer, brain cancer, cervical cancer, intestinal cancer, liver cancer, colon cancer, stomach cancer, intestine cancer, head and neck cancer, gastrointestinal cancer, lymph node cancer, esophageal cancer, colorectal cancer, pancreatic cancer, ear, nose and throat cancer (ENT), breast cancer, prostate cancer, uterine cancer, ovarian cancer, and lung cancer and their metastases. Examples thereof are lung carcinomas, breast carcinomas, prostate carcinomas, colon carcinomas, renal cell carcinomas, cervical carcinomas, or metastases from the types of cancer or tumors described above) and/or to provide adjunctive treatment. In some embodiments, the devices and methods may be used to treat a caner, neoplasia, and/or dysplasia, e.g., including cancerous or precancerous cells. In some embodiments, the therapeutic device is configured to treat cancer, and the configuration includes the base component of the device and a head component that can include a UVC light source. The device can also include a proximity determining element and a signal generating element. In some embodiments, the device further includes light guide and/or an imaging module. In some embodiments, a therapy session using the therapeutic device can include irradiation of an affected site with UVC light of a wavelength of from about 100 nm to about 280 nm (e.g., 105 nm to 275 nm, 110 nm to 270 nm, 115 nm to 265 nm, 120 nm to 260 nm, 125 nm to 255 nm, 130 nm to 250 nm, 135 nm to 245 nm, 140 nm to 240 nm, 145 nm to 235 nm, 150 nm to 230 nm, 155 nm to 225 nm, 160 nm to 220 nm, 165 nm to 215 nm, 170 nm to 210 nm, 175 nm to 205 nm, 180 nm to 200 nm, 185 nm to 195 nm, 101 nm, 102 nm, 103 nm, 104 nm, 105 nm, 106 nm, 107 nm, 108 nm, 109, 110 nm, 111 nm, 112 nm, 113 nm, 114 nm, 115 nm, 116 nm, 117 nm, 118 nm, 119, 120 nm, 121 nm, 122 nm, 123 nm, 124 nm, 125 nm, 126 nm, 127 nm, 128 nm, 129, 130 nm, 131 nm, 132 nm, 133 nm, 134 nm, 135 nm, 136 nm, 137 nm, 138 nm, 139, 140 nm, 141 nm, 142 nm, 143 nm, 144 nm, 145 nm, 146 nm, 147 nm, 148 nm, 149, 150 nm, 151 nm, 152 nm, 153 nm, 154 nm, 155 nm, 156 nm, 157 nm, 158 nm, 159, 160 nm, 161 nm, 162 nm, 163 nm, 164 nm, 165 nm, 166 nm, 167 nm, 168 nm, 169, 170 nm, 171 nm, 172 nm, 173 nm, 174 nm, 175 nm, 176 nm, 177 nm, 178 nm, 179, 180 nm, 181 nm, 182 nm, 183 nm, 184 nm, 185 nm, 186 nm, 187 nm, 188 nm, 189, 190 nm, 191 nm, 192 nm, 193 nm, 194 nm, 195 nm, 196 nm, 197 nm, 198 nm, 199, 200 nm, 201 nm, 202 nm, 203 nm, 204 nm, 205 nm, 206 nm, 207 nm, 208 nm, 209, 210 nm, 211 nm, 212 nm, 213 nm, 214 nm, 215 nm, 216 nm, 217 nm, 218 nm, 219, 220 nm, 221 nm, 222 nm, 223 nm, 224 nm, 225 nm, 226 nm, 227 nm, 228 nm, 229, 230 nm, 231 nm, 232 nm, 233 nm, 234 nm, 235 nm, 236 nm, 237 nm, 238 nm, 239, 240 nm, 241 nm, 242 nm, 243 nm, 244 nm, 245 nm, 246 nm, 247 nm, 248 nm, 249, 250 nm, 251 nm, 252 nm, 253 nm, 254 nm, 255 nm, 256 nm, 257 nm, 258 nm, 259, 260 nm, 261 nm, 262 nm, 263 nm, 264 nm, 265 nm, 266 nm, 267 nm, 268 nm, 269, 270 nm, 271 nm, 272 nm, 273 nm, 274 nm, 275 nm, 276 nm, 277 nm, 278 nm, 279, or 280 nm). In some embodiments, the UVC light has a power density of about 20 mW/cm$^2$ to about 1,000 mW/cm$^2$, e.g., about 30 mW/cm$^2$ to about 900 mW/cm$^2$, about 50 mW/cm$^2$ to about 850 mW/cm$^2$, about 100 mW/cm$^2$ to about 800 mW/cm$^2$, about 150 mW/cm$^2$ to about 750 mW/cm$^2$, about 200 mW/cm$^2$ to about 700 mW/cm$^2$, about 250 mW/cm$^2$ to about 650 mW/cm$^2$, about 300 mW/cm$^2$ to about 600 mW/cm$^2$, about 350 mW/cm$^2$ to about 550 mW/cm$^2$, about 400 mW/cm$^2$ to about 500 mW/cm$^2$, about 50 mW/cm$^2$, about 100 mW/cm$^2$, about 150 mW/cm$^2$, about 200 mW/cm$^2$, about 250 mW/cm$^2$, about 300 mW/cm$^2$, about 350 mW/cm$^2$, about 400 mW/cm$^2$, about 450 mW/cm$^2$, about 500 mW/cm$^2$, about 550 mW/cm$^2$, about 600 mW/cm$^2$, about 650 mW/cm$^2$, about 700 mW/cm$^2$, about 750 mW/cm$^2$, about 800 mW/cm$^2$, about 850 mW/cm$^2$, about 900 mW/cm$^2$, about 950 mW/cm$^2$, or about 1,000 mW/cm$^2$ and can be a continuous illumination or a pulsed illumination. In some embodiments, a treatment for cancer can be a continuous illumination or a pulsed illumination. In some embodiments, where the illumination is pulsed, the pulse frequency can be from about 20 Hz to about 1,000 Hz, e.g., about 50 Hz to about 950 Hz, about 100 Hz to about 900 Hz, about 150 Hz to about 850 Hz, about 200 Hz to about 800 Hz, about 250 Hz to about 750 Hz, about 300 Hz to about 700 Hz, about 350 Hz to about 650 Hz, about 400 Hz to about 600 Hz, about 450 Hz to about 550 Hz, about 500 Hz to about 525 Hz, about 50 Hz, about 100 Hz, about 150 Hz, about 200 Hz, about 250 Hz, about 300 Hz, about 350 Hz, about 400 Hz, about 450 Hz, about 500 Hz, about 550 Hz, about 600 Hz, about 650 Hz, about 700 Hz, about 750 Hz, about 800 Hz, about 850 Hz, about 900 Hz, about 950 Hz, about 1,000 Hz, with a duty cycle of 1-100% (e.g., 10%, 20%, 30%, 40%, 50%, 60%, 70%, 80%, 90%, 100%). In some embodiments, the treatment of cancer using the device can include a plurality of treatment sessions and can include any combination of the previously described therapeutic procedures. In further embodiments the illumination can be controlled with a footplate. In some embodiments, the proximity determining element is connected to the light guide and communicates with a microprocessor that controls the irradiation. In some embodiments, the irradiation is only activated when the output end of the light guide reaches a predetermined distance from the treatment site. In some embodiments, when the cycle of treatment is complete the UVC sources deactivate, and a signal generator notifies the operator to remove the device. In further embodiments, whenever the device is prematurely removed from a treatment site all emission of light and paused until the predetermined distance is restored.

Ocular, Orbital, and/or Adnexal Cancer

In some embodiments, the device herein described can be used as a therapeutic device to treat eye, orbital, and/or adnexal cancer (e.g., intraocular secondary tumors, retinoblastoma, uveal melanomas, conjunctival melanomas, orbital cancers, eyelid cancers, or adnexal cancers) and/or to provide adjunctive treatment. In some embodiments, the therapeutic device is configured to treat ocular cancer, and the configuration includes the base component of the device and a head component that can include a UVC light source. The device can also include a proximity determining element and a signal generating element. In some embodiments, the device further includes light guide and/or an imaging module. In some embodiments, the device is the contact lens herein described and is used to deliver a therapeutic dose of UVC to an eye to treat ocular cancer. In some embodiments, a therapy session using the therapeutic device can include irradiation of an affected eye with UVC light of a wavelength of from about 100 nm to about 280 nm (e.g., 105 nm to 275 nm, 110 nm to 270 nm, 115 nm to 265 nm, 120 nm to 260 nm, 125 nm to 255 nm, 130 nm to 250 nm, 135 nm to 245 nm, 140 nm to 240 nm, 145 nm to 235 nm, 150 nm to 230 nm, 155 nm to 225 nm, 160 nm to 220 nm, 165 nm to 215 nm, 170 nm to 210 nm, 175 nm to 205 nm, 180 nm to 200 nm, 185 nm to 195 nm, 101 nm, 102 nm, 103 nm, 104 nm, 105 nm, 106 nm, 107 nm, 108 nm, 109, 110 nm, 111 nm, 112 nm, 113 nm, 114 nm, 115 nm, 116 nm, 117 nm, 118 nm, 119, 120 nm, 121 nm, 122 nm, 123 nm, 124 nm, 125 nm, 126 nm, 127 nm, 128 nm, 129, 130 nm, 131 nm, 132 nm, 133 nm, 134 nm, 135 nm, 136 nm, 137 nm, 138 nm, 139, 140 nm, 141 nm, 142 nm, 143 nm, 144 nm, 145 nm, 146 nm, 147 nm, 148 nm, 149, 150 nm, 151 nm, 152 nm, 153 nm, 154 nm, 155 nm, 156 nm, 157 nm, 158 nm, 159, 160 nm, 161 nm, 162 nm, 163 nm, 164 nm, 165 nm, 166 nm, 167 nm, 168 nm, 169, 170 nm, 171 nm, 172 nm, 173 nm, 174 nm, 175 nm, 176 nm, 177 nm, 178 nm, 179, 180 nm, 181 nm, 182 nm, 183 nm, 184 nm, 185 nm, 186 nm, 187 nm, 188 nm, 189, 190 nm, 191 nm, 192 nm, 193 nm, 194 nm, 195 nm, 196 nm, 197 nm, 198 nm, 199, 200 nm, 201 nm, 202 nm, 203 nm, 204 nm, 205 nm, 206 nm, 207 nm, 208 nm, 209, 210 nm, 211 nm, 212 nm, 213 nm, 214 nm, 215 nm, 216 nm, 217 nm, 218 nm, 219, 220 nm, 221 nm, 222 nm, 223 nm, 224 nm, 225 nm, 226 nm, 227 nm, 228 nm, 229, 230 nm, 231 nm, 232 nm, 233 nm, 234 nm, 235 nm, 236 nm, 237 nm, 238 nm, 239, 240 nm, 241 nm, 242 nm, 243 nm, 244 nm, 245 nm, 246 nm, 247 nm, 248 nm, 249, 250 nm, 251 nm, 252 nm, 253 nm, 254 nm, 255 nm, 256 nm, 257 nm, 258 nm, 259, 260 nm, 261 nm, 262 nm, 263 nm, 264 nm, 265 nm, 266 nm, 267 nm, 268 nm, 269, 270 nm, 271 nm, 272 nm, 273 nm, 274 nm, 275 nm, 276 nm, 277 nm, 278 nm, 279, or 280 nm). In some embodiments, the UVC light has a power density of about 20 mW/cm$^2$ to about 1,000 mW/cm$^2$, e.g., about 30 mW/cm$^2$ to about 900 mW/cm$^2$, about 50 mW/cm$^2$ to about 850 mW/cm$^2$, about 100 mW/cm$^2$ to about 800 mW/cm$^2$, about 150 mW/cm$^2$ to about 750 mW/cm$^2$, about 200 mW/cm$^2$ to about 700 mW/cm$^2$, about 250 mW/cm$^2$ to about 650 mW/cm$^2$, about 300 mW/cm$^2$ to about 600 mW/cm$^2$, about 350 mW/cm$^2$ to about 550 mW/cm$^2$, about 400 mW/cm$^2$ to about 500 mW/cm$^2$, about 50 mW/cm$^2$, about 100 mW/cm$^2$, about 150 mW/cm$^2$, about 200 mW/cm$^2$, about 250 mW/cm$^2$, about 300 mW/cm$^2$, about 350 mW/cm$^2$, about 400 mW/cm$^2$, about 450 mW/cm$^2$, about 500 mW/cm$^2$, about 550 mW/cm$^2$, about 600 mW/cm$^2$, about 650 mW/cm$^2$, about 700 mW/cm$^2$, about 750 mW/cm$^2$, about 800 mW/cm$^2$, about 850 mW/cm$^2$, about 900 mW/cm$^2$, about 950 mW/cm$^2$, or about 1,000 mW/cm$^2$ and can be a continuous illumination or a pulsed illumination. In some embodiments, a treatment for ocular cancer can be a continuous illumination or a pulsed illumination. In some embodiments, where the illumination is pulsed, the pulse frequency can be from about 20 Hz to about 1,000 Hz, e.g., about 50 Hz to about 950 Hz, about 100 Hz to about 900 Hz, about 150 Hz to about 850 Hz, about 200 Hz to about 800 Hz, about 250 Hz to about 750 Hz, about 300 Hz to about 700 Hz, about 350 Hz to about 650 Hz, about 400 Hz to about 600 Hz, about 450 Hz to about 550 Hz, about 500 Hz to about 525 Hz, about 50 Hz, about 100 Hz, about 150 Hz, about 200 Hz, about 250 Hz, about 300 Hz, about 350 Hz, about 400 Hz, about 450 Hz, about 500 Hz, about 550 Hz, about 600 Hz, about 650 Hz, about 700 Hz, about 750 Hz, about 800 Hz, about 850 Hz, about 900 Hz, about 950 Hz, about 1,000 Hz, with a duty cycle of 1-100% (e.g., 10%, 20%, 30%, 40%, 50%, 60%, 70%, 80%, 90%, 100%). In some embodiments, the treatment of an ocular cancer using the device can include a plurality of treatment sessions and can include any combination of the previously described therapeutic procedures. In some embodiments, the therapeutic device can be mounted onto a slit lamp apparatus. In further embodiments the illumination can be controlled with a footplate. In further embodiments an ocular cancer can be an intraocular, a surface of the eye, an eyelid, or an orbital cancer. In some embodiments, the light guide can be introduced into the internal space of an eye to irradiate an intraocular or orbital cancer with a therapeutic dose of UVC radiation. In some embodiments, the proximity determining element is connected to the light guide and communicates with a microprocessor that controls the irradiation. In some embodiments, the irradiation is only activated when the output end of the light guide reaches a predetermined distance from the treatment site. In some embodiments, when the cycle of treatment is complete the UVC sources deactivate, and a signal generator notifies the operator to remove the device. In further embodiments, whenever the device is prematurely removed from a treatment site all emission of light and paused until the predetermined distance is restored.

Acne Vulgaris and Acne Rosacea

In some embodiments, the device herein described can be used as a therapeutic device to treat acne vulgaris and/or acne rosacea. In some embodiments, the therapeutic device is configured to treat acne, and the configuration includes the base component of the device and a head component that can include a UVC light source, a proximity determining element, and a light guide. In some embodiments, a therapy session using the device can include irradiation of an affected skin area with UVC light of a wavelength between 100 nm and 280 nm (e.g., 105 nm to 275 nm, 110 nm to 270 nm, 115 nm to 265 nm, 120 nm to 260 nm, 125 nm to 255 nm, 130 nm to 250 nm, 135 nm to 245 nm, 140 nm to 240 nm, 145 nm to 235 nm, 150 nm to 230 nm, 155 nm to 225 nm, 160 nm to 220 nm, 165 nm to 215 nm, 170 nm to 210 nm, 175 nm to 205 nm, 180 nm to 200 nm, 185 nm to 195 nm, 101 nm, 102 nm, 103 nm, 104 nm, 105 nm, 106 nm, 107 nm, 108 nm, 109, 110 nm, 111 nm, 112 nm, 113 nm, 114 nm, 115 nm, 116 nm, 117 nm, 118 nm, 119, 120 nm, 121 nm, 122 nm, 123 nm, 124 nm, 125 nm, 126 nm, 127 nm, 128 nm, 129, 130 nm, 131 nm, 132 nm, 133 nm, 134 nm, 135 nm, 136 nm, 137 nm, 138 nm, 139, 140 nm, 141 nm, 142 nm, 143 nm, 144 nm, 145 nm, 146 nm, 147 nm, 148 nm, 149, 150 nm, 151 nm, 152 nm, 153 nm, 154 nm, 155 nm, 156 nm, 157 nm, 158 nm, 159, 160 nm, 161 nm, 162 nm, 163 nm, 164 nm, 165 nm, 166 nm, 167 nm, 168 nm, 169, 170 nm, 171 nm, 172 nm, 173 nm, 174 nm, 175 nm, 176 nm, 177 nm, 178 nm, 179, 180 nm, 181 nm, 182 nm, 183 nm, 184 nm, 185 nm, 186 nm, 187 nm, 188 nm, 189, 190 nm, 191 nm, 192 nm, 193 nm, 194 nm, 195 nm, 196 nm, 197 nm, 198 nm, 199, 200 nm, 201 nm, 202 nm, 203 nm, 204 nm, 205 nm, 206 nm, 207 nm, 208 nm, 209, 210 nm, 211 nm, 212 nm, 213 nm, 214 nm, 215 nm, 216 nm, 217 nm, 218 nm, 219, 220 nm, 221 nm, 222 nm, 223 nm, 224 nm, 225 nm, 226 nm, 227 nm, 228 nm, 229, 230 nm, 231 nm, 232 nm, 233 nm, 234 nm, 235 nm, 236 nm, 237 nm, 238 nm, 239, 240 nm, 241 nm, 242 nm, 243 nm, 244 nm, 245 nm, 246 nm, 247 nm, 248 nm, 249, 250 nm, 251 nm, 252 nm, 253 nm, 254 nm, 255 nm, 256 nm, 257 nm, 258 nm, 259, 260 nm, 261 nm, 262 nm, 263 nm, 264 nm, 265 nm, 266 nm, 267 nm, 268 nm, 269, 270 nm, 271 nm, 272 nm, 273 nm, 274 nm, 275 nm, 276 nm, 277 nm, 278 nm, 279, or 280 nm). In some embodiments, the UVC light has a power density of about 20 mW/cm$^2$ to about 1,000 mW/cm$^2$, e.g., about 30 mW/cm$^2$ to about 900 mW/cm$^2$, about 50 mW/cm$^2$ to about 850 mW/cm$^2$, about 100 mW/cm$^2$ to about 800 mW/cm$^2$, about 150 mW/cm$^2$ to about 750 mW/cm$^2$, about 200 mW/cm$^2$ to about 700 mW/cm$^2$, about 250 mW/cm$^2$ to about 650 mW/cm$^2$, about 300 mW/cm$^2$ to about 600 mW/cm$^2$, about 350 mW/cm$^2$ to about 550 mW/cm$^2$, about 400 mW/cm$^2$ to about 500 mW/cm$^2$, about 50 mW/cm$^2$, about 100 mW/cm$^2$, about 150 mW/cm$^2$, about 200 mW/cm$^2$, about 250 mW/cm$^2$, about 300 mW/cm$^2$, about 350 mW/cm$^2$, about 400 mW/cm$^2$, about 450 mW/cm$^2$, about 500 mW/cm$^2$, about 550 mW/cm$^2$, about 600 mW/cm$^2$, about 650 mW/cm$^2$, about 700 mW/cm$^2$, about 750 mW/cm$^2$, about 800 mW/cm$^2$, about 850 mW/cm$^2$, about 900 mW/cm$^2$, about 950 mW/cm$^2$, or about 1,000 mW/cm$^2$ and can be a continuous illumination or a pulsed illumination. In some embodiments, a treatment for acne can be a continuous illumination or a pulsed illumination. In some embodiments, where the illumination is pulsed, the pulse frequency can be from about 20 Hz to about 1,000 Hz, e.g., about 50 Hz to about 950 Hz, about 100 Hz to about 900 Hz, about 150 Hz to about 850 Hz, about 200 Hz to about 800 Hz, about 250 Hz to about 750 Hz, about 300 Hz to about 700 Hz, about 350 Hz to about 650 Hz, about 400 Hz to about 600 Hz, about 450 Hz to about 550 Hz, about 500 Hz to about 525 Hz, about 50 Hz, about 100 Hz, about 150 Hz, about 200 Hz, about 250 Hz, about 300 Hz, about 350 Hz, about 400 Hz, about 450 Hz, about 500 Hz, about 550 Hz, about 600 Hz, about 650 Hz, about 700 Hz, about 750 Hz, about 800 Hz, about 850 Hz, about 900 Hz, about 950 Hz, about 1,000 Hz, with a duty cycle of 1-100% (e.g., 10%, 20%, 30%, 40%, 50%, 60%, 70%, 80%, 90%, 100%). In some embodiments, the treatment of acne using the device can include a plurality of treatment sessions (e.g., weekly, monthly, quarterly, semi-annually, or annually) and can include any combination of the previously described therapeutic procedures. In some embodiments, the therapeutic device can be mounted onto a slit lamp apparatus. In further embodiments the illumination can be controlled with a footplate. In some embodiments, the light guide can be directed to an affected area of skin to irradiate with a therapeutic dose of UVC radiation. In some embodiments, the proximity determining element is connected to the light guide and communicates with a microprocessor that controls the irradiation. In some embodiments, the irradiation is only activated when the output end of the light guide reaches a predetermined distance from the treatment site. In some embodiments, when the cycle of treatment is complete the UVC sources deactivate, and a signal generator notifies the operator to remove the device. In further embodiments, whenever the device is prematurely removed from a treatment site all emission of light is paused until the predetermined distance is restored.

Wound Healing (e.g., Gastric or Duodenal Ulcers)

In some embodiments, the device herein described can be used as a therapeutic device to treat wounds and to improve wound healing (e.g., speed of healing, degree of healing, and/or reduction of scarring). In some embodiments, the device is configured to treat gastric or duodenal ulcers (e.g., resulting from an *H. pylori* infection), abrasions, surgical incisions, recurrent corneal erosions, corneal ulcers, infections, burns, eyelid and skin trauma, trauma or abrasion caused by a foreign body, cosmetic surgery, blepharoplasty, cataract surgery incisions, refractive surgery incisions and/or flaps, puncture wounds, suture related inflammation, rotation flaps, pedicle flaps, or skin grafts. In some embodiments, the therapeutic device is configured to treat gastric or duodenal ulcers, and the configuration includes the base component of the device and a head component that can include a UV source, a proximity determining element, and a light guide. In some embodiments, a therapy session using the wound healing configuration (e.g., gastric or duodenal ulcers configuration) of the therapeutic device can include irradiation of an affected wound (e.g., gastric or duodenal tissue area) with UVC light of a wavelength between 100 nm and 280 nm (e.g., 105 nm to 275 nm, 110 nm to 270 nm, 115 nm to 265 nm, 120 nm to 260 nm, 125 nm to 255 nm, 130 nm to 250 nm, 135 nm to 245 nm, 140 nm to 240 nm, 145 nm to 235 nm, 150 nm to 230 nm, 155 nm to 225 nm, 160 nm to 220 nm, 165 nm to 215 nm, 170 nm to 210 nm, 175 nm to 205 nm, 180 nm to 200 nm, 185 nm to 195 nm, 101 nm, 102 nm, 103 nm, 104 nm, 105 nm, 106 nm, 107 nm, 108 nm, 109, 110 nm, 111 nm, 112 nm, 113 nm, 114 nm, 115 nm, 116 nm, 117 nm, 118 nm, 119, 120 nm, 121 nm, 122 nm, 123 nm, 124 nm, 125 nm, 126 nm, 127 nm, 128 nm, 129, 130 nm, 131 nm, 132 nm, 133 nm, 134 nm, 135 nm, 136 nm, 137 nm, 138 nm, 139, 140 nm, 141 nm, 142 nm, 143 nm, 144 nm, 145 nm, 146 nm, 147 nm, 148 nm, 149, 150 nm, 151 nm, 152 nm, 153 nm, 154 nm, 155 nm, 156 nm, 157 nm, 158 nm, 159, 160 nm, 161 nm, 162 nm, 163 nm, 164 nm, 165 nm, 166 nm, 167 nm, 168 nm, 169, 170 nm, 171 nm, 172 nm, 173 nm, 174 nm, 175 nm, 176 nm, 177 nm, 178 nm, 179, 180 nm, 181 nm, 182 nm, 183 nm, 184 nm, 185 nm, 186 nm, 187 nm, 188 nm, 189, 190 nm, 191 nm, 192 nm, 193 nm, 194 nm, 195 nm, 196 nm, 197 nm, 198 nm, 199, 200 nm, 201 nm, 202 nm, 203 nm, 204 nm, 205 nm, 206 nm, 207 nm, 208 nm, 209, 210 nm, 211 nm, 212 nm, 213 nm, 214 nm, 215 nm, 216 nm, 217 nm, 218 nm, 219, 220 nm, 221 nm, 222 nm, 223 nm, 224 nm, 225 nm, 226 nm, 227 nm, 228 nm, 229, 230 nm, 231 nm, 232 nm, 233 nm, 234 nm, 235 nm, 236 nm, 237 nm, 238 nm, 239, 240 nm, 241 nm, 242 nm, 243 nm, 244 nm, 245 nm, 246 nm, 247 nm, 248 nm, 249, 250 nm, 251 nm, 252 nm, 253 nm, 254 nm, 255 nm, 256 nm, 257 nm, 258 nm, 259, 260 nm, 261 nm, 262 nm, 263 nm, 264 nm, 265 nm, 266 nm, 267 nm, 268 nm, 269, 270 nm, 271 nm, 272 nm, 273 nm, 274 nm, 275 nm, 276 nm, 277 nm, 278 nm, 279, or 280 nm). In some embodiments, the UVC light has a power density of from about 1 mJ/cm$^2$ to about 5000 mJ/cm$^2$, e.g., from about 50 mJ/cm$^2$ to about 4500 mJ/cm$^2$, from about 100 mJ/cm$^2$ to about 4000 mJ/cm$^2$, from about 200 mJ/cm$^2$ to about 4000 mJ/cm$^2$, from about 300 mJ/cm$^2$ to about 3500 mJ/cm$^2$, from about 500 mJ/cm$^2$ to about 3000 mJ/cm$^2$, from about 1,000 mJ/cm$^2$ to about 2500 mJ/cm$^2$, from about 1500 mJ/cm$^2$ to about 2000 mJ/cm$^2$, about 100 mJ/cm$^2$, about 200 mJ/cm$^2$, about 300 mJ/cm$^2$, about 400 mJ/cm$^2$, about 500 mJ/cm$^2$, about 600 mJ/cm$^2$, about 700 mJ/cm$^2$, about 800 mJ/cm$^2$, about 900 mJ/cm$^2$, about 1,000 mJ/cm$^2$, about 1500 mJ/cm$^2$, about 2000 mJ/cm$^2$, about 2500 mJ/cm$^2$, about 3000 mJ/cm$^2$, about 3500 mJ/cm$^2$, about 4000 mJ/cm$^2$, about 4500 mJ/cm$^2$, about 5000 mJ/cm$^2$, and can be a continuous illumination or a pulsed illumination. In some embodiments, the source of UVC light can be an LED with an optical output between 0.2 mW to 0.3 mW. In some embodiments the intensity of UVC LED light on a target tissue (e.g., wound) can depend on the area of target tissue irradiated (e.g., for a target tissue area of about 1 cm$^2$ the intensity is about 0.3 mW/cm$^2$, and for a target tissue area of about 4.3 mm$^2$ the intensity is about 2.07 mW/cm$^2$. In some embodiments, the total UVC dose on a target tissue depends on the duration of the illumination session (e.g., for a target tissue with an area of about 4.3 mm$^2$ the intensity is about 2.07 mW/cm$^2$ and over the duration of 15 seconds the total UVC dose is about 31 mJ/cm$^2$). In some embodiments, where the illumination is pulsed, the pulse frequency can be from the pulse frequency can be from about 20 Hz to about 1,000 Hz, e.g., about 50 Hz to about 950 Hz, about 100 Hz to about 900 Hz, about 150 Hz to about 850 Hz, about 200 Hz to about 800 Hz, about 250 Hz to about 750 Hz, about 300 Hz to about 700 Hz, about 350 Hz to about 650 Hz, about 400 Hz to about 600 Hz, about 450 Hz to about 550 Hz, about 500 Hz to about 525 Hz, about 50 Hz, about 100 Hz, about 150 Hz, about 200 Hz, about 250 Hz, about 300 Hz, about 350 Hz, about 400 Hz, about 450 Hz, about 500 Hz, about 550 Hz, about 600 Hz, about 650 Hz, about 700 Hz, about 750 Hz, about 800 Hz, about 850 Hz, about 900 Hz, about 950 Hz, about 1,000 Hz, with a duty cycle of 1-100% (e.g., 10%, 20%, 30%, 40%, 50%, 60%, 70%, 80%, 90%, 100%). In some embodiments, the treatment of a wound or a gastric or duodenal ulcer can include a plurality of treatment sessions (e.g., weekly, monthly, quarterly, semi-annually, or annually) and can include any combination of the previously described therapeutic procedures. In further embodiments the illumination can be controlled with a footplate. In some embodiments, the light guide can be introduced into or positioned close to an affected area of an internal wound (e.g., a wound of the gastrointestinal tract) to irradiate with a therapeutic dose of UVC radiation. In some embodiments, the proximity determining element is connected to the light guide and communicates with a microprocessor that controls the irradiation. In some embodiments, the irradiation is only activated when the output end of the light guide reaches a predetermined distance from the treatment site. In some embodiments, when the cycle of treatment is complete the UVC sources deactivate, and a signal generator notifies the operator to remove the device. In further embodiments, whenever the device is prematurely removed from a treatment site all emission of light is paused until the predetermined distance is restored. The method of treating wounds by delivering a therapeutic dose of UVC radiation can incorporate any combination of UVC and the other energy sources herein described (e.g., IR radiation, UVA radiation, microwave, and/or ultrasound).

Sterilization and/or Reduction of Harmful Microorganism Load of Tissue

In some embodiments, the device herein described can be used as a sterilization device to sterilize tissues or reduce the microorganismal (e.g., viral, bacterial, protozoal, commensal, parasitic, fungal, nematode, viroid, or any combination thereof) load in the tissue. In some embodiments, the sterilization device can reduce the microorganismal load (e.g., infections of *Chlamydia* trachomatous, infections of *Demodex folliculorum*, endophthalmitis, bacterial conjunctivitis, adenoviral conjunctivitis, herpes viruses, human papilloma virus, coronaviruses e.g., SARS-CoV-2). In some embodiments, the sterilization device is configured to sterilize a tissue (e.g., internal region of the mouth e.g., to treat periodontitis, and/or to treat gingivitis, external region of the mouth e.g., lips, nasal cavity, oropharyngeal cavity, genital lumen, urinary lumen, gastrointestinal tract, exterior region of the eye, interior region of the eye, ear, genitalia, body lumen) and the configuration includes the base component of the device and a head component that can include a UV source, a proximity determining element, and a light guide. In some embodiments, the device is configured to sterilize and/or reduce the load (e.g., by at least 5%, 10%, 20%, 30%, 40%, 50%, 60%, 70%, 80%, 90%, 95%, 97%, 99%, or 100%) of harmful microorganisms in an infection of a tooth or in a tooth cavity. In some embodiments, the device, is configured to sterilize an internal region of the mouth (e.g., a tooth, a cavity of a tooth, and/or a region surrounding a tooth), e.g., during the process of a root canal procedure. In some embodiments, the device includes a contact lens as herein described to deliver a therapeutic dose of UVC to an eye to sterilize or reduce the viral and/or bacterial load on the eye. In some embodiments, the device is configured to treat gingivitis and includes a shield shaped to deliver the therapeutic dose or UVC to the gum tissue of the subject and prevent UVC from being delivered outside of the gum tissue. In some embodiments, the source of UVC radiation is configured to deliver a therapeutic dose of UVC radiation to an anterior region, a posterior region, a vitreous chamber region, a retinal region, a choroidal region, a macular region, a lens region (e.g., an intraocular lens region), a ciliary muscle region, or an optic nerve region of the eye. In some embodiments, the therapeutic dose of UVC is delivered to the eye of the subject through a vitrectomy element. In some embodiments, the source of UVC radiation is configured to be inserted into the vitrectomy element and transmit the therapeutic dose of UVC radiation directly into the eye of the subject. In some embodiments, the source of UVC radiation is configured to transmit the therapeutic dose of UVC radiation through the vitrectomy element using a light guide. In some embodiments the light guide (e.g., a vitreous probe) has a diameter of from about 1 mm to about 20 mm (e.g., from about 2 mm to about 19 mm, from about 3 mm to about 18 mm, from about 4 mm to about 17 mm, from about 5 mm to about 16 mm, from about 6 mm to about 15 mm, from about 7 mm to about 14 mm, from about 8 mm to about 13 mm, from about 9 mm to about 12 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, or about 20 mm). In some embodiments, the light guide has a length (e.g., vitreous probe length) of from about 1 mm to about 20 mm (e.g., from about 2 mm to about 19 mm, from about 3 mm to about 18 mm, from about 4 mm to about 17 mm, from about 5 mm to about 16 mm, from about 6 mm to about 15 mm, from about 7 mm to about 14 mm, from about 8 mm to about 13 mm, from about 9 mm to about 12 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, or about 20 mm). In some embodiments, a sterilizing session using the device can include irradiation of an affected tissue area with UVC light of a wavelength between 100 nm and 280 nm (e.g., 105 nm to 275 nm, 110 nm to 270 nm, 115 nm to 265 nm, 120 nm to 260 nm, 125 nm to 255 nm, 130 nm to 250 nm, 135 nm to 245 nm, 140 nm to 240 nm, 145 nm to 235 nm, 150 nm to 230 nm, 155 nm to 225 nm, 160 nm to 220 nm, 165 nm to 215 nm, 170 nm to 210 nm, 175 nm to 205 nm, 180 nm to 200 nm, 185 nm to 195 nm, 101 nm, 102 nm, 103 nm, 104 nm, 105 nm, 106 nm, 107 nm, 108 nm, 109, 110 nm, 111 nm, 112 nm, 113 nm, 114 nm, 115 nm, 116 nm, 117 nm, 118 nm, 119, 120 nm, 121 nm, 122 nm, 123 nm, 124 nm, 125 nm, 126 nm, 127 nm, 128 nm, 129, 130 nm, 131 nm, 132 nm, 133 nm, 134 nm, 135 nm, 136 nm, 137 nm, 138 nm, 139, 140 nm, 141 nm, 142 nm, 143 nm, 144 nm, 145 nm, 146 nm, 147 nm, 148 nm, 149, 150 nm, 151 nm, 152 nm, 153 nm, 154 nm, 155 nm, 156 nm, 157 nm, 158 nm, 159, 160 nm, 161 nm, 162 nm, 163 nm, 164 nm, 165 nm, 166 nm, 167 nm, 168 nm, 169, 170 nm, 171 nm, 172 nm, 173 nm, 174 nm, 175 nm, 176 nm, 177 nm, 178 nm, 179, 180 nm, 181 nm, 182 nm, 183 nm, 184 nm, 185 nm, 186 nm, 187 nm, 188 nm, 189, 190 nm, 191 nm, 192 nm, 193 nm, 194 nm, 195 nm, 196 nm, 197 nm, 198 nm, 199, 200 nm, 201 nm, 202 nm, 203 nm, 204 nm, 205 nm, 206 nm, 207 nm, 208 nm, 209, 210 nm, 211 nm, 212 nm, 213 nm, 214 nm, 215 nm, 216 nm, 217 nm, 218 nm, 219, 220 nm, 221 nm, 222 nm, 223 nm, 224 nm, 225 nm, 226 nm, 227 nm, 228 nm, 229, 230 nm, 231 nm, 232 nm, 233 nm, 234 nm, 235 nm, 236 nm, 237 nm, 238 nm, 239, 240 nm, 241 nm, 242 nm, 243 nm, 244 nm, 245 nm, 246 nm, 247 nm, 248 nm, 249, 250 nm, 251 nm, 252 nm, 253 nm, 254 nm, 255 nm, 256 nm, 257 nm, 258 nm, 259, 260 nm, 261 nm, 262 nm, 263 nm, 264 nm, 265 nm, 266 nm, 267 nm, 268 nm, 269, 270 nm, 271 nm, 272 nm, 273 nm, 274 nm, 275 nm, 276 nm, 277 nm, 278 nm, 279, or 280 nm). In some embodiments, the UVC light has a power density of about 20 $mW/cm^2$ to about 1,000 $mW/cm^2$, e.g., about 30 $mW/cm^2$ to about 900 $mW/cm^2$, about 50 $mW/cm^2$ to about 850 $mW/cm^2$, about 100 $mW/cm^2$ to about 800 $mW/cm^2$, about 150 $mW/cm^2$ to about 750 $mW/cm^2$, about 200 $mW/cm^2$ to about 700 $mW/cm^2$, about 250 $mW/cm^2$ to about 650 $mW/cm^2$, about 300 $mW/cm^2$ to about 600 $mW/cm^2$, about 350 $mW/cm^2$ to about 550 $mW/cm^2$, about 400 $mW/cm^2$ to about 500 $mW/cm^2$, about 50 $mW/cm^2$, about 100 $mW/cm^2$, about 150 $mW/cm^2$, about 200 $mW/cm^2$, about 250 $mW/cm^2$, about 300 $mW/cm^2$, about 350 $mW/cm^2$, about 400 $mW/cm^2$, about 450 $mW/cm^2$, about 500 $mW/cm^2$, about 550 $mW/cm^2$, about 600 $mW/cm^2$, about 650 $mW/cm^2$, about 700 $mW/cm^2$, about 750 $mW/cm^2$, about 800 $mW/cm^2$, about 850 $mW/cm^2$, about 900 $mW/cm^2$, about 950 $mW/cm^2$, or about 1,000 $mW/cm^2$ and can be a continuous illumination or a pulsed illumination. In some embodiments, where the illumination is pulsed, the pulse frequency can be from the pulse frequency can be from about 1 Hz to about 1,000 Hz, e.g., about 5 Hz to about 950 Hz, about 10 Hz to about 900 Hz, about 25 Hz to about 850 Hz, about 50 Hz to about 800 Hz, about 100 Hz to about 750 Hz, about 150 Hz to about 700 Hz, about 200 Hz to about 650 Hz, about 250 Hz to about 600 Hz, about 300 Hz to about 550 Hz, about 350 Hz to about 525 Hz, about 400 to about 500, about 450 to about 475 Hz, about 2 Hz, about 5 Hz, about 10 Hz, about 25 Hz, about 50 Hz, about 100 Hz, about 150 Hz, about 200 Hz, about 250 Hz, about 300 Hz, about 350 Hz, about 400 Hz, about 450 Hz, about 500 Hz, about 550 Hz, about 600 Hz, about 650 Hz, about 700 Hz, about 750 Hz, about 800 Hz, about 850 Hz, about 900 Hz, about 950 Hz, about 1,000 Hz, with a duty cycle of 1-100% (e.g., 10%, 20%, 30%, 40%, 50%, 60%, 70%, 80%, 90%, 100%). In some embodiments, the sterilization of a tissue can include a plurality of sterilization sessions and can include any combination of the previously described procedures. In some embodiments, the sterilization device can be mounted onto a slit lamp apparatus. In further embodiments the illumination can be controlled with a footplate. In some embodiments, the light guide can be introduced into an affected area of a body to irradiate with a therapeutic dose of UVC radiation. In some embodiments the light guide can be introduced into an interior region of the eye (e.g., the vitreous body, the retina, the choroid, the macula, the lens, the ciliary muscles, or the optic nerve) to irradiate with a therapeutic and sterilizing dose of UVC. In some embodiments, the proximity determining element is connected to the light guide and communicates with a microprocessor that controls the irradiation. In some embodiments, the irradiation is only activated when the output end of the light guide reaches a predetermined distance from the sterilization site. In some embodiments, when the cycle of sterilization is complete the UVC sources deactivate, and a signal generator notifies the operator to remove the device. In further embodiments, whenever the device is prematurely removed from a sterilization site all emission of light is paused until the predetermined distance is restored. In some embodiments, the sterilization of a tissue can include the use of an aperture control element. The aperture control element for sterilization of a tissue permits a wide-field illumination of a target tissue utilizing an aperture control element (e.g., a cone) of an aperture diameter from 10 mm to 50 mm (e.g., 25 mm). In some embodiments, the sterilization can include an aperture control element that illuminates a tissue circumferentially (e.g., 360°).

Treatment of Corneal Ectasia Such as Keratoconus

In some embodiments, the device herein described can be used as a therapeutic device to treat corneal ectasia (e.g., keratoconus). In some embodiments, the device is configured to administer UVA light, and the configuration includes the base component of the device and a head component that can include UVA light source, a proximity determining element, and a signal generating element light guide. Treatment of keratoconus involves the crosslinking of riboflavin with ultraviolet A (UVA) light. The subject can be first administered a therapeutic dose of a photoactivator, such as riboflavin, to the eye. Suitable photoactivators include, but are not limited to, riboflavin, Rose Bengal, porphyrin-based photosensitizers, psoralens, quinones, anthracyclins, anthracenediones, xanthenes, fluoresceins, rhodamines, phthaleins, cyanines, chalcogenapyrylium dyes, triarylmethane dyes, phenothiazines, phenoxazines, acridines, hypericin, nicotinamide adenine dinucleotide phosphate (NADPH), 5-aminolevulinic acid, ciprofloxacin, and quinine. In some embodiments, a sterilizing session using the device can include irradiation of an affected tissue area with UVA light of a wavelength from about 315 nm to about 400 nm (e.g., about 316 nm, 317 nm, 318 nm, 319 nm, 320 nm, 321 nm, 322 nm, 323 nm, 324 nm, 325 nm, 326 nm, 327 nm, 328 nm, 329 nm, 330 nm, 331 nm, 332 nm, 333 nm, 334 nm, 335 nm, 336 nm, 337 nm, 338 nm, 339 nm, 340 nm, 341 nm, 342 nm, 343 nm, 344 nm, 345 nm, 346 nm, 347 nm, 348 nm, 349 nm, 350 nm, 351 nm, 352 nm, 353 nm, 354 nm, 355 nm, 356 nm, 357 nm, 358 nm, 359 nm, 360 nm, 361 nm, 362 nm, 363 nm, 364 nm, 365 nm, 366 nm, 367 nm, 368 nm, 369 nm, 370 nm, 371 nm, 372 nm, 373 nm, 374 nm, 375 nm, 376 nm, 377 nm, 378 nm, 379 nm, 380 nm, 381 nm, 382 nm, 383 nm, 384 nm, 385 nm, 386 nm, 387 nm, 388 nm, 389 nm, 390 nm, 391 nm, 392 nm, 393 nm, 394 nm, 395 nm, 396 nm, 397 nm, 398 nm, 399 nm, or 400 nm). In some embodiments, the UVA light has a power density of about 0.5 $mW/cm^2$ to about 30 $mW/cm^2$ (e.g., about 1.0 $mW/cm^2$, about 2.0 $mW/cm^2$, about 3.0 $mW/cm^2$, about 4.0 $mW/cm^2$, about 5.0 $mW/cm^2$, about 6.0 $mW/cm^2$, about 7.0 $mW/cm^2$, about 8.0 $mW/cm^2$, about 9.0 $mW/cm^2$, about 10 $mW/cm^2$, about 11 $mW/cm^2$, about 12 $mW/cm^2$, about 13 $mW/cm^2$, about 14 $mW/cm^2$, about 15 $mW/cm^2$, about 16 $mW/cm^2$, about 17 $mW/cm^2$, about 18 $mW/cm^2$, about 19 $mW/cm^2$, about 20 $mW/cm^2$, about 21 $mW/cm^2$, about 22 $mW/cm^2$, about 23 $mW/cm^2$, about 24 $mW/cm^2$, about 25 $mW/cm^2$, about 26 $mW/cm^2$, about 27 $mW/cm^2$, about 28 $mW/cm^2$, about 29 $mW/cm^2$, or about 30 $mW/cm^2$) and can be as continuous or pulsed illumination. In some embodiments, where the illumination is pulsed, the pulse frequency can be from about 20 Hz to about 1,000 Hz, e.g., about 50 Hz to about 950 Hz, about 100 Hz to about 900 Hz, about 150 Hz to about 850 Hz, about 200 Hz to about 800 Hz, about 250 Hz to about 750 Hz, about 300 Hz to about 700 Hz, about 350 Hz to about 650 Hz, about 400 Hz to about 600 Hz, about 450 Hz to about 550 Hz, about 500 Hz to about 525 Hz, about 50 Hz, about 100 Hz, about 150 Hz, about 200 Hz, about 250 Hz, about 300 Hz, about 350 Hz, about 400 Hz, about 450 Hz, about 500 Hz, about 550 Hz, about 600 Hz, about 650 Hz, about 700 Hz, about 750 Hz, about 800 Hz, about 850 Hz, about 900 Hz, about 950 Hz, about 1,000 Hz, with a duty cycle of 1-100% (e.g., 10%, 20%, 30%, 40%, 50%, 60%, 70%, 80%, 90%, 100%). In some embodiments, the treatment of an ectasia, such as keratoconus, can include a plurality of sessions and can include any combination of the previously described procedures. In some embodiments, the device can be mounted onto a slit lamp apparatus. In further embodiments the illumination can be controlled with a footplate. In some embodiments, the light guide can be used to irradiate with a therapeutic dose of UVC radiation. In some embodiments, the proximity determining element is connected to the light guide and communicates with a microprocessor that controls the irradiation. In some embodiments, the irradiation is only activated when the output end of the light guide reaches a predetermined distance from the site of administration. In some embodiments, when the cycle of administration is complete the UVA source deactivates, and a signal generator notifies the operator to remove the device. In further embodiments, whenever the device is prematurely removed from a site of administration, emission of light is paused until the predetermined distance is restored.

Sterilization of Contact Lenses, Contact Lens Cases, Eyeglasses, or Eyeglasses Cases In some embodiments, the device herein described can be used as a sterilization device to sterilize a contact lens, a contact lens case, eyeglasses and/or an eyeglasses case. In some embodiments, the sterilization device is configured to sterilize a contact lens, a contact lens case, eyeglasses and/or an eyeglasses case and the configuration includes the base component of the device and a head component that can include a UV source. In some embodiments the device herein described can be configured to sterilize contact lens accessory items (e.g., a contact lens sucker, plunger, or a finger glove) In some embodiments, a sterilizing session using the device can include irradiation of the a contact lens, a contact lens case, eyeglasses and/or an eyeglasses case with UVC light of a wavelength between 100 nm and 280 nm (e.g., 105 nm to 275 nm, 110 nm to 270 nm, 115 nm to 265 nm, 120 nm to 260 nm, 125 nm to 255 nm, 130 nm to 250 nm, 135 nm to 245 nm, 140 nm to 240 nm, 145 nm to 235 nm, 150 nm to 230 nm, 155 nm to 225 nm, 160 nm to 220 nm, 165 nm to 215 nm, 170 nm to 210 nm, 175 nm to 205 nm, 180 nm to 200 nm, 185 nm to 195 nm, 101 nm, 102 nm, 103 nm, 104 nm, 105 nm, 106 nm, 107 nm, 108 nm, 109, 110 nm, 111 nm, 112 nm, 113 nm, 114 nm, 115 nm, 116 nm, 117 nm, 118 nm, 119, 120 nm, 121 nm, 122 nm, 123 nm, 124 nm, 125 nm, 126 nm, 127 nm, 128 nm, 129, 130 nm, 131 nm, 132 nm, 133 nm, 134 nm, 135 nm, 136 nm, 137 nm, 138 nm, 139, 140 nm, 141 nm, 142 nm, 143 nm, 144 nm, 145 nm, 146 nm, 147 nm, 148 nm, 149, 150 nm, 151 nm, 152 nm, 153 nm, 154 nm, 155 nm, 156 nm, 157 nm, 158 nm, 159, 160 nm, 161 nm, 162 nm, 163 nm, 164 nm, 165 nm, 166 nm, 167 nm, 168 nm, 169, 170 nm, 171 nm, 172 nm, 173 nm, 174 nm, 175 nm, 176 nm, 177 nm, 178 nm, 179, 180 nm, 181 nm, 182 nm, 183 nm, 184 nm, 185 nm, 186 nm, 187 nm, 188 nm, 189, 190 nm, 191 nm, 192 nm, 193 nm, 194 nm, 195 nm, 196 nm, 197 nm, 198 nm, 199, 200 nm, 201 nm, 202 nm, 203 nm, 204 nm, 205 nm, 206 nm, 207 nm, 208 nm, 209, 210 nm, 211 nm, 212 nm, 213 nm, 214 nm, 215 nm, 216 nm, 217 nm, 218 nm, 219, 220 nm, 221 nm, 222 nm, 223 nm, 224 nm, 225 nm, 226 nm, 227 nm, 228 nm, 229, 230 nm, 231 nm, 232 nm, 233 nm, 234 nm, 235 nm, 236 nm, 237 nm, 238 nm, 239, 240 nm, 241 nm, 242 nm, 243 nm, 244 nm, 245 nm, 246 nm, 247 nm, 248 nm, 249, 250 nm, 251 nm, 252 nm, 253 nm, 254 nm, 255 nm, 256 nm, 257 nm, 258 nm, 259, 260 nm, 261 nm, 262 nm, 263 nm, 264 nm, 265 nm, 266 nm, 267 nm, 268 nm, 269, 270 nm, 271 nm, 272 nm, 273 nm, 274 nm, 275 nm, 276 nm, 277 nm, 278 nm, 279, or 280 nm). In some embodiments, the UVC light has a power density from about 20 $mJ/cm^2$ to about 5000 $mJ/cm^2$, e.g., from about 50 $mJ/cm^2$ to about 4500 $mJ/cm^2$, from about 100 $mJ/cm^2$ to about 4000 $mJ/cm^2$, from about 200 $mJ/cm^2$ to about 4000 $mJ/cm^2$, from about 300 $mJ/cm^2$ to about 3500 $mJ/cm^2$, from about 500 $mJ/cm^2$ to about 3000 $mJ/cm^2$, from about 1,000 $mJ/cm^2$ to about 2500 $mJ/cm^2$, from about 1500 $mJ/cm^2$ to about 2000 $mJ/cm^2$, about 100 $mJ/cm^2$, about 200 $mJ/cm^2$, about 300 $mJ/cm^2$, about 400 $mJ/cm^2$, about 500 $mJ/cm^2$, about 600 $mJ/cm^2$, about 700 $mJ/cm^2$, about 800 $mJ/cm^2$, about 900 $mJ/cm^2$, about 1,000 $mJ/cm^2$, about 1500 $mJ/cm^2$, about 2000 $mJ/cm^2$, about 2500 $mJ/cm^2$, about 3000 $mJ/cm^2$, about 3500 $mJ/cm^2$, about 4000 $mJ/cm^2$, about 4500 $mJ/cm^2$, about 5000 $mJ/cm^2$ and can be a continuous illumination or a pulsed illumination. In some embodiments, where the illumination is pulsed, the pulse frequency can be from the pulse frequency can be from about 20 Hz to about 1,000 Hz, e.g., about 50 Hz to about 950 Hz, about 100 Hz to about 900 Hz, about 150 Hz to about 850 Hz, about 200

Hz to about 800 Hz, about 250 Hz to about 750 Hz, about 300 Hz to about 700 Hz, about 350 Hz to about 650 Hz, about 400 Hz to about 600 Hz, about 450 Hz to about 550 Hz, about 500 Hz to about 525 Hz, about 50 Hz, about 100 Hz, about 150 Hz, about 200 Hz, about 250 Hz, about 300 Hz, about 350 Hz, about 400 Hz, about 450 Hz, about 500 Hz, about 550 Hz, about 600 Hz, about 650 Hz, about 700 Hz, about 750 Hz, about 800 Hz, about 850 Hz, about 900 Hz, about 950 Hz, about 1,000 Hz, Hz, with a duty cycle of 1-100% (e.g., 10%, 20%, 30%, 40%, 50%, 60%, 70%, 80%, 90%, 100%). In some embodiments, the sterilization can include a plurality of sterilization sessions (e.g., daily, weekly, monthly, annually) and can include any combination of the previously described procedures. In some embodiments, the sterilization device can be connected to a contact lens case. In some embodiments, the sterilization device can be connected to an eyeglass case. In further embodiments the sterilization occurs in combination with ultrasound emitted by the contact lens case or the eyeglasses case.

EXAMPLES

The following examples are put forth so as to provide those of ordinary skill in the art with a description of how the compositions and methods described herein can be used, made, and evaluated, and are intended to be purely exemplary of the invention and are not intended to limit the scope of what the inventors regard as their invention.

Example 1. Use of Therapeutic Device to Treat Blepharitis and/or MGD

The therapeutic device described herein can be used to treat blepharitis and/or MGD. An ophthalmologist uses a device for treating blepharitis and/or MGD (FIGS. 1-8). The head component is equipped with a UV source, and optionally one or more of an IR light source, a heat source, a source of intense pulsed light, and a source of ultrasound (FIGS. 1-8). The ophthalmologist presses the control button on the base component and draws the head component near the lower eyelid of a patient's left eye. The ophthalmologist places the head component in contact with the affected eyelid and proceeds to deliver therapy by pressing a control button on the base component of the device. Therapeutic UVC light of 265 nm in wavelength is emitted from the distal end of the head component at a power of 2 mW/cm$^2$ and fora duration of 30 seconds. Following the irradiation of the eyelid with UVC, the ophthalmologist presses the control button a second time to select for ultrasound and heat to be emitted by the distal end of the head component. Therapeutic ultrasound of frequency of 3 MHz at 0.7 W/cm$^2$ is delivered to the eyelid along with simultaneous heating by a heating element at the distal end of the head component to raise the temperature of a meibomian gland to about 40° C. causing softening and removal of oily particulates clogging meibomian glands of the affected eyelid. Next, the ophthalmologist presses the control button on the base component a third time to activate the irradiation of the eyelid with infrared light of 2.0 μm in wavelength for a duration of 12 minutes with down periods of 30 seconds interleaved between therapy irradiation. The therapy is repeated monthly for a total of four treatment sessions.

Example 2. Use of Therapeutic Device to Treat Ocular Cancer

The therapeutic device described herein can be used to treat ocular cancer. An oncologist uses a device for treating ocular melanoma (FIGS. 9-15). The head component is equipped with a UV source, a proximity determining element, and an imaging module (FIGS. 9-15). The oncologist presses the power button on the base component activating the proximity determining element and draws the device near to the affected eye. The proximity determining element signals to the oncologist when a predetermined distance between the UVC light source at the distal end of the head component and the melanoma site is reached. The proximity determining element activates a green light visible to the oncologist when the device is at the predetermined distance and activates a red light visible to the oncologist when the device is outside of the predetermined distance. Holding the therapeutic device at the predetermined distance from the neoplasia site, the oncologist activates the UVC light positioned at the distal end of the head component and delivers a therapeutic session of UVC light of 265 nm in wavelength, at a pulse frequency of 5 Hz for a duration of 10 minutes. The UVC therapy is administered between 1-10 times with interleaved rest periods of one week.

Example 3. Use of Therapeutic Device to Reduce the Viral Load in an Oral Cavity The therapeutic device described herein can be used to reduce the viral load inside the mouth of a patient with SARS-CoV-2. A dentist uses a device for sterilizing an oral cavity. The head component is equipped with a UV source, a UVC light optical fiber, a proximity determining element, and a signal generating element. The dentist attaches the input end of the optical fiber to the distal end of the UVC light source of the head component to deliver the UVC light inside the mouth. Then the dentist presses the power button on the base component of the device. The optical fiber is equipped with a proximity determining element that maintains the UVC light off until a predetermined sterilizing distance between the output end of the optical fiber and the treatment site is reached. Once the output end of the optical fiber reaches the predetermined distance from the treatment site, the proximity determining element activates a green light to signal to the dentist that the predetermined distance has been achieved. Holding the optical fiber at the predetermined distance from the treatment site, the dentist activates the UVC light positioned at the distal end of the head component and delivers a therapeutic session of UVC light of 265 nm in wavelength, and power of 20 mW/cm$^2$ at a pulse frequency of 20 Hz for a duration 30 seconds. The UVC therapy is repeated, if necessary, for future dental treatment.

Example 4. Use of Therapeutic Device to Treat Keratoconus

Figure 16:
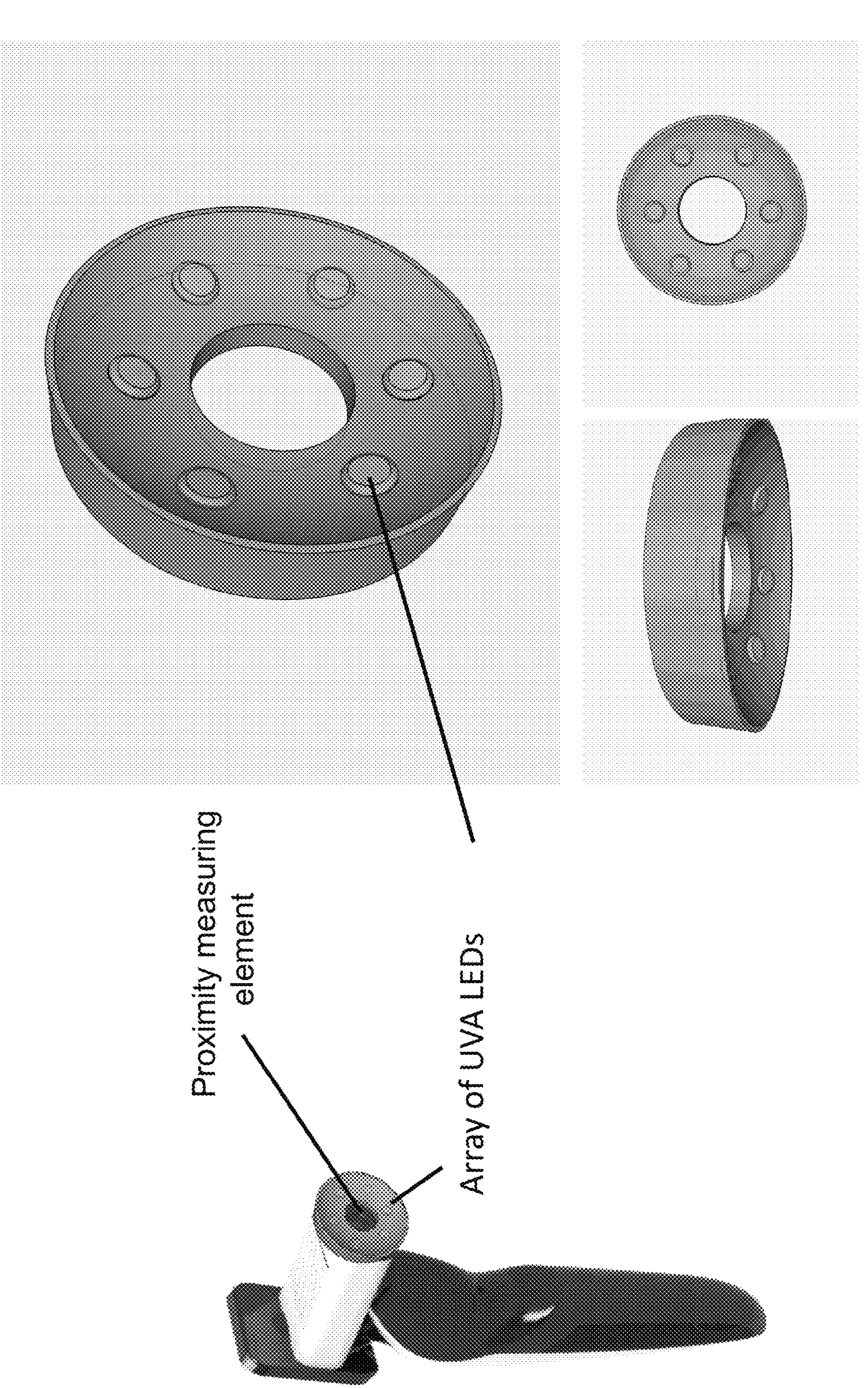
FIG. 16 is a group of schematic drawings of the therapeutic side of the therapeutic device. The proximity measuring element, and the array of UVA LEDs are shown.
Figure 17:
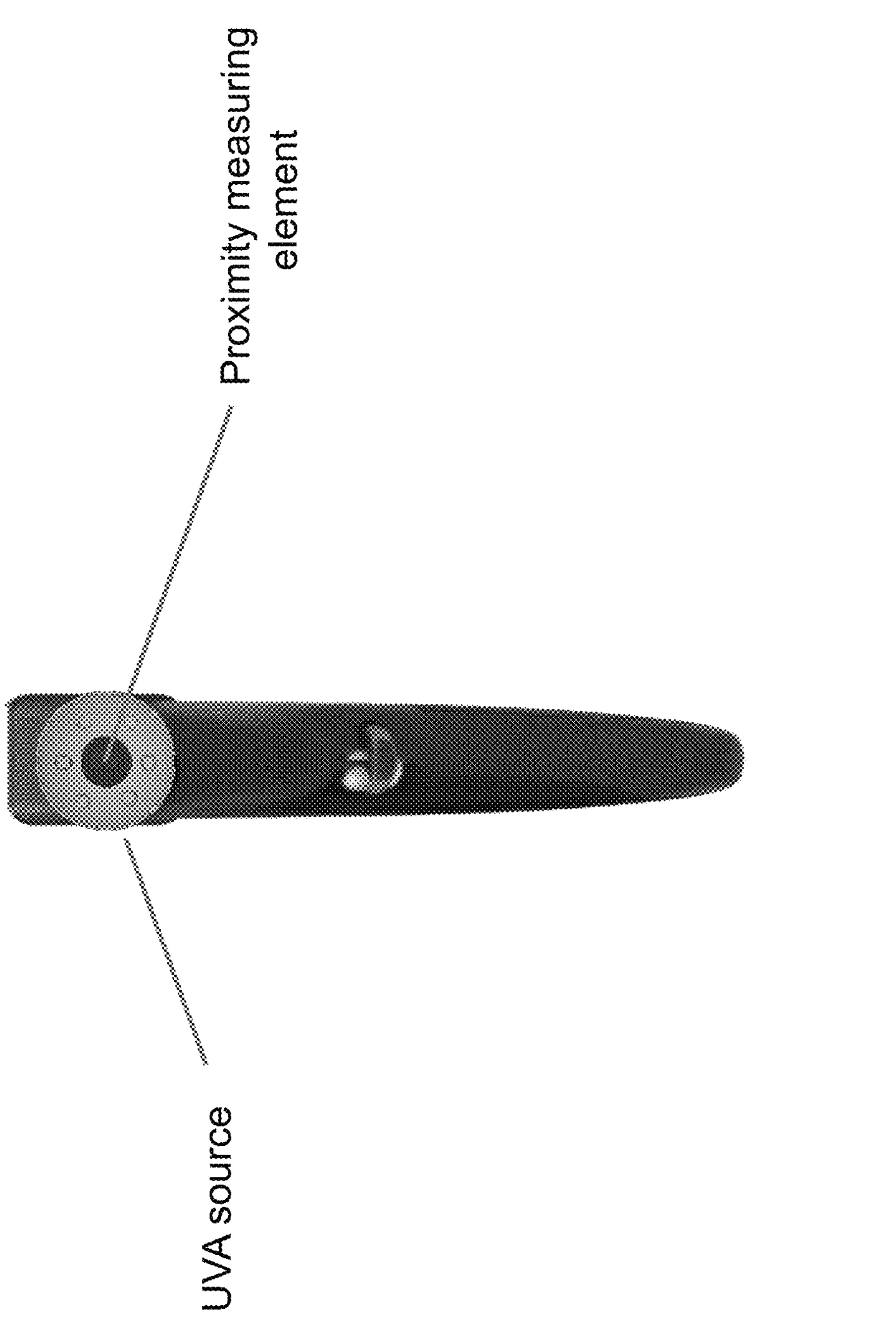
FIG. 17 is a schematic drawing of the therapeutic side of the therapeutic device. The proximity measuring element, and the array of UVA LEDs are shown.
Figure 18:
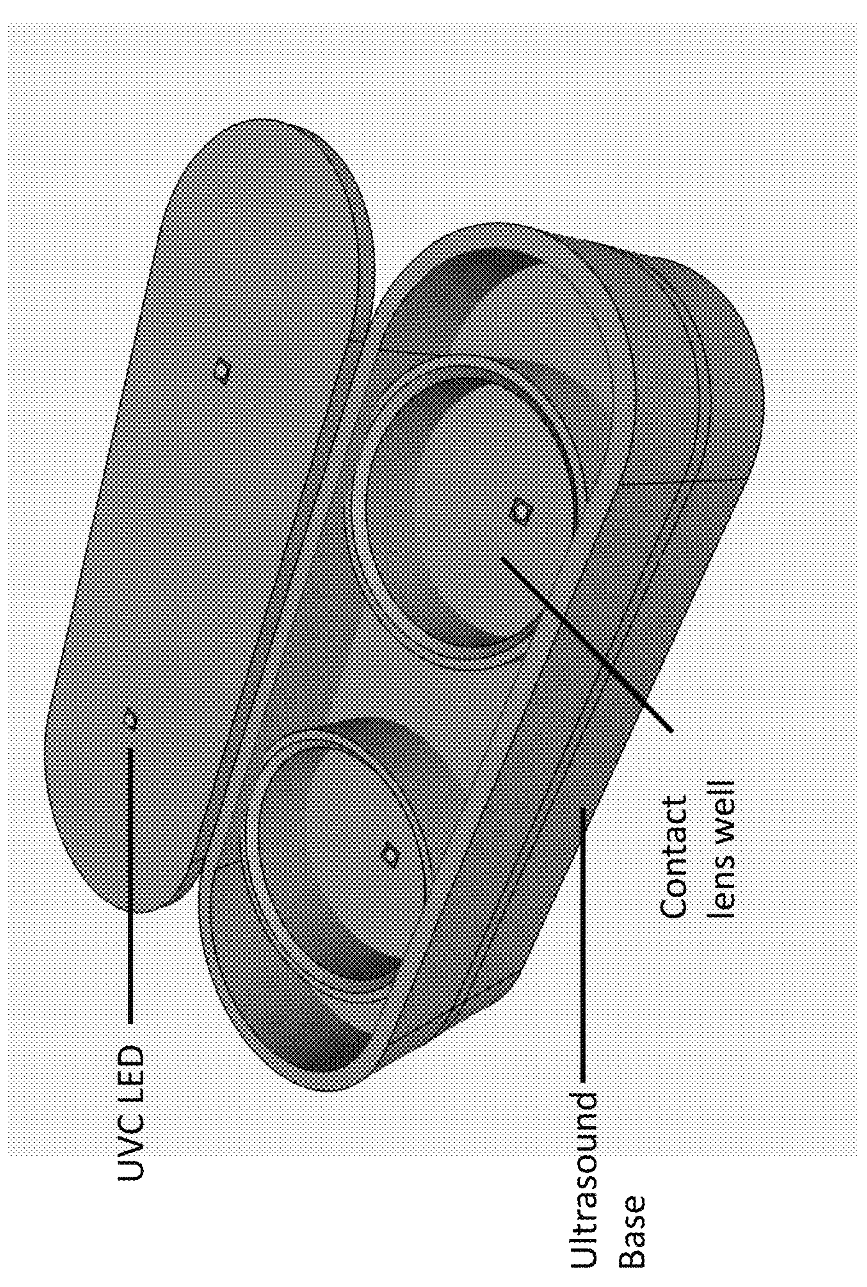
FIG. 18 is a schematic drawing of the UVC sterilization device. Multiple UVC LED sources, the base component configured to deliver ultrasound and the contact lens wells are shown.
Figure 19:
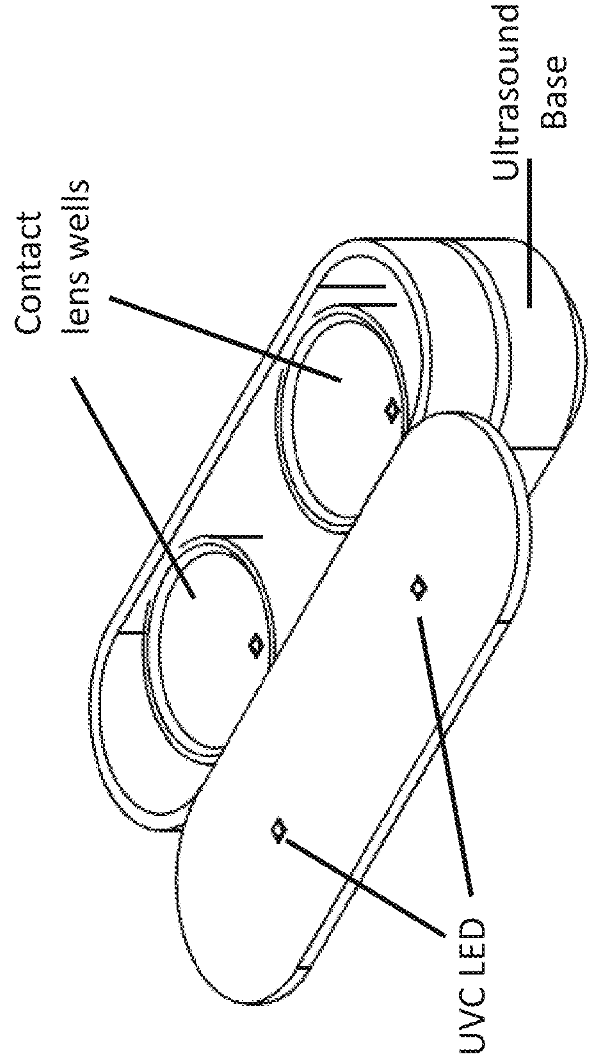
FIG. 19 is a schematic drawing of the UVC sterilization device. Multiple UVC LED sources, the base component configured to deliver ultrasound and the contact lens wells are shown.
Figure 20:
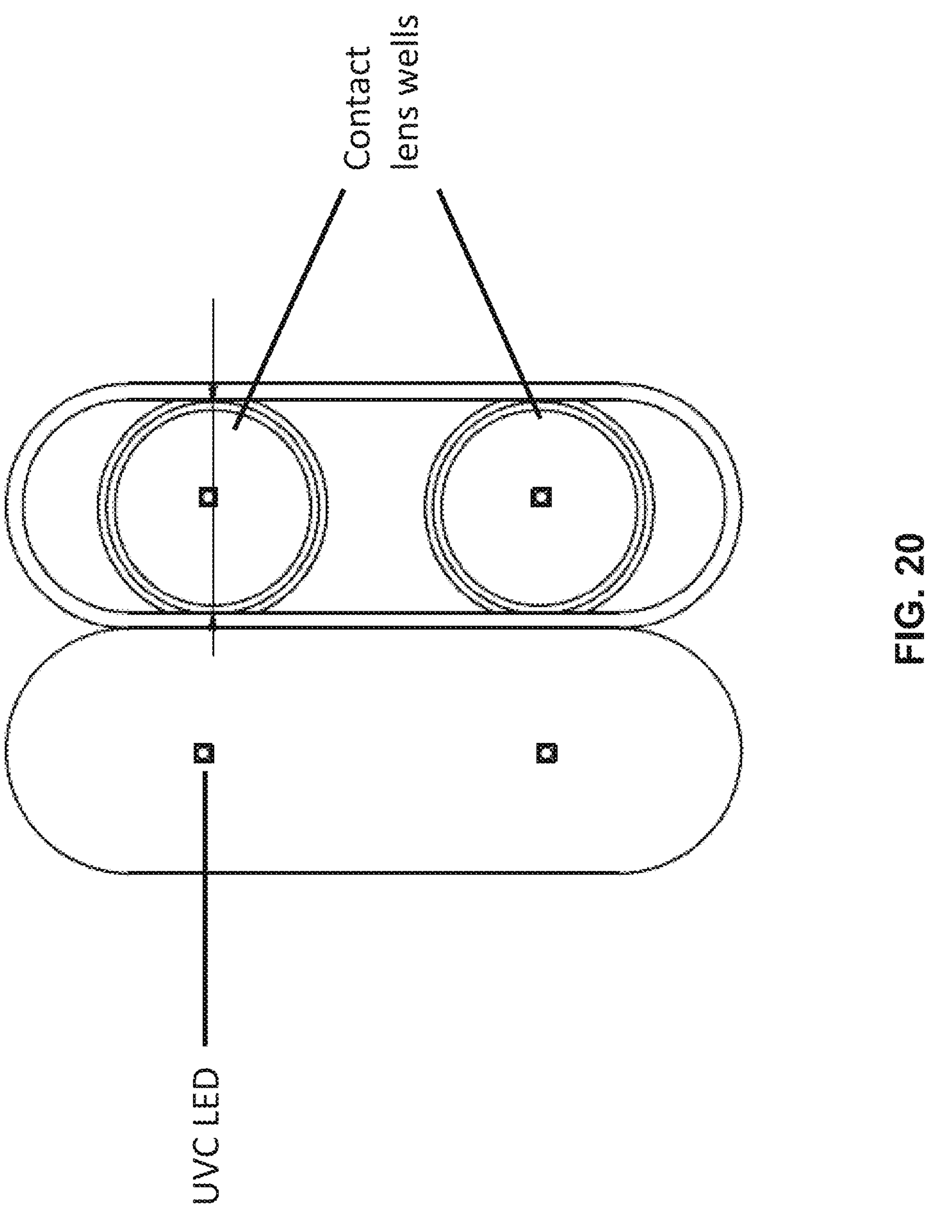
FIG. 20 is a schematic drawing of the top view of the UVC sterilization device. Multiple UVC LED sources, the base component configured to deliver ultrasound and the contact lens wells are shown.
Figure 21:
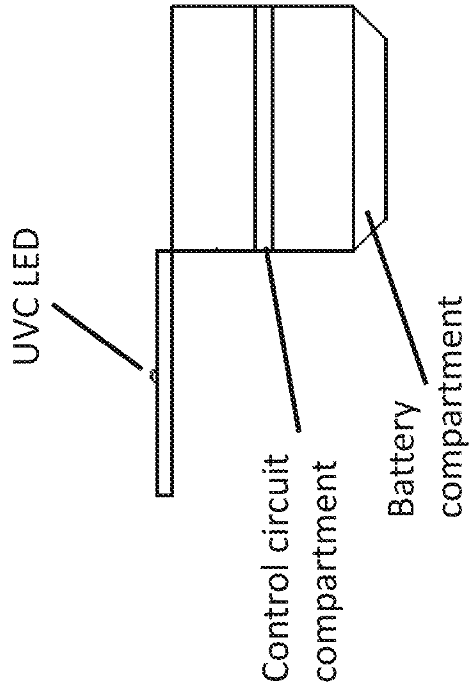
FIG. 21 is a schematic drawing of the side view of the UVC sterilization device. The control circuit compartment configured to deliver ultrasound and UVC and the battery compartment are shown.
Figure 22:
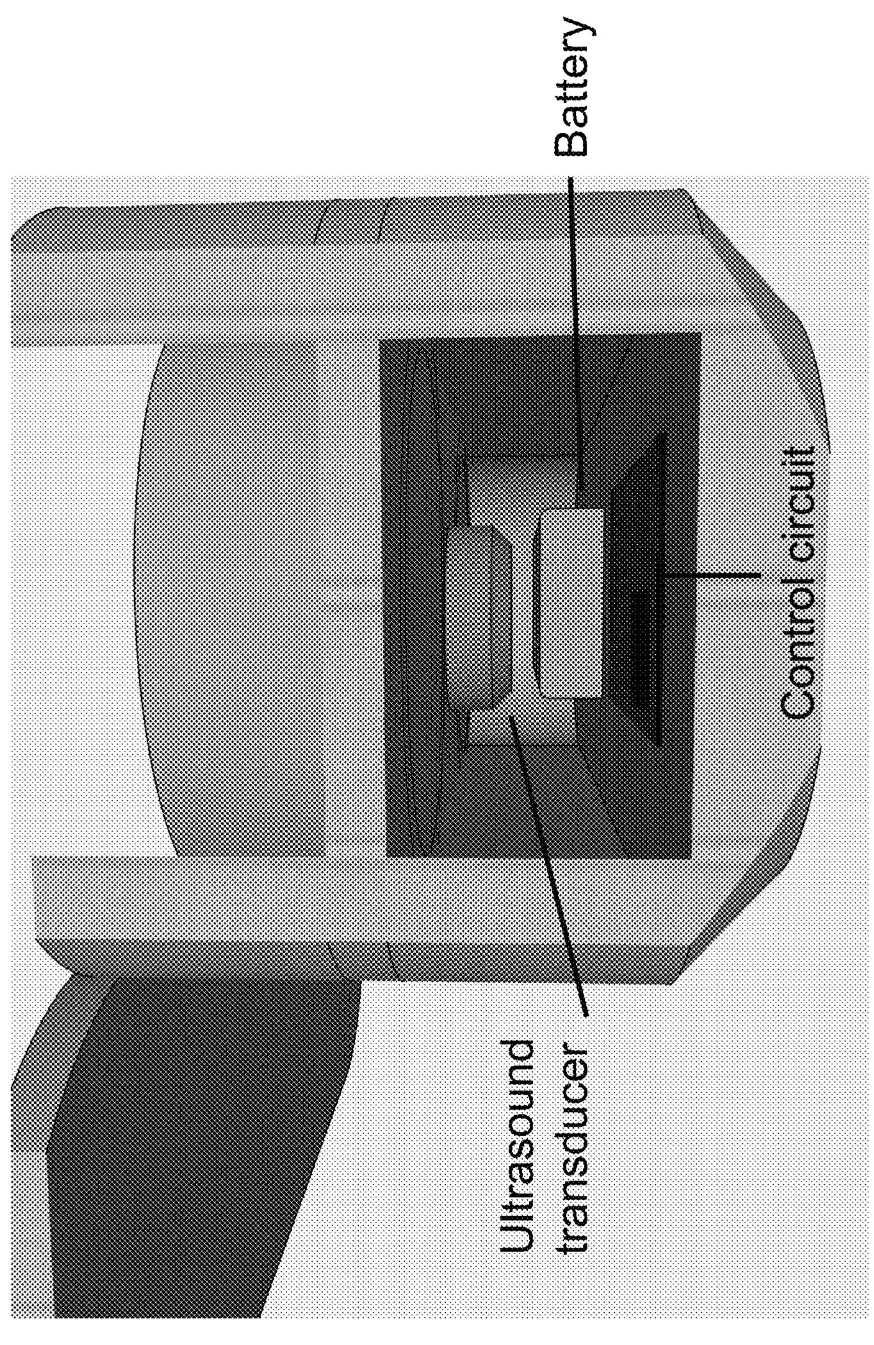
FIG. 22 is a schematic drawing of the internal components of the base of the UVC sterilization device. The control circuit compartment configured to deliver ultrasound and UVC, the battery compartment, and the ultrasound transducer are shown.
Figure 23:
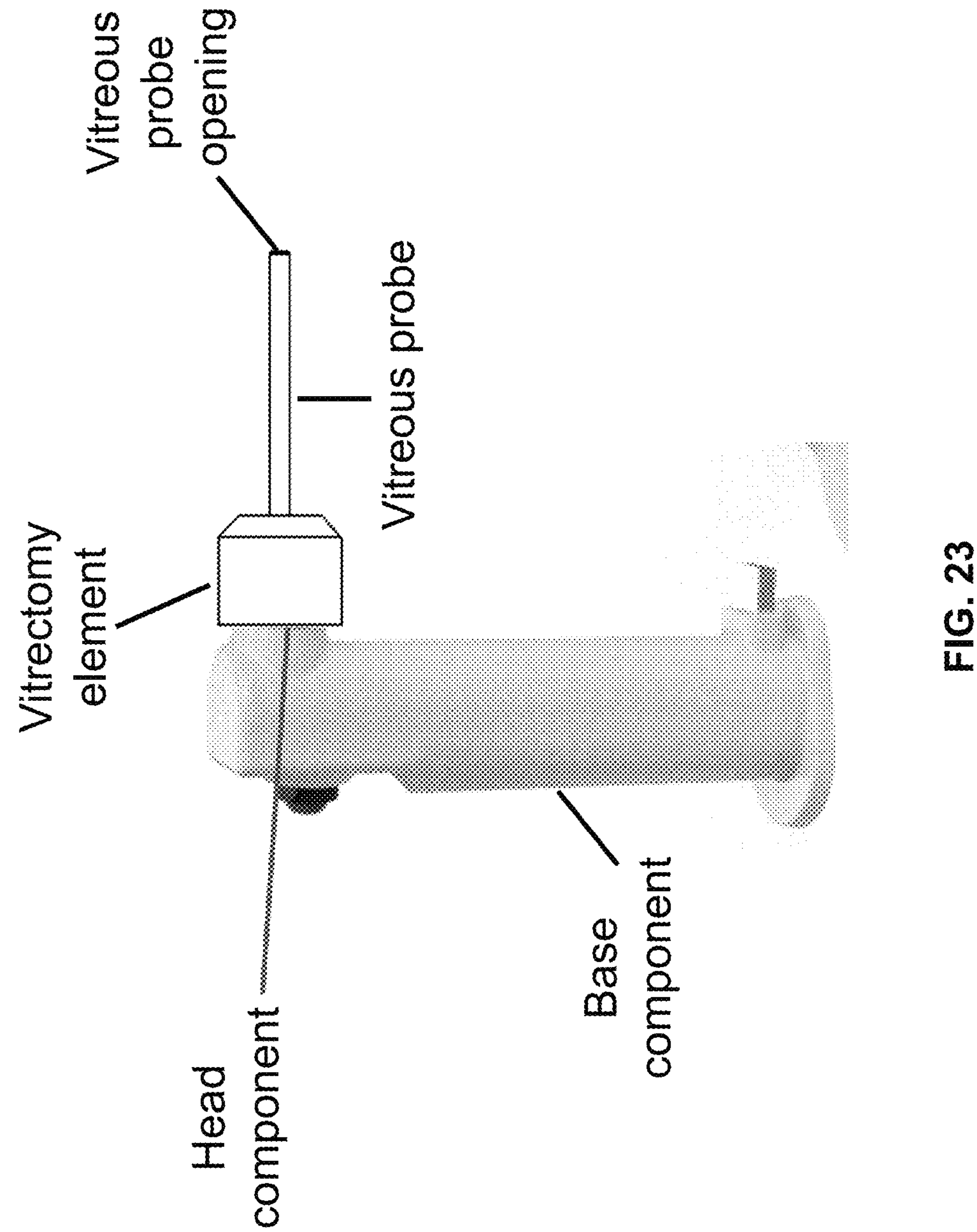
FIG. 23 is a schematic drawing of an embodiment of the vitrectomy element shown connected to the distal end of the head component of the UVC sterilization device. The vitreous probe and the vitreous probe opening are shown. In this embodiment, UVC radiation enters at one end of the vitrectomy element and exits at the vitreous probe opening configured to be inserted into an interior region of an eye.
Figures 24A, 24B:
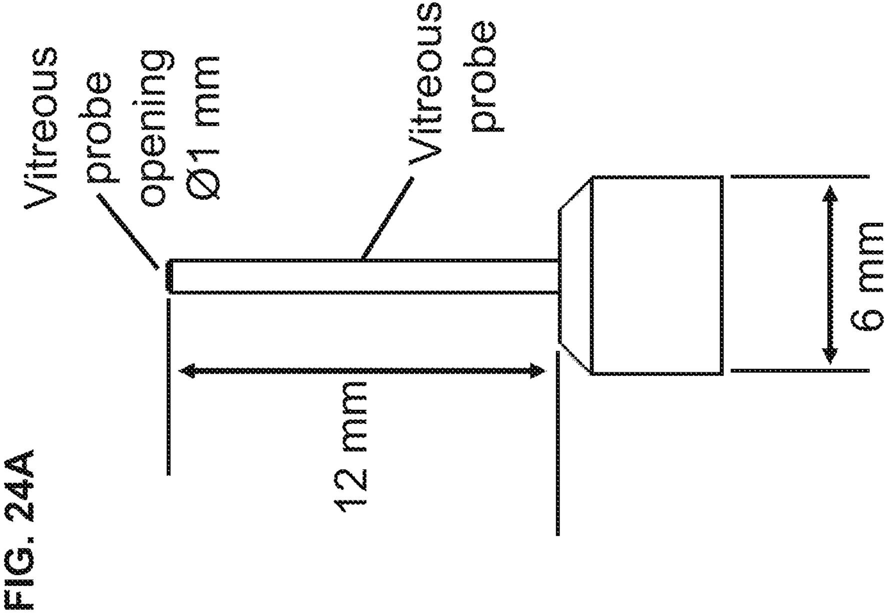
FIG. 24A is a schematic drawing of a side view of an embodiment of the vitrectomy element shown having a base with a diameter of 6 mm, a vitreous probe having a length of 12 mm, and the vitreous probe opening is shown to have a diameter of 1 mm.
FIG. 24B is a schematic drawing of a perspective view of an embodiment of the vitrectomy element shown having a vitreous probe opening with a diameter of 1 mm.

The therapeutic device described herein can be used to treat keratoconus. Treatment of keratoconus involves the crosslinking of riboflavin with ultraviolet A (UVA) light. An ophthalmologist first administers to the patient's affected eye a therapeutic solution of riboflavin. The ophthalmologist uses a device for treating keratoconus (FIGS. 16 and 17). The head component is equipped with a UVA light source, a proximity determining element, and a signal generating element (FIGS. 16 and 17). The ophthalmologist presses the power button on the base component activating the proximity determining element and draws near the device to the affected cornea. The proximity determining element signals to the ophthalmologist when a predetermined distance between the UVA light source at the distal end of the head component and the affected cornea is reached. The proximity determining element activates a green light visible to the ophthalmologist when the device is at the predetermined distance and activates a red light visible to the ophthalmologist when the device is outside of the predetermined distance. Holding the therapeutic device at the predetermined distance from the affected cornea, the ophthalmologist activates the UVA light positioned at the distal end of the head component and delivers a dose of UVA light of 365 nm in wavelength, and power of 9 mW/cm$^2$ for a duration of 10 minutes.

Example 5. Use of Therapeutic Device to Sterilize Contact Lenses

The therapeutic device described herein can be used to sterilize contact lenses. A person uses a device for sterilizing a contact lenses and attaches the head component to the base component of the sterilizing device (FIGS. 18-22). The head component is equipped with a UV source, and an attachment clip that connects the distal end of the head component to a storage case for contact lens. The contact lens case is also equipped with an ultrasound source. The person attaches the sterilizing device, including the base component and the contact lens sterilizing head component, to the contact lens case. Then the person presses the power button on the base component of the sterilizing device activating a predetermined sterilization program that combines UVC irradiation of 220 nm in wavelength, and power of 20 mW/cm$^2$ and a pulse frequency of 5 Hz with ultrasound of 3 MHz for a duration of 300 seconds. The UVC therapy is repeated daily.

Example 6. Use of Therapeutic Device to Sterilize Eyeglasses

The therapeutic device described herein can be used to sterilize eyeglasses. A person uses a head component for sterilizing eyeglasses and attaches the head component to the base component of the sterilizing device. The head component is equipped with a UV source, and an attachment clip that connects the distal end of the head component to a storage case for eyeglasses. The eyeglasses case is also equipped with an ultrasound source. The person attaches the sterilizing device, including the base component and the eyeglasses sterilizing head component, to the eyeglasses case. Then the person presses the power button on the base component of the sterilizing device activating a predetermined sterilization program that combines UVC irradiation of 265 nm in wavelength, and power of 20 mW/cm$^2$ with ultrasound of 3 MHz for a duration of 300 seconds. The UVC and ultrasound therapy is repeated after use of the eyeglasses.

Example 7. Use of Therapeutic Device to Sterilize an Eye and an Eyelid

The therapeutic device described herein can be used to reduce the viral load on an eye and an eyelid of a patient with SARS-CoV-2 prior to a surgical procedure. An ophthalmologist uses a device for sterilizing an eye and an eyelid. The head component is equipped with a UV source, an aperture control component, a proximity determining element, and a signal generating element. The ophthalmologist attaches the UVC LED delivery head to the head component and proceeds to attach a 50 mm diameter aperture control component to the distal end of the UVC LED to deliver the UVC light to an eyelid. Then the ophthalmologist presses the power button on the base component of the device. The head component is equipped with a proximity determining element that maintains the UVC light off until a predetermined sterilizing distance between the output end of the aperture control component and the treatment site is reached. Once the output of end of the aperture control component reaches the predetermined distance from the treatment site, the proximity determining element activates a green light to signal to the ophthalmologist that the predetermined distance has been achieved. Holding the aperture control component at the predetermined distance from the treatment site, the ophthalmologist activates the UVC light positioned at the distal end of the head component and delivers a therapeutic session of UVC light of 265 nm in wavelength, at a pulse frequency of 20 Hz for a duration 30 seconds. The UVC therapy is only repeated prior to the start of a subsequent surgical procedure.

Example 8. Use of Therapeutic Device to Sterilize a Nasal Cavity

The therapeutic device described herein can be used to reduce the viral load inside the nose of a patient with SARS-CoV-2. An otolaryngologist selects a device for sterilizing a nasal cavity. The head component is equipped with a UV source, a UVC light optical fiber, an aperture control component, a proximity determining element, and a signal generating element. The otolaryngologist attaches the input end of the optical fiber to the distal end of the UVC light source of the head component and the aperture control component with 360° irradiation to deliver the UVC light inside the nose. Then the otolaryngologist presses the power button on the base component of the device. The optical fiber is equipped with a proximity determining element that maintains the UVC light off until a predetermined sterilizing distance between the output end of the optical fiber and the treatment site is reached. Once the output of end of the optical fiber reaches the predetermined distance from the treatment site, the proximity determining element activates a green light to signal to the otolaryngologist that the predetermined distance is achieved. Holding the optical fiber at the predetermined distance from the treatment site, the otolaryngologist activates the UVC light positioned at the distal end of the head component and delivers a therapeutic session of continuous UVC light of 265 nm in wavelength.

Example 9. Use of Therapeutic Multi-Head Device

The therapeutic device described herein can be used to treat different medical indications. Its design including a base component and multiple therapeutic heads configured to treat different indications allows a healthcare provider to exchange the therapeutic heads between different patients. An ophthalmologist selects a head component for treating blepharitis in a first patient. The head component is equipped with a UV source, an IR light source, a heat source, and a source of ultrasound. The ophthalmologist presses the power button on the base component and draws the head component near the lower eyelid of a patient's left eye. The ophthalmologist places the head component in contact with the affected eyelid and proceeds to deliver therapy by pressing a control button on the base component of the device. Therapeutic UVC light of 265 nm in wavelength is emitted from the distal end of the head component at a power of 10 mW/cm$^2$ and for a duration of 30 seconds. Following the irradiation of the eyelid with UVC, the ophthalmologist presses the control button a second time to select for ultrasound and heat to be emitted by the distal end of the head component. Therapeutic ultrasound of frequency of 3 MHz at 0.7 W/cm$^2$ is delivered to the eyelid along with simultaneous heating by a heating element to raise the temperature of the eyelid to 40° C. causing softening and ease of removal of oily particulates clogging meibomian glands of the affected eyelid. The therapy is repeated monthly and is supplemented by manual or automated expression of the glands. The ophthalmologist then sees a second patient and selects a head for sterilizing an eyelid to reduce the viral load on the eyelid. The ophthalmologist removes the head for blepharitis therapy from the base component by pressing on a release button on the base component and replaces it with the head and optical fiber for sterilization applications. The ophthalmologist secures the base component with an attachment adapter element to a slit lamp to allow his hands to control the optical fiber. Then the ophthalmologist presses the power button on the base component of the device. The optical fiber is equipped with a proximity determining element that maintains the UVC light off until a predetermined sterilizing distance between the output end of the optical fiber and the treatment site is reached. Once the output of end of the optical fiber reaches the predetermined distance from the treatment site, the proximity determining element activates a green light to signal to the dentist that the predetermined distance is achieved. Holding the optical fiber at the predetermined distance from the treatment site, the ophthalmologist activates the UVC light positioned at the distal end of the head component and delivers a therapeutic session of continuous UVC light of 265 nm in wavelength, and power of 20 mW/cm$^2$ for a duration of 30 seconds.

Example 10. Use of Therapeutic Device to Treat Gastric Ulcers

The therapeutic device described herein can be used to reduce the bacterial load inside the gastrointestinal tract of a patient with an *H. pylori* ulcer. A gastroenterologist selects a head component for sterilizing a gastrointestinal cavity and attaches the head component to the base component of the therapeutic device. The head component is equipped with an ultraviolet C (UVC) light source, a UVC light optical fiber, a proximity determining element, and a signal generating element. The gastroenterologist attaches the input end of the optical fiber to the distal end of the UVC light source of the head component to deliver the UVC light inside the gastrointestinal cavity (this may be attached to an endoscope or integral to the endoscope). Then the gastroenterologist presses the power button on the base component of the device. The optical fiber is equipped with a proximity determining element that maintains the UVC light off until a predetermined sterilizing distance between the output end of the optical fiber and the treatment site is reached. Once the output of end of the optical fiber reaches the predetermined distance from the treatment site, the proximity determining element activates a green light to signal to the gastroenterologist that the predetermined distance is achieved. Holding the optical fiber at the predetermined distance from the treatment site, the gastroenterologist activates the UVC light positioned at the distal end of the head component and delivers a therapeutic session of UVC light of 265 nm in wavelength, at a pulse frequency of 5 Hz for a duration of 30 seconds. The UVC therapy is repeated up to 10 times with interleaved rest periods of 300 seconds.

Example 11. Use of Therapeutic Device to Treat Gingivitis

The therapeutic device described herein can be used to treat gingivitis inside the mouth of a patient. A dental hygienist uses a device for sterilizing an oral cavity. The head component is attached to a light guide equipped with a UVC LED at a distal end of the light guide (FIG. 28A, FIG. 28B, FIG. 28C, and FIG. 28D), and the device is also equipped with a proximity determining element, and a signal generating element. The dental hygienist attaches the proximal end of the light guide to the head component to deliver the UVC light inside the mouth. Then the dental hygienist presses the power button on the base component of the device. The light guide is equipped with a proximity determining element that maintains the UVC light off until a predetermined treatment distance between the output end of the light guide and the treatment site is reached. Once the output end of the light guide reaches the predetermined distance from the treatment site, the proximity determining element activates a green light to signal to the dental hygienist that the predetermined distance has been achieved. Holding the device at the predetermined distance from the treatment site, the dental hygienist activates the UVC LED light positioned at the distal end of the light guide and delivers a therapeutic session of UVC light of 265 nm in wavelength, and power of 20 mW/cm$^2$ at a pulse frequency of 20 Hz for a duration 30 seconds. The UVC therapy is repeated, if necessary, for future treatment of gingivitis.

Example 12. Use of Therapeutic Device to Treat Periodontitis and Tooth Infection The therapeutic device described herein can be used to treat periodontitis and a tooth infection in the mouth of a patient. A dental professional (e.g., a dentist or a hygienist) uses a device for sterilizing an oral cavity and a dental caries. The head component is attached to a light guide equipped with a UVC LED at a distal end of the light guide (FIG. 28A, FIG. 28B, FIG. 28C, and FIG. 28D), and the device is also equipped with a proximity determining element and a signal generating element. The dental hygienist attaches the proximal end of the light guide to the head component to deliver the UVC light to the periodontal region of interest and to the infected region of the tooth. Then, the dental hygienist presses the power button on the base component of the device. The light guide is equipped with a proximity determining element that maintains the UVC light off until a predetermined treatment distance between the output end of the light guide and the treatment site is reached. Once the output end of the light guide reaches the predetermined distance from the treatment site, the proximity determining element activates a green light to signal to the dental hygienist that the predetermined distance has been achieved. Holding the device at the predetermined distance from the treatment site, the dental hygienist activates the UVC LED light positioned at the distal end of the light guide and delivers a therapeutic session of 265 nm UVC light and a power of 20 mW/cm$^2$ at a pulse frequency of 20 Hz for a duration 30 seconds. The UVC therapy is repeated, if necessary, for future treatment of periodontitis and tooth infection.

Example 13. Use of Therapeutic Device to Treat Cancer

The therapeutic device described herein can be used to cancer. A breast surgeon uses a device for treating breast cancer (FIGS. 28A-28D). The head component is attached to a light guide equipped with a UVC LED at a distal end of the light guide (FIGS. 28A-28D), and the device is also equipped with a proximity determining element and a signal generating element. The oncologist presses the power button on the base component activating the proximity determining element and draws the device near to the tumor site. The proximity determining element signals to the oncologist when a predetermined distance between the UVC light source at the distal end of the head component and the tumor site is reached. The proximity determining element activates a green light visible to the oncologist when the device is at the predetermined distance and activates a red light visible to the oncologist when the device is outside of the predetermined distance. Holding the therapeutic device at the predetermined distance from the neoplasia site, the oncologist activates the UVC light positioned at the distal end of the head component and delivers a therapeutic session of 265 nm UVC light at a pulse frequency of 5 Hz for a duration of 10 minutes. The UVC therapy is administered between 1-10 times with interleaved rest periods of one week.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and can be applied to the essential features hereinbefore set forth, and follows in the scope of the claims. Other embodiments are within the claims.

The invention claimed is:

1. A therapeutic device comprising a base component and a head component, the head component comprising a distal portion and a proximal portion, the distal portion of the head component is configured to deliver a therapeutic dose of UVC or ultraviolet A (UVA) radiation to an eye of a subject from a source of UVC or UVA radiation, and the proximal portion of the head component configured to be attached to the base component, the device further comprising:

a proximity determining element disposed on the head component and configured to detect a predetermined distance between the source of UVC or UVA radiation and a site of treatment of the eye;

an imaging module comprising a display that is configured to display an image of the site of treatment of the eye, wherein the display is coupled to the proximity determining element; and a signal generating element operatively connected to the display of the imaging module, wherein the display is configured to provide a visual signal upon detection of the predetermined distance by the proximity determining element and to activate the source of UVC or UVA radiation to deliver the therapeutic dose of UVC or UVA radiation to the eye of the subject, wherein the source of UVC or UVA radiation is configured to deliver the therapeutic dose of UVC or UVA radiation to an interior region of the eye of the subject through a light guide configured to insert into a hollow region of a vitrectomy element and enter the interior region of the eye of the subject;

wherein:

a) the proximity determining element comprises two or more lasers; or b) the proximity determining element is configured to activate the signal generating element upon convergence of two or more lasers;

wherein the source of UVC or UVA radiation comprises a plurality of light emitting diodes arranged in a circular array around the proximity determining element; and wherein a wavelength of the UVC radiation is from 100 nm to 290 nm, and wherein a wavelength of the UVA radiation is from 315 nm to 380 nm.

2. The device of claim 1, further comprising a light guide comprising a proximal portion and a distal portion, the proximal portion of the light guide configured to attach to the distal portion of the head component, and the distal portion of the light guide configured to deliver the therapeutic dose of UVC radiation.

3. The device of claim 1, further comprising an eye stabilizing element comprising a proximal end configured to attach to the distal portion of the head component and a distal end configured to contact and stabilize the eye.

4. The device of claim 3, wherein:

a) the eye stabilizing element is shaped as a cone comprising a first diameter at the proximal end and a second diameter at the distal end; or b) the eye stabilizing element is hollow to provide a volume through which a therapeutic dose of UVC radiation from the head component can travel to a treatment site of the eye of the subject.

5. The device of claim 3, wherein the distal end of the eye stabilizing element comprises a plurality of teeth configured to secure the eye of the subject.

6. The device of claim 3, comprising a component used to maintain an eyelid of the subject open.

7. A method for treating an eye infection or a cancer selected from an eyelid cancer an ocular cancer, an orbital cancer, or an adnexal cancer comprising:

(a) providing the device of claim 1 and positioning the device in proximity to the site of treatment;

(b) detecting the predetermined distance by the proximity determining element;

(c) generating the signal by the signal generating element to activate the source of UVC radiation; and (d) administering the therapeutic dose of UVC radiation to the site of treatment.

8. A method for treating corneal ectasia in a subject comprising:

(a) providing the device of claim 1 and positioning the device in proximity to the site of treatment, wherein the subject has been administered a dose of a photoactivator at the site of treatment;

(b) detecting the predetermined distance by the proximity determining element;

(c) generating the signal by the signal generating element to activate the source of UVA radiation; and (d) administering the therapeutic dose of UVA radiation to the site of treatment in the eye.

9. A method of treating a wound of a subject comprising:

(a) providing the device of claim 1; and (b) administering a therapeutic dose of UVC radiation to the wound.

10. A method for treating cancer comprising:

(a) providing the device of claim 1 and positioning the device in proximity to the site of treatment;

(b) detecting the predetermined distance by the proximity determining element;

(c) generating the signal by the signal generating element to activate the source of UVC radiation; and (d) administering the therapeutic dose of UVC radiation to the site of treatment.

11. The device of claim 1, wherein the head component is configured to deliver a pulsed dose of UVC radiation.

12. The device of claim 1, wherein the UVC radiation has a radiation intensity of from 20 $mW/cm^2$ to 1,000 $mW/cm^2$.

* * * * *